(12) United States Patent
Rossi et al.

(10) Patent No.: US 10,610,162 B2
(45) Date of Patent: *Apr. 7, 2020

(54) METHOD FOR THE DETECTING ELECTROCARDIOGRAM ANOMALIES AND CORRESPONDING SYSTEM

(71) Applicant: STMicroelectronics S.r.l., Agrate Brianza (IT)

(72) Inventors: Beatrice Rossi, Milan (IT); Pasqualina Fragneto, Burago di Molgora (IT); Diego Carrera, Lodi (IT); Giacomo Boracchi, Buccinasco (IT); Daniele Zambon, Castronno (IT)

(73) Assignee: STMICROELECTRONICS S.R.L., Agrate Brianza (IT)

( * ) Notice: Subject to any disclaimer, the term of this patent is extended or adjusted under 35 U.S.C. 154(b) by 48 days.

This patent is subject to a terminal disclaimer.

(21) Appl. No.: 15/696,051

(22) Filed: Sep. 5, 2017

(65) Prior Publication Data

US 2017/0360377 A1  Dec. 21, 2017

Related U.S. Application Data

(63) Continuation-in-part of application No. 15/169,184, filed on May 31, 2016.

(51) Int. Cl.
*A61B 5/00* (2006.01)
*A61B 5/0245* (2006.01)
(Continued)

(52) U.S. Cl.
CPC .......... *A61B 5/7267* (2013.01); *A61B 5/0245* (2013.01); *A61B 5/02438* (2013.01);
(Continued)

(58) Field of Classification Search
CPC . A61B 5/7267; A61B 5/02438; A61B 5/0245; A61B 5/0402
See application file for complete search history.

(56) References Cited

U.S. PATENT DOCUMENTS 9,289,150 B1  3/2016  Gupta et al.
2013/0120147 A1  5/2013  Narasimhan et al.
(Continued)

FOREIGN PATENT DOCUMENTS

WO  2008/065432 A1  6/2008
WO  2014/123512 A1  8/2014

OTHER PUBLICATIONS

Adler et al., "Sparse Coding with Anomaly Detection," *2013 IEEE International Workshop on Machine Learning for Signal Processing*, Southampton, United Kingdom, Sep. 22-25, 2013, 6 pages.
(Continued)

*Primary Examiner* — Joseph M Dietrich
(74) *Attorney, Agent, or Firm* — Seed IP Law Group LLP

(57) ABSTRACT

A heart-rate associated with a heartbeat signal is determined. A transform is selected based on the determined heart-rate associated with the heartbeat signal and a reference heart-rate associated with a dictionary of a sparse approximation model. The transform is selected independent of other factors associated with generation of the heartbeat signal. The selected transform is applied to the dictionary of the sparse approximation model, generating an adjusted dictionary of the sparse approximation model. Anomalous heartbeats in the heartbeat signal are detected using the adjusted dictionary of the sparse approximation model.

21 Claims, 35 Drawing Sheets
(23 of 35 Drawing Sheet(s) Filed in Color)

(51) Int. Cl.
| | |
|---|---|
| *A61B 5/0456* | (2006.01) |
| *A61B 5/0432* | (2006.01) |
| *A61B 5/0452* | (2006.01) |
| *A61B 5/04* | (2006.01) |
| *A61B 5/11* | (2006.01) |
| *A61B 5/024* | (2006.01) |
| *A61B 5/0472* | (2006.01) |
| *A61B 5/0468* | (2006.01) |

(52) U.S. Cl.
CPC ........ *A61B 5/04012* (2013.01); *A61B 5/0456* (2013.01); *A61B 5/0468* (2013.01); *A61B 5/0472* (2013.01); *A61B 5/04325* (2013.01); *A61B 5/04525* (2013.01); *A61B 5/1118* (2013.01); *A61B 5/7207* (2013.01); *A61B 5/7232* (2013.01); *A61B 5/7253* (2013.01); *A61B 5/0006* (2013.01); *A61B 5/0022* (2013.01); *A61B 5/04017* (2013.01); *A61B 5/6802* (2013.01); *A61B 5/7221* (2013.01); *A61B 5/7278* (2013.01); *A61B 2505/07* (2013.01); *A61B 2562/0219* (2013.01)

(56) References Cited

U.S. PATENT DOCUMENTS

| | | |
|---|---|---|
| 2015/0164349 A1 | 6/2015 | Gopalakrishnan et al. |
| 2016/0058386 A1* | 3/2016 | Wang ..................... A61B 5/721 600/509 |

OTHER PUBLICATIONS

Aharon et al., "K-SVD: An Algorithm for Designing Overcomplete Dictionaries for Sparse Representation," *IEEE Transactions on Signal Processing* 54(11):4311-4322, Nov. 2006.
Alippi et al., "Change Detection in Streams of Signals with Sparse Representations," *2014 IEEE International Conference on Acoustic, Speech, and Signal Processing (ICASSP)*, Florence, Italy, May 4-9, 2014, 5 pages.
Balouchestani et al., "Advanced K-Means Clustering Algorithm for Large ECG Data Sets Based on K-SVD Approach," *9th International Symposium on Communication Systems, Networks & Digital Sign (CSNDSP)*, IEEE, 2014, pp. 177-182.
Beck et al., "Gradient-Based Algorithms with Applications to Signal Recovery Problems." *Convex Optimization in Signal Processing and Communications*, Cambridge University Press, 2009, pp. 42-88. (49 pages).
Bergstra et al., "Random Search for Hyper-Parameter Optimization," *Journal of Machine Learning Research* 13:281-305, 2012.
Boyd et al., "Distributed Optimization and Statistical Learning via the Alternating Direction Method of Multipliers," *Foundations and Trends in Machine Learning* 3(1):1-122, 2010.
Carrera et al., "ECG Monitoring in Wearable Devices by Sparse Models," *Joint European Conference on Machine Learning and Knowledge Discovery in Databases*, Springer International Publishing, 2016. (16 pages).
De Chazal, et al., "Automatic Classification of Heartbeats Using ECG Morphology and Heartbeat Interval Features," *IEEE Transactions on Biomedical Engineering* 51(7):1196-1206, Jul. 2004.
Elad, *Sparse and Redundant Representations From Theory to Applications in Signal and Image Processing*, New York City, Springer, 2010, 376 pages.
Extended European Search Report, dated Sep. 19, 2017, for European Application No. 17150350.1-1657, 10 pages.
Goldberger et al., "PhysioBank, PhysioToolkit, and PhysioNet—Components of a New Research Resource for Complex Physiologic Signals," *Circulation* 101(23):e215-e220, Jun. 2000.
Lagerholm et al., "Clustering ECG Complexes Using Hermite Functions and Self-Organizing Maps," *IEEE Transactions on Biomedical Engineering* 47(7):838-848, Jul. 2000.
Lemos et al., "ECG Anomalies Identification Using a Time Series Novelty Detection Technique," in *IV Latin American Congress on Biomedical Engineering 2007, Bioengineering Solutions for Latin America Health*, Müller-Karger et al. (eds.), Berlin, Germany, Springer Berlin Heidelberg, 2008, pp. 65-68. (4 pages).
Li et al., "Detecting ECG Abnormalities via Transductive Transfer Learning," *Proceedings of the ACM Conference on Bioinformatics, Computational Biology and Biomedicine*, pp. 210-217, Oct. 2012.
Mann et al., *Braunwald's Heart Disease: A Textbook of Cardiovascular Medicine*, Elsevier Health Sciences, 2014, pp. 120-125.
Moody et al.,"MIT-BIH Arrhythmia Database Directory," URL= https://www.physionet.org/physiobank/database/html/mitdbdir/mitdbdir.htm, 1997, download date Sep. 13, 2017, 2 pages.
Pan et al., "A Real-Time QRS Detection Algorithm," *IEEE Transactions on Biomedical Engineering BME*-32(3):230-236, Mar. 1985.
Rubinstein et al., "Double Sparsity: Learning Sparse Dictionaries for Sparse Signal Approximation," *IEEE Transactions on Signal Processing* 58(3):1553-1564, 2010.
Shekhar et al., "Generalized Domain-Adaptive Dictionaries," *Proceedings of the IEEE Conference on Computer Vision and Pattern Recognition*, 2013, pp. 361-368.
Sivaraks et al., "Robust and Accurate Anomaly Detection in ECG Artifacts Using Time Series Motif Discovery," *Computational and Mathematical Methods in Medicine* 2015, Article ID 453214, 21 pages, 2015.
Tanantong et al., "False Alarm Reduction in BSN-Based Cardiac Monitoring Using Signal Quality and Activity Type Information," *Sensors* 15:3952-3974. 2015.
Yu, "On Decomposing the Proximal Map," *Advances in Neural Information Processing Systems*, 2013, pp. 91-99. (9 pages).

\* cited by examiner

FIG. 4

$s_A$  P  $s_{RWS}$

*FIG. 22*

METHOD FOR THE DETECTING ELECTROCARDIOGRAM ANOMALIES AND CORRESPONDING SYSTEM

BACKGROUND

Technical Field

The present disclosure relates to techniques for the detecting anomalies in Electrocardiogram (ECG) signals, such as signals acquired by wearable devices for health monitoring.

Description of the Related Art

Anomaly detection in ECG signals refers to the problem of finding patterns that do not conform to an expected behavior of the monitored signal. These abnormal patterns could translate to significant information such as anomalies in the heart activity (arrhythmias), failures in the sensing process, etc.

Wearable device may continuously acquire, store and periodically transmit physiological signals which are typically processed in real time by a host device. The morphological characteristics of ECG signals may show significant variations for different users, so generic methods may perform poorly on wearable devices. For example, each time a wearable device is repositioned or is subjected to accidental movement, the ECG morphology may be modified. The heart rate and the morphology of the beat may also change for daily activities.

BRIEF SUMMARY

ECG heartbeats acquired under normal conditions are characterized by specific morphological structures. On the other hand, ECG acquisitions that do not conform to such structures can be considered anomalies. In an embodiment, normal ECG heartbeats are assumed to be well described by a sparse model, such as a model based on the sparse representation theory. It is assumed that a normal heartbeat s can be modeled as $s = D \cdot x + e$, where D is an unknown dictionary, x is a sparse coefficient vector and e is a random noise coming from the sensing process. In an embodiment, a model is learned in a data-driven fashion, e.g., directly from the data acquired by a wearable device. During a learning phase, a dictionary D is determined which provides a sparse representation of a set of sensed training data. In a testing phase, for each acquired heartbeat s a sparse coefficient vector x is computed such that the reconstruction error, $\|s - D \cdot x\|_2$, is minimal (roughly speaking, the goodness of fit of such beat to the learned model is assessed). For anomalous beats, it is assumed the observed reconstruction error will exceed the tolerated noise energy.

In an embodiment, a method comprises: detecting a beat in a heartbeat signal; associating a heart rate and an energy of acceleration with the detected beat; selectively including the detected beat in a set of detected beats based on the heart rate and energy of acceleration associated with the detected beat; and performing at least one of: generating, using the set of detected beats as a set of training data, a dictionary of a sparse approximation model; and detecting anomalous beats in the set of detected beats using the dictionary of the sparse approximation model. In an embodiment, the method comprises: applying a beat transform based on the heart rate and energy of acceleration associated with a beat in the set of detected beats to the beat in the set of selected beats, generating an adapted beat; applying a dictionary transform based on the heart rate and energy of acceleration associated with the beat in the set of detected beats to the dictionary, generating an adapted dictionary; generating a sparse approximation of the adapted beat with respect to the adapted dictionary; and classifying the beat in the set of detected beats as anomalous based on the generated sparse approximation. In an embodiment, classifying the beat in the set of beats as anomalous based on the sparse approximation comprises: determining a root-mean-square error associated with the sparse approximation of the adapted beat; comparing the root-mean-square error to a threshold error; and classifying the beat in the set of beats as anomalous or normal based on the comparison. In an embodiment, the method comprises: in response to classification of the beat in the set of beats as anomalous, initiation a transmission of data related to the beat in the set of beats. In an embodiment, the method comprises: in response to classification of the beat in the set of beats as anomalous, storing data related to the beat in the set of beats. In an embodiment, the heart rate is a local heart rate and the selectively including the detected beat in the set of detected beats comprises: determining whether a punctual heart rate of the detected beat is an outlier heart rate with respect to the local heart rate associated with the detected beat; determining whether the detected beat is an outlier beat with respect to the energy of acceleration associated with the detected beat; excluding the detected beat from the set of detected beats when the punctual heart rate is an outlier heart rate with respect to the local heart rate and the detected beat is an outlier beat with respect to the energy of acceleration associated with the detected beat; including the detected beat in the set of detected beats when both the punctual heart rate is an inlier heart rate with respect to the local heart rate and the detected beat in an inlier beat with respect to the energy of acceleration associated with the detected beat; and excluding the detected beat from the set of detected beats and classifying it as a rhythmical anomaly beat when the punctual heart rate is an outlier heart rate with respect to the local heart rate and the detected beat is an inlier beat with respect to the energy of acceleration associated with the detected beat. In an embodiment, the method comprises: applying a beat transform based on the heart rate and energy of acceleration associated with a beat in the set of detected beats to the beat in the set of selected beats, generating an adapted beat; applying a dictionary transform based on the heart rate and energy of acceleration associated with the beat in the set of detected beats to the dictionary, generating an adapted dictionary; generating a sparse approximation of the adapted beat with respect to the adapted dictionary; and classifying the beat in the set of detected beats as anomalous based on the generated sparse approximation of the adapted beat. In an embodiment, the method comprises: generating the sparse representation dictionary using the set of detected beats as the set of training data by iteratively: generating coefficients of a sparse representation matrix; and optimizing the dictionary and the coefficients of the sparse representation matrix. In an embodiment, the heart rate is a reference heart rate associated with the set of detected beats and the selectively including the detected beat in the set of detected beats comprises: determining whether a punctual heart rate of the detected beat is an outlier heart rate with respect to the reference heart rate; determining whether the detected beat is an outlier beat with respect to the energy of acceleration associated with the detected beat; excluding the detected beat from the set of detected beats when the punctual heart rate is an outlier heart rate with respect to the reference heart rate; and excluding the detected beat from the set of detected beats when the detected beat is an outlier beat with respect to the energy of acceleration associated with the detected beat. In an embodiment, the method comprises: generating, using the set of detected beats as the set of training data, the dictionary of the sparse approximation model, wherein the heartbeat signal is a training heartbeat signal; detecting a beat in a test heartbeat signal; associating a local heart rate and an energy of acceleration with the detected beat in the test heartbeat signal; selectively including the detected beat in a set of test beats based on the local heart rate and energy of acceleration associated with the detected beat in the test heartbeat signal; and detecting anomalous beats in the set of test beats using the dictionary of the sparse approximation model. In an embodiment, a device is configured to perform one or more of the methods disclosed herein.

In an embodiment, a device comprises: an interface configured to receive a test heart-beat signal and one or more acceleration signals: and signal processing circuitry configured to: detect a beat in the test heartbeat signal; associate a heart rate and an energy of acceleration with the detected beat; selectively include the detected beat in a set of test beats based on the heart rate and energy of acceleration associated with the detected beat; and detect anomalous beats in the set of test beats using a dictionary of a sparse approximation model. In an embodiment, the signal processing circuitry, in operation: applies a beat transform based on the heart rate and energy of acceleration associated with a beat in the set of test beats to the beat in the set of selected beats, generating an adapted beat; applies a dictionary transform based on the heart rate and energy of acceleration associated with the beat in the set of test beats to the dictionary, generating an adapted dictionary; generates a sparse approximation of the adapted beat with respect to the adapted dictionary; and generates a signal indicative of whether the beat in the set of test beats is anomalous based on the generated sparse approximation. In an embodiment, generating the signal indicative of whether the beat in the set of test beats is anomalous based on the generated sparse approximation comprises: determining a root-mean-square error associated with the generated sparse approximation of the adapted beat; comparing the root-mean-square error to a threshold error; and generating the signal based on the comparison. In an embodiment, when the generated signal indicates the beat in the set of test beats is anomalous, the signal processing circuitry initiates a transmission of data related to the beat in the set of test beats. In an embodiment, the heart rate is a local heart rate and the selectively including the detected beat in the set of test beats comprises: determining whether a punctual heart rate of the detected beat is an outlier heart rate with respect to the local heart rate associated with the detected beat; determining whether the detected beat is an outlier beat with respect to the energy of acceleration associated with the detected beat; excluding the detected beat from the set of detected beats when either the punctual heart rate is an outlier heart rate with respect to the local heart rate or the detected beat is an outlier beat with respect to the energy of acceleration associated with the detected beat; and including the detected beat in the set of detected beats when both the punctual heart rate is an inlier heart rate with respect to the local heart rate and the detected beat in an inlier beat with respect to the energy of acceleration associated with the detected beat. In an embodiment, the interface is configured to receive a training heartbeat signal; and the signal processing circuitry is configured to: detect a beat of the training heartbeat signal; associate a reference heart rate and an energy of acceleration with the detected beat of the training heartbeat signal; selectively include the detected beat of the training heartbeat signal in a set of training data based on the heart rate and energy of acceleration associated with the detected beat in the training heartbeat signal; and generate the dictionary of the sparse representation model using the set of training data. In an embodiment, the signal processing circuitry generates the dictionary of the sparse representation model by iteratively: generating coefficients of a sparse representation matrix; and optimizing the dictionary and the coefficients of the sparse representation matrix. In an embodiment, the reference heart rate is associated with the training heart beat signal and the selectively including the detected beat of the training heartbeat signal in the set of training data comprises: determining whether a punctual heart rate of the detected beat of the training heartbeat signal is an outlier heart rate with respect to the reference heart rate; determining whether the detected beat of the training heartbeat signal is an outlier beat with respect to the energy of acceleration associated with the detected beat of the training heartbeat signal; excluding the detected beat of the training heartbeat signal from the set of training data when the punctual heart rate is an outlier heart rate with respect to the reference heart rate; and excluding the detected beat of the training heartbeat signal from the set of training data when the detected beat of the training heartbeat signal is an outlier beat with respect to the energy of acceleration associated with the detected beat of the training heartbeat signal.

In an embodiment, a system comprises: a sensor configured to generate heartbeat signals; an accelerometer configured to generate one or more acceleration signals; and signal processing circuitry configured to: detect a beat of a test heartbeat signal; associate a heart rate and an energy of acceleration with the detected beat of the test heartbeat signal; selectively include the detected beat of the test heartbeat signal in a set of test beats based on the heart rate and energy of acceleration associated with the detected beat of the test heartbeat signal; and detect anomalous beats in the set of test beats using a dictionary of a sparse approximation model. In an embodiment, the signal processing circuitry, in operation: applies a beat transform based on the heart rate and energy of acceleration associated with a beat in the set of test beats to the beat in the set of selected beats, generating an adapted beat; applies a dictionary transform based on the heart rate and energy of acceleration associated with the beat in the set of test beats to the dictionary, generating an adapted dictionary; generates a sparse approximation of the adapted beat with respect to the adapted dictionary; and generates a signal indicative of whether the beat in the set of test beats is anomalous based on the generated sparse approximation. In an embodiment, the signal processing circuitry is configured to: detect a beat of a training heartbeat signal; associate a reference heart rate and an energy of acceleration with the detected beat of the training heartbeat signal; selectively include the detected beat of the training heartbeat signal in a set of training data based on the heart rate and energy of acceleration associated with the detected beat in the training heartbeat signal; and generate the dictionary of the sparse representation model using the set of training data. In an embodiment, the signal processing circuitry generates the dictionary of the sparse representation model by iteratively: generating coefficients of a sparse representation matrix; and optimizing the dictionary and the coefficients of the sparse representation matrix.

In an embodiment, a non-transitory computer-readable medium's contents configure a heart-rate monitoring device to perform a method, the method comprising: detecting a beat of a test heartbeat signal; associating a heart rate and an energy of acceleration with the detected beat of the test heartbeat signal; selectively including the detected beat of the test heartbeat signal in a set of test beats based on the heart rate and energy of acceleration associated with the detected beat of the test heartbeat signal; and detecting anomalous beats in the set of test beats using a dictionary of a sparse approximation model. In an embodiment, the method comprises: applying a beat transform based on the heart rate and energy of acceleration associated with a beat in the set of test beats to the beat in the set of selected beats, generating an adapted beat; applying a dictionary transform based on the heart rate and energy of acceleration associated with the beat in the set of test beats to the dictionary, generating an adapted dictionary; generating a sparse approximation of the adapted beat with respect to the adapted dictionary; and generating a signal indicative of whether the beat in the set of test beats is anomalous based on the generated sparse approximation. In an embodiment, the method comprises: detecting a beat of a training heartbeat signal; associating a reference heart rate and an energy of acceleration with the detected beat of the training heartbeat signal; selectively including the detected beat of the training heartbeat signal in a set of training data based on the heart rate and energy of acceleration associated with the detected beat in the training heartbeat signal; and generating the dictionary of the sparse representation model using the set of training data. In an embodiment, the method comprises generating the dictionary of the sparse representation model by iteratively: generating coefficients of a sparse representation matrix; and optimizing the dictionary and the coefficients of the sparse representation matrix.

In an embodiment, a system comprises: means for generating heartbeat signals; means for generating acceleration signals; and means for processing a test heartbeat signal, by: detecting a beat of the test heartbeat signal; associating a heart rate and an energy of acceleration with the detected beat of the test heartbeat signal; selectively including the detected beat of the test heartbeat signal in a set of test beats based on the heart rate and energy of acceleration associated with the detected beat of the test heartbeat signal; and detecting anomalous beats in the set of test beats using a dictionary of a sparse approximation model. In an embodiment, the processing the test heartbeat signal comprises: applying a beat transform based on the heart rate and energy of acceleration associated with a beat in the set of test beats to the beat in the set of selected beats, generating an adapted beat; applying a dictionary transform based on the heart rate and energy of acceleration associated with the beat in the set of test beats to the dictionary, generating an adapted dictionary; generating a sparse approximation of the adapted beat with respect to the adapted dictionary; and generating a signal indicative of whether the beat in the set of test beats is anomalous based on the generated sparse approximation. In an embodiment, the system comprises: means for processing a training heartbeat signal, by: detecting a beat of the training heartbeat signal; associating a reference heart rate and an energy of acceleration with the detected beat of the training heartbeat signal; selectively including the detected beat of the training heartbeat signal in a set of training data based on the heart rate and energy of acceleration associated with the detected beat in the training heartbeat signal; and generating the dictionary of the sparse representation model using the set of training data. In an embodiment, the processing the training heartbeat signal comprises generating the dictionary of the sparse representation model by iteratively: generating coefficients of a sparse representation matrix; and optimizing the dictionary and the coefficients of the sparse representation matrix.

In an embodiment, a method comprises: determining a heart-rate associated with a heartbeat signal; selecting a transform based on the determined heart-rate associated with the heartbeat signal and a reference heart-rate associated with a dictionary of a sparse approximation model, wherein the transform is selected independent of other factors associated with generation of the heartbeat signal; applying the selected transform to the dictionary of the sparse approximation model, generating an adjusted dictionary of the sparse approximation model; and detecting anomalous heartbeats in the heartbeat signal using the adjusted dictionary of the sparse approximation model. In an embodiment, selecting the transform comprises selecting one of a family of transforms associated with respective pairs of heart-rates. In an embodiment, the method comprises: generating the dictionary of the sparse approximation model. In an embodiment, the transform is a first transform, and the method comprises: selecting a second transform based on the determined heart rate and at least one other factor associated with the heartbeat signal; and applying the first and second transforms to the dictionary of the sparse approximation model. In an embodiment, the method comprises: generating a sparse approximation of a beat in a set of beats detected in the heartbeat signal with respect to the adjusted dictionary; and classifying the beat in the set of detected beats as anomalous based on the generated sparse approximation. In an embodiment, classifying the beat in the set of beats as anomalous based on the sparse approximation comprises: determining a root-mean-square error associated with the sparse approximation of the beat; comparing the root-mean-square error to a threshold error; and classifying the beat in the set of beats as anomalous or normal based on the comparison. In an embodiment, the method comprises: in response to classification of the beat in the set of beats as anomalous, initiating a transmission of data related to the beat in the set of beats. In an embodiment, the beat is an adjusted beat. In an embodiment, the method comprises filtering beats in the set of detected beats.

In an embodiment, a device comprises: an interface, which, in operation receives a test heartbeat signal: and signal processing circuitry, which, in operation: determines a heart-rate associated with the test heartbeat signal; selects a transform based on the determined heart-rate associated with the test heartbeat signal and a reference heart-rate associated with a dictionary of a sparse approximation model, wherein the transform is selected independent of other factors associated with generation of the test heartbeat signal; applies the selected transform to the dictionary of the sparse approximation model, generating an adjusted dictionary of the sparse approximation model; and detects anomalous heartbeats in the test heartbeat signal using the adjusted dictionary of the sparse approximation model. In an embodiment, the transform is a first transform and the signal processing circuitry, in operation: selects a second transform based on the determined heart-rate and at least one other factor associated with the test heartbeat signal; and applies the first and second transforms to the dictionary of the sparse approximation model. In an embodiment, the signal processing circuitry, in operation: generates a sparse approximation of a beat in a set of beats detected in the test heartbeat signal with respect to the adjusted dictionary; and classifies the beat in the set of detected beats as anomalous based on the generated sparse approximation. In an embodiment, the classifying the beat in the set of beats as anomalous based on the sparse approximation comprises: determining a root-mean-square error associated with the sparse approximation of the beat; comparing the root-mean-square error to a threshold error; and classifying the beat in the set of beats as anomalous or normal based on the comparison. In an embodiment, the signal processing circuitry in response to classification of the beat in the set of beats as anomalous, initiates a transmission of data related to the beat in the set of beats. In an embodiment, the signal processing circuitry, in operation, adjusts the beat in the seat of beats. In an embodiment, the signal processing circuitry, in operation, filters beats in the set of detected beats. In an embodiment, the interface, in operation, receives a training heartbeat signal; and the signal processing circuitry, in operation: detects a beat of the training heartbeat signal; associates a reference heart rate and an energy of acceleration with the detected beat of the training heartbeat signal; selectively includes the detected beat of the training heartbeat signal in a set of training data based on the heart rate and energy of acceleration associated with the detected beat in the training heartbeat signal; and generates the dictionary of the sparse representation model using the set of training data.

In an embodiment, a system, comprises: a sensor, which, in operation, generates heartbeat signals; an accelerometer, which, in operation, generates one or more acceleration signals; and signal processing circuitry, which, in operation: determines a heart-rate associated with a test heartbeat signal; selects a transform based on the determined heart-rate associated with the test heartbeat signal and a reference heart-rate associated with a dictionary of a sparse approximation model, wherein the transform is selected independent of other factors associated with generation of the test heartbeat signal; applies the selected transform to the dictionary of the sparse approximation model, generating an adjusted dictionary of the sparse approximation model; and detects anomalous heartbeats in the test heartbeat signal using the adjusted dictionary of the sparse approximation model. In an embodiment, the transform is a first transform and the signal processing circuitry, in operation: selects a second transform based on the determined heart-rate and at least one other factor associated with the test heartbeat signal; and applies the first and second transforms to the dictionary of the sparse approximation model. In an embodiment, the signal processing circuitry, in operation: generates a sparse approximation of a beat in a set of beats detected in the test heartbeat signal with respect to the adjusted dictionary; and classifies the beat in the set of detected beats as anomalous based on the generated sparse approximation. In an embodiment, the signal processing circuitry, in operation: detects a beat of a training heartbeat signal; associates a reference heart rate and an energy of acceleration with the detected beat of the training heartbeat signal; selectively includes the detected beat of the training heartbeat signal in a set of training data based on the heart rate and energy of acceleration associated with the detected beat in the training heartbeat signal; and generates the dictionary of the sparse representation model using the set of training data.

In an embodiment, a non-transitory computer-readable medium has contents which configure a heart-rate monitoring device to perform a method, the method comprising: determining a heart-rate associated with a test heartbeat signal; selecting a transform based on the determined heart-rate associated with the test heartbeat signal and a reference heart-rate associated with a dictionary of a sparse approximation model, wherein the transform is selected independent of other factors associated with generation of the test heartbeat signal; applying the selected transform to the dictionary of the sparse approximation model, generating an adjusted dictionary of the sparse approximation model; and detecting anomalous heartbeats in the test heartbeat signal using the adjusted dictionary of the sparse approximation model. In an embodiment, the contents comprise instructions executed by processing circuitry of the heart-rate monitoring device. In an embodiment, wherein the method comprises: detecting a beat of a training heartbeat signal; associating a reference heart rate and an energy of acceleration with the detected beat of the training heartbeat signal; selectively including the detected beat of the training heartbeat signal in a set of training data based on the heart rate and energy of acceleration associated with the detected beat in the training heartbeat signal; and generating the dictionary of the sparse representation model using the set of training data.

In an embodiment, a method comprises: learning a plurality of dictionaries of sparse representation models of heartbeats associated with a plurality of users and a plurality of heart-rates; solving an optimization problem for multiple sets of dictionaries of the plurality of dictionaries with respect to pairs of the plurality of heart-rates, generating a family of transforms; selecting a transform of the family of transforms based on a target heart rate and a reference heart-rate, wherein the reference heart-rate is associated with a dictionary of another sparse representation model of heartbeat; and applying the selected transform to the dictionary of the another sparse representation model, generating an adjusted dictionary. In an embodiment, the method comprises: detecting anomalous heartbeats in a test set of heartbeats using the adjusted dictionary. In an embodiment, solving the optimization problem comprises using an Alternating Direction Method of Multipliers (ADMM) algorithm.

In an embodiment, a non-transitory computer-readable medium has contents which cause processing circuitry to perform a method, the method comprising: learning a plurality of dictionaries of sparse representation models of heartbeats associated with a plurality of users and a plurality of heart-rates; solving an optimization problem for multiple sets of dictionaries of the plurality of dictionaries with respect to pairs of the plurality of heart-rates, generating a family of transforms; selecting a transform of the family of transforms based on a target heart rate and a reference heart-rate, wherein the reference heart-rate is associated with a dictionary of another sparse representation model of heartbeat; and applying the selected transform to the dictionary of the another sparse representation model, generating an adjusted dictionary. In an embodiment, the method comprises: detecting anomalous heartbeats in a test set of heartbeats using the adjusted dictionary. In an embodiment, solving the optimization problem comprises using an Alternating Direction Method of Multipliers (ADMM) algorithm.

In an embodiment, a system comprises: one or more memories; and processing circuitry, which, in operation: learns a plurality of dictionaries of sparse representation models of heartbeats associated with a plurality of users and a plurality of heart-rates; solves an optimization problem for multiple sets of dictionaries of the plurality of dictionaries with respect to pairs of the plurality of heart-rates, generating a family of transforms; selects a transform of the family of transforms based on a target heart rate and a reference heart-rate, wherein the reference heart-rate is associated with a dictionary of another sparse representation model of heartbeat; and applies the selected transform to the dictionary of the another sparse representation model, generating an adjusted dictionary. In an embodiment, the processing circuitry, in operation: detects anomalous heartbeats in a test set of heartbeats using the adjusted dictionary. In an embodiment, solving the optimization problem comprises using an Alternating Direction Method of Multipliers (ADMM) algorithm.

BRIEF DESCRIPTION OF THE SEVERAL VIEWS OF THE DRAWINGS

The patent or application file contains at least one drawing executed in color. Copies of this patent or patent application publication with color drawings will be provided by the Office upon request and payment of the necessary fee.

Figure 4:
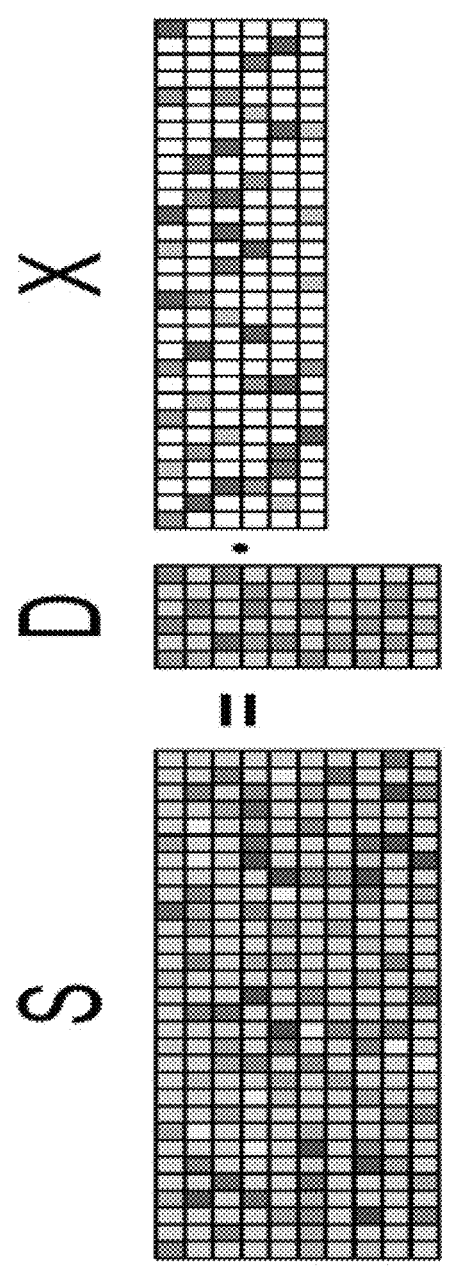

FIG. 4 is a graphical illustration of an embodiment of a learned sparse model.

FIG. 20 is a graphical illustration of an example application of beat adaptation in an embodiment.

Figures 21, 22:
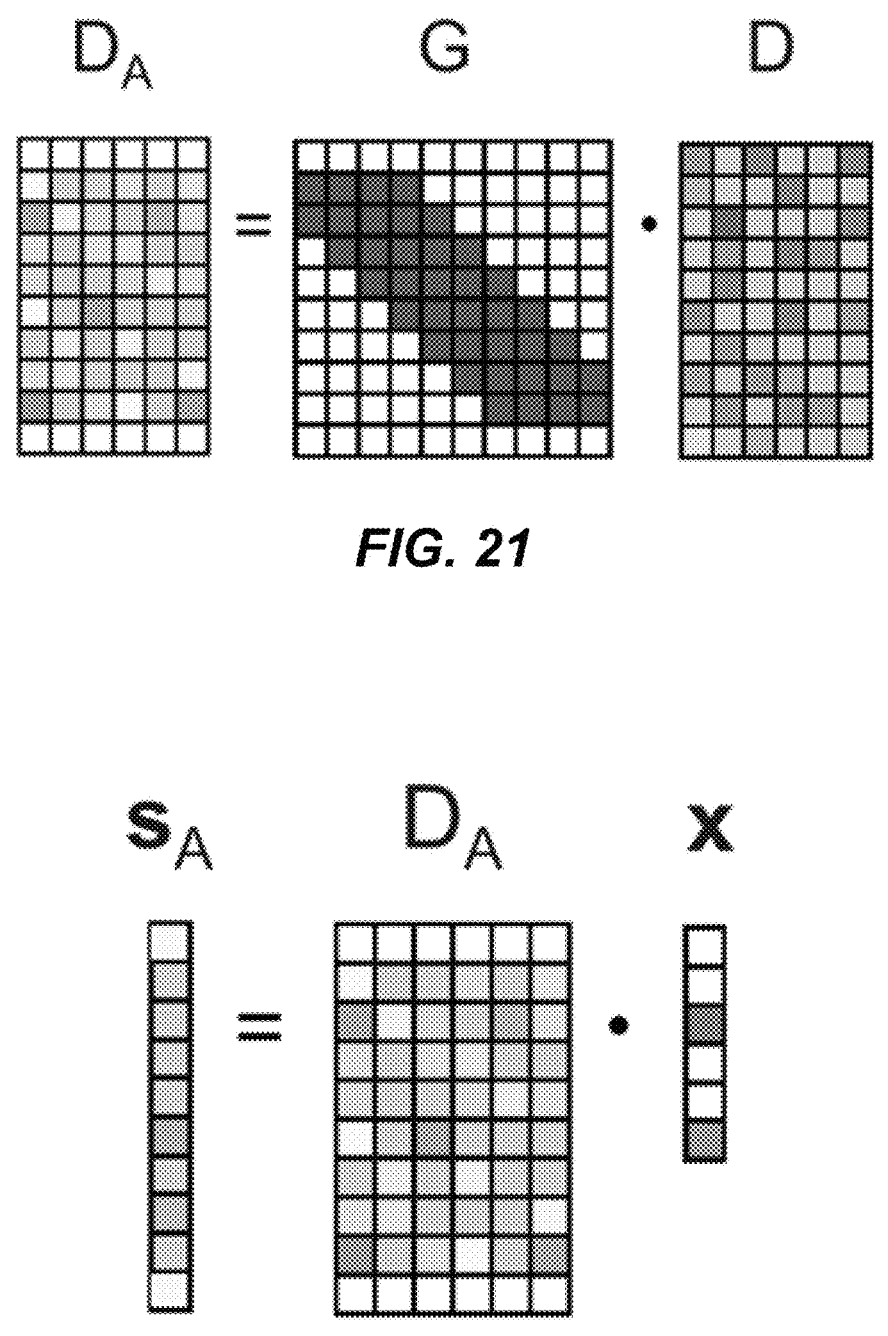

FIG. 21 is a graphical illustration of an example application of dictionary adaptation in an embodiment.

FIG. 22 is a graphical illustration of relationships between an adapted signal vector, a sparse representation coefficient vector and an adapted dictionary in an iteration of an Orthogonal Matching Pursuit (OMP) algorithm in an embodiment.

DETAILED DESCRIPTION

Figure 1:
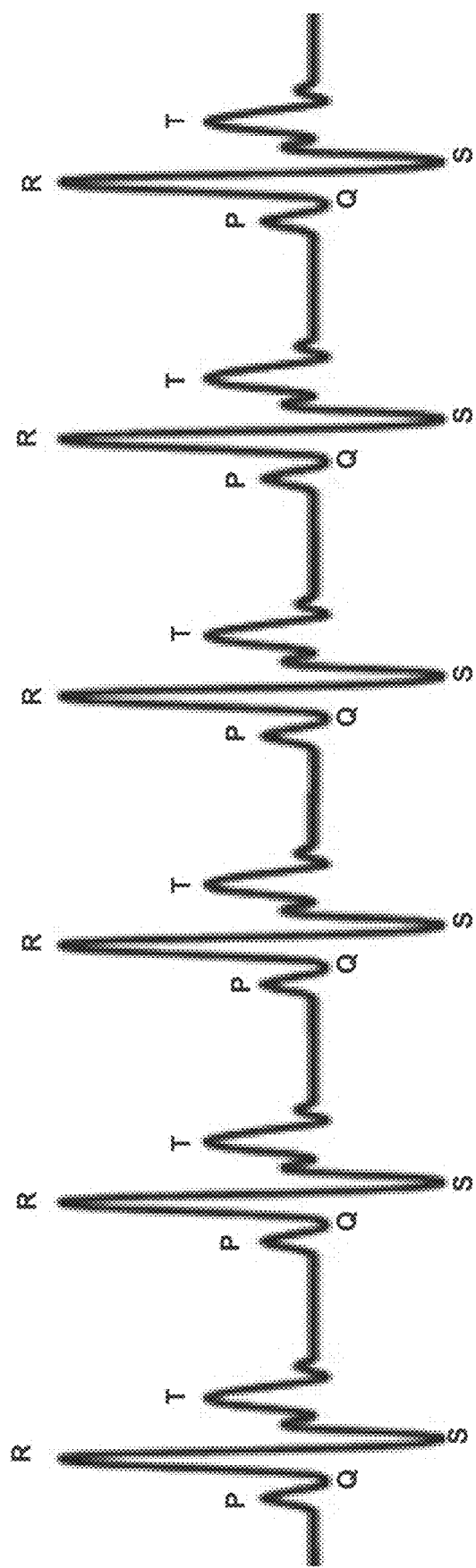
FIG. 1 illustrates an example morphological structure of normal heart beats.

In the following description, certain details are set forth in order to provide a thorough understanding of various embodiments of devices, systems, methods and articles. However, one of skill in the art will understand that other embodiments may be practiced without these details. In other instances, well-known structures and methods associated with, for example, wearable devices and signal processing circuitry, such as transistors, multipliers, transmitters, NFC circuits, integrated circuits, etc., have not been shown or described in detail in some figures to avoid unnecessarily obscuring descriptions of the embodiments.

Unless the context requires otherwise, throughout the specification and claims which follow, the word "comprise" and variations thereof, such as "comprising," and "comprises," are to be construed in an open, inclusive sense, that is, as "including, but not limited to."

Reference throughout this specification to "one embodiment," or "an embodiment" means that a particular feature, structure or characteristic described in connection with the embodiment is included in at least one embodiment. Thus, the appearances of the phrases "in one embodiment," or "in an embodiment" in various places throughout this specification are not necessarily referring to the same embodiment, or to all embodiments. Furthermore, the particular features, structures, or characteristics may be combined in any suitable manner in one or more embodiments to obtain further embodiments.

The headings are provided for convenience only, and do not interpret the scope or meaning of this disclosure.

The sizes and relative positions of elements in the drawings are not necessarily drawn to scale. For example, the shapes of various elements and angles are not drawn to scale, and some of these elements are enlarged and positioned to improve drawing legibility. Further, the particular shapes of the elements as drawn are not necessarily intended to convey any information regarding the actual shape of particular elements, and have been selected solely for ease of recognition in the drawings.

Normal ECG signals acquired under normal conditions may be characterized by specific morphological structures or patterns. On the other hand, ECG acquisitions that do not conform to such structures may be considered anomalies. The morphology of a normal state may be complex, and an analytic or approximate model may be difficult to develop.

The present disclosure proposes instead of using an analytic or approximate model, that a data-driven learning procedure be employed, which in an embodiment is user specific, adaptable to changes in the user's state, and which is easily reconfigured by performing an unsupervised and robust learning stage.

ECG heart beats acquired under normal states may be characterized by specific morphological structures. FIG. 1 illustrates an example morphological structure of normal heart beats, and includes P, Q, R, S and T waves. In an embodiment, a model is developed or learned from a set of training data which provides a sparse representation of the normal data. In a testing phase, the reconstruction error, namely the discrepancy of test signals from the learned model, may be monitored in order to detect anomalies. For example, when the reconstruction error exceeds a threshold value, a beat may be classified as anomalous. A user state may be characterized as a combination of two features, a heart rate HR and a measure of energy in the acceleration EE.

Sparse representation may allow complex signals to be modeled by sparse linear combinations, such as linear combinations where only a few coefficients are non-zero, of a redundant set of atoms constituting a dictionary. Using sparse representation modeling of the morphology of normal ECG signals may facilitate simplifying signal processing tasks associated with detecting anomalous heart beats.

Non-sparse representation models have been proposed. See Li, et al., *Detecting ecg abnormalities via transductive transfer learning*, in Proceedings of the ACM Conference on Bioinformatics, Computational Biology and Biomedicine, pp. 210-217, ACM, 2012; Lagerholm, et al., *Clustering ECG complexes using hermite functions and self-organizing maps*, Biomedical Engineering, IEEE Transactions on, vol. 47, no. 7, pp. 838-848, 2000; Sivaraks, et al., *Robust and accurate Anomaly detection in ECG artifacts using time series motif discovery*, Comp. Math. Methods in Medicine 2015. Li has the disadvantage that all the data must be continuously transmitted from a wearable device to a host in order for the data to be analyzed. Lagerholm adopts an unsupervised clustering procedure based on neural networks and is directed to a classification problem of several different types of heart beats rather than anomaly detection. Lagerholm also may be difficult to implement on a wearable device. Sivaraks does not support real-time detection. While Alder, et al., *Sparse coding with anomaly detection,*" Proceedings of IEEE, International Workshop on Machine Learning for Signal Processing (MLSP), September 2003, pp 1-6, proposes learning a specific model for a user, the approach in Alder is not robust, and is not adaptable to changes in a user state.

The term sparse refers to a measurable property of a vector that concerns the number of its non-zero entries. The $l_0$-pseudonorm (referred to herein as $l_0$-norm or operator) measures the sparsity of a vector. The $l_0$-norm of a vector $x \in \mathbb{R}^N$ is the number of non-zero entries in $x$. The notation $\|x\|_0$ is used to represent the $l_0$-norm of $x$. A vector $x$ is considered to be T-sparse if $\|x\|_0 \leq T$.

The $l_1$-norm is the sum of the absolute value of the entries in a vector. The $l_2$-norm is the Euclidean length of a vector (the square root of the sum of the absolute squares of the elements of a vector). The Frobenius norm is the square root of the sum of the absolute squares of the elements of a matrix. The notation $\|\cdot\|_1$, $\|\cdot\|_2$, and $\|\cdot\|_F$ will be used for the $l_1$, $l_2$ and Frobenius norms respectively.

Given N vectors $d_i \in \mathbb{R}^M$ for $i=1, \ldots, N$, a dictionary in the form of a matrix may be defined as $$D=[d_1| \ldots |d_N] \in \mathbb{R}^{M \times N} \tag{1}$$

with the columns $d_i$ referred to as atoms. If M<N, D is considered to be an over complete dictionary.

Let $D \in \mathbb{R}^{M \times N}$ be an over complete dictionary and let $s \in \mathbb{R}^M$ be a given data vector. A $\mathcal{P}_0$ problem may be represented as $$\underset{x}{\mathrm{argmin}} \|x\|_0 \text{ s.t. } Dx = s. \tag{2}$$

In the above problem if a sparse vector $x \in \mathbb{R}^N$ is found as a solution, $x$ is called a sparse representation of $s$. In general, sparsest approximations are not unique but there are conditions in which they can be. For more details about conditions for uniqueness of sparse representation please refer to M. Elad, *Sparse and Redundant Representations: From Theory to Applications in Signal and Image Processing*, Springer Pub. Co. 1st Ed. 2010.

A more general version of the problem of equation (2) addresses the presence of noise in the data, which is a realistic assumption in real applications. More particularly, it may be assumed that the following model holds:

$$s=Dx+e, \tag{3}$$

where $e$ is a noise term, which includes both errors in the measurement and in the approximation model. In this case the signal s may be approximated by sparse representations with respect to the dictionary D, $s \approx Dx$. Let $\varepsilon \in \mathbb{R}$ be fixed, we define the $\mathcal{P}_0^\varepsilon$ problem as $$\underset{x}{\mathrm{argmin}} \|x\|_0 \text{ s.t. } \|Dx - s\|_2 \leq \varepsilon. \tag{4}$$

If a sparse vector $x \in \mathbb{R}^N$ is a solution to the above problem it is a sparse approximation of s. In this problem there is more flexibility of choice for x since it is no longer necessary to reproduce s exactly. In the $\mathcal{P}_0^\varepsilon$ problem a noise term is included in the model, in other words, the system s=Dx+e is considered, where e represents a noise component. In this case, instead of uniqueness conditions, theoretical results examine the stability of the solution x given an upper bound on the noise magnitude $\|e\|_2$. See, Elad. Another useful formulation for the case $s \approx Dx$ which explicitly forces a T-sparsity constraint on x is the following $$\underset{x}{\mathrm{argmin}} \|Dx - s\|_2 \text{ s.t. } \|x\|_0 \leq T \tag{5}$$

with T a known fixed value. This formulation is referred to herein as $\mathcal{P}_0^T$ problem. If a sparse vector $x \in \mathbb{R}^N$ is a solution to the $\mathcal{P}_0^T$ problem, then x is a sparse approximation of s. In this problem there also is more flexibility of choice for x since it is no longer necessary to reproduce s exactly. In this case as well, instead of uniqueness conditions, theoretical results examine the stability of the solution x given an upper bound on the noise magnitude $\|e\|_2$. See, Elad.

Figure 2:
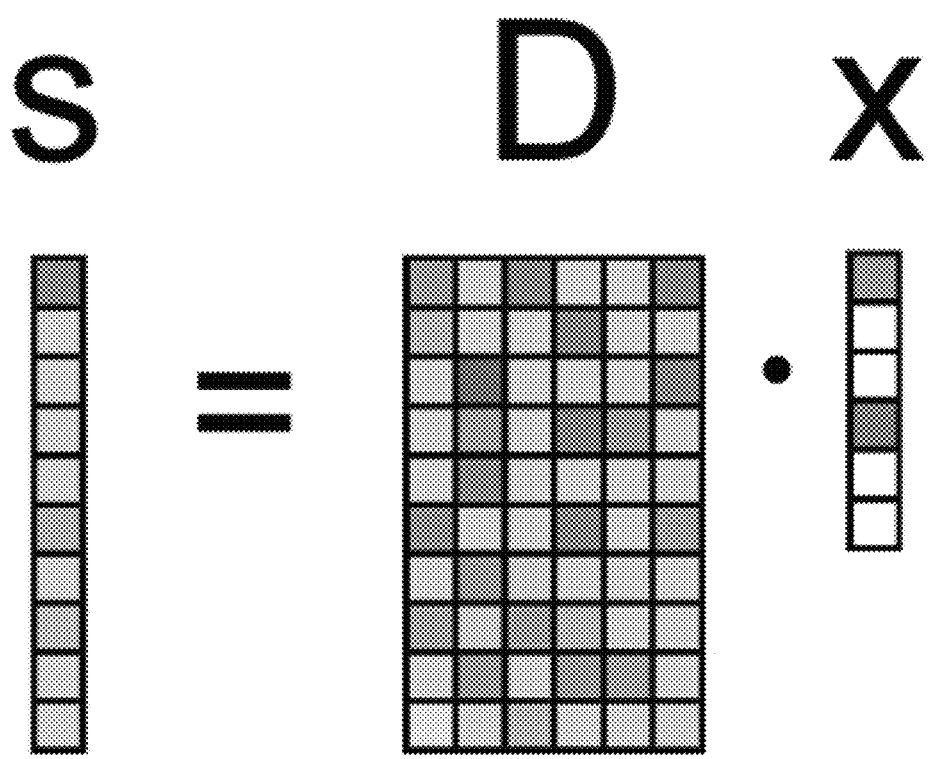
FIG. 2 is a graphical illustration of relationships between a signal vector, a sparse representation coefficient vector and a dictionary in an iteration of an Orthogonal Matching Pursuit (OMP) algorithm in an embodiment.

Orthogonal Matching Pursuit (OMP) is a greedy algorithm for finding an approximate solution to $\mathcal{P}_0^\epsilon$ and $\mathcal{P}_0^T$ problems. OMP constructs an approximation by going through an iteration process. At each iteration, the locally optimum solution is calculated (for example, for equation 5). This may be done by finding the column vector in D which most closely resembles a residual vector r. The residual vector starts out being equal to the vector that is being approximated, $r^{(0)}=s$, and is adjusted at each iteration to take into account the vector previously chosen. This sequence of locally optimum solutions may lead to the global optimum solution. As usual this is not the case in general although there are conditions under which the result will be the optimum solution. OMP is based on a variation of an earlier algorithm called Matching Pursuit (MP). MP simply removes the selected column vector from the residual vector at each iteration. OMP instead uses a least-squares step at each iteration to update the residual vector in order to improve the approximation. The usual termination criteria for these iterations are $\|r^{(i)}\|_2 \leq 2$ or $\|x^{(i)}\|_0 \geq T$ or a combination thereof. FIG. 2 is a graphical illustration of the relationships between the vectors S and X and a dictionary D in an iteration of an OMP algorithm in an embodiment.

Figure 3:
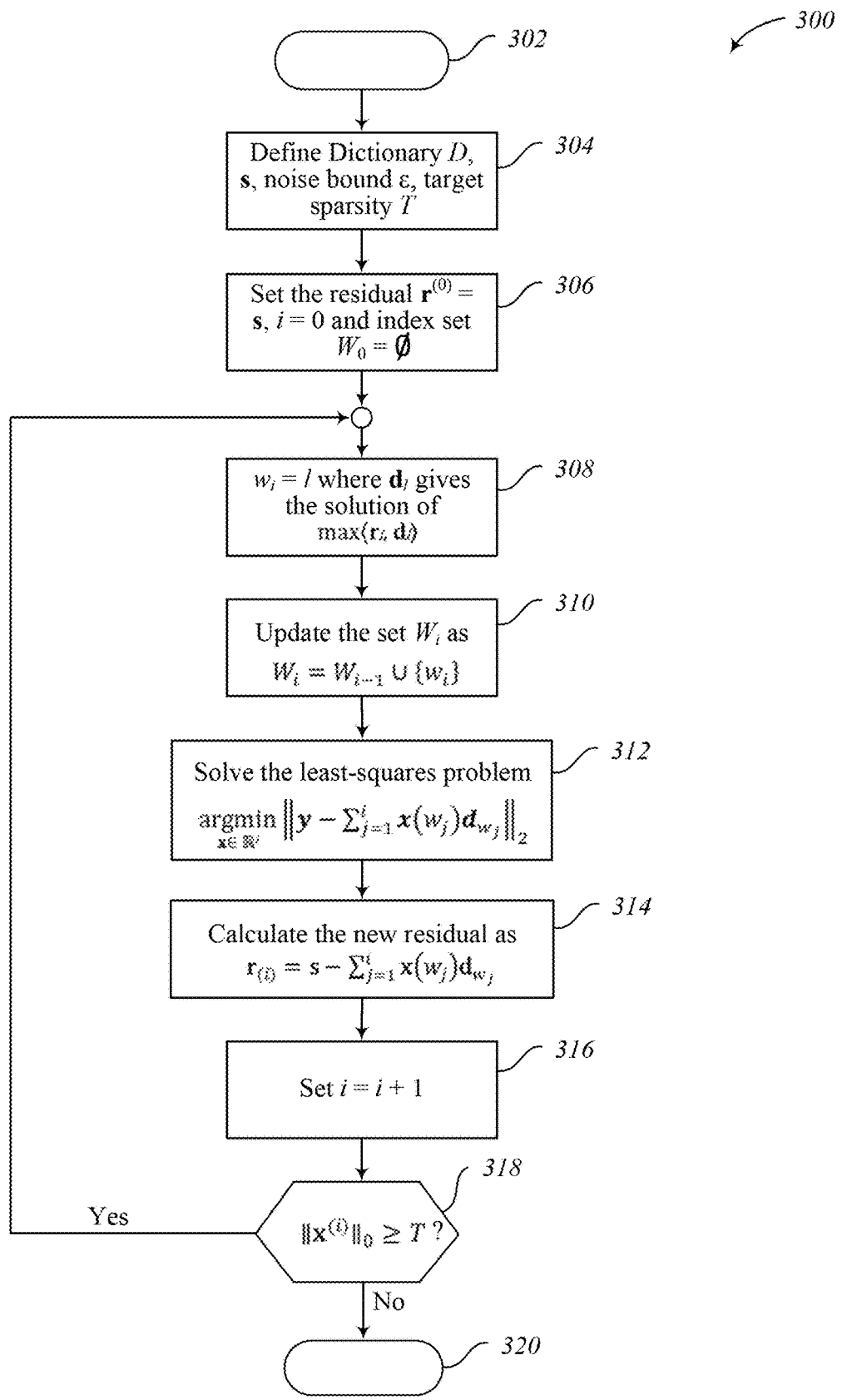
FIG. 3 illustrates an embodiment of a method of applying an OMP algorithm.

FIG. 3 illustrates an embodiment of a method 300 of applying an OMP algorithm. The method starts at 302 and proceeds to 304. At 304, a dictionary D, the data vector to be approximated s, optionally a noise bound ε, and a target sparsity T are defined, for example by retrieving, receiving or generating the dictionary D, the data vector s, the noise bound ε, and/or the target sparsity T. The noise boundary ε sets a limit such that x s.t. $\|Dx-s\|_2 \leq \epsilon$. The target sparsity T sets the condition $\|x\|_0 \leq T$. The method proceeds from 304 to 306.

At 306, the method 300 sets the residual $r^{(0)}=s$, index $i=0$ and index set $W_0=\emptyset$. The method proceeds from 306 to 308. At 308, $w_i$ is defined as $w_i=1$ where $d_l$ gives the solution of $\max\langle r_i, d\rangle$. The method proceeds from 308 to 310. At 310, the set $W_i$ is updated as $W_i=W_{i-1} \cup \{w_i\}$. The method proceeds from 310 to 312. At 312, the least-squares problem $$\operatorname*{argmin}_{x \in \mathbb{R}} \left\| y - \sum_{j=1}^{i} x(w_j) d_{w_j} \right\|_2$$

is solved. The method proceeds from 312 to 314. At 314, the new residual is calculated as $r_{(i)}=s-\Sigma_{j=1}^{i} x(w_j)d_{w_j}$. The method proceeds to 316. At 316, the index i is incremented. The method proceeds from 316 to 318. At 318, the method determines whether the iterations should terminate. As illustrated, this is done by determining whether $\|x^{(i)}\|_0 \geq T$. When it is determined at 318 that $\|x^{(i)}\|_0 \geq T$, the method 300 returns to 308 for the next iteration. When it is not determined at 318 that $\|x^{(i)}\|_0 \geq T$, the method proceeds from 318 to 320, where the iterations are terminated and the current residual vector is output. Embodiments of the method 300 may perform additional acts, may perform fewer acts, may modify performed acts, and may perform acts in orders other than as illustrated. For example, the method may be modified to determine at 318 whether $\|r^{(i)}\|_2 \leq 2$ or $\|x^{(i)}\|_0 \geq T$, and the decision as to whether another iteration is to be performed may be made based on this determination.

An embodiment of another OMP algorithm is set forth in Table 1, below.

TABLE 1

Example OMP Algorithm

Algorithm 1 OMP

Require: Dictionary D, S, target sparsity T
Ensure: x s.t. $\|Dx - s\|_2 \leq \epsilon$ and $\|x\|_0 \leq T$
  1: Set the residual $r^{(0)} = s$, $i = 0$ and index set $W_0 = \emptyset$;
  2: while $\|x^{(i)}\|_0 \geq T$ do
  3:    Let $w_i = 1$ where $d_l$ gives the solution of $\max\langle r_i, d_l\rangle$
  4:    Update the set $W_i$ as $W_i = W_{i-1} \cup \{w_i\}$
  5:

$$\text{Solve the least-squares problem } \operatorname*{argmin}_{x \in \mathbb{R}^i} \left\| y - \sum_{j=1}^{i} x(w_j) d_{w_j} \right\|_2$$

6:    Calculate the new residual as $r^{(i)} = s - \Sigma_{j=1}^{i} x(w_j)d_{w_j}$
  7:    Set $i = i + 1$
  8: end while In an embodiment, the detection of anomalies is based on the analysis of single beats. Beats are extracted from ECG recordings. A heart beat extracted may be denoted by $s \in \mathbb{R}^M$. In an embodiment, a training set of normal beats acquired in normal sensing conditions is provided. For simplicity, an embodiment employing supervised training will be considered first, where labeled training data belonging to the normal class are available (an even easier situation would occur when both normal and abnormal samples are provided). An embodiment employing unsupervised training, where labels for the training data are not provided, will then be discussed.

It is assumed that a normal test beat s may be well approximated as $$s \approx Dx \quad (6)$$

where D is an unknown dictionary and the coefficients vector x is sparse. The following explains an example of how to compute the dictionary D and the coefficient vector x together with the proposed anomaly detector, namely dictionary learning and anomaly detection, of an embodiment.

In an embodiment, a database of training samples $\{s_i\}_{i=1}^n$ belonging to a normal class is given. The training signals are assumed to have been generated as $s_i = Dx_i + e_i$, where $D=[d_1] \ldots [d_N] \in \mathbb{R}^{M \times N}$ is a fixed but unknown dictionary, $x_i \in \mathbb{R}^N$ is T-sparse ($\|x\|_0 \leq T$) for $i=1, \ldots, n$, with T a fixed known value, and $e_i \in \mathbb{R}^M$ is a random perturbation noise with bounded power $\|e_i\|_2 \leq \epsilon$ for $i=1, \ldots, n$. The dictionary D which gives the best T-sparse representation of the given training samples $\{s_i\}_{i=1}^n$ and the sparse representations $\{x_i\}_{i=1}^n$ are determined. The matrices obtained by concatenating column-wise the vectors $s_i$ and $x_i$ respectively may be denoted by $S=[s_1, \ldots, s_n] \in \mathbb{R}^{M \times n}$ and $X=[x_1 | \ldots | x_n] \in \mathbb{R}^{N \times n}$. A suitable minimization problem of an embodiment may be represented as:

$$\operatorname*{argmin}_{D,\{x_i\}_{i=1}^n} \|Dx - S\|_F^2 \text{ s.t. } \|x_i\|_0 \leq T \text{ for } i = 1, \ldots, n \quad (7)$$

$$\|d_j\|_2 = 1 \text{ for } j = 1, \ldots, N$$

where F denotes the Frobenius norm. The condition $\|x_i\|_0 \leq T$ contrains the sparsity of the representation in each vector in the training set, while $\|d_j\|_2=1$ is a constraint on the norm of each column of the dictionary D which avoids trivial solutions. Note that this formulation is a matrix version of Equation (5) where D is unknown. This joint optimization problem can be solved using a K-SVD algorithm. See Aharon, et al., *Svd: An algorithm for designing overcomplete dictionaries for sparse representation*, Signal Processing, IEEE Transactions on, vol. 54, No. 11, pp. 4311-4322, 2006. An illustrative example of a learned sparse model is shown in FIG. 4.

K-SVD is an iterative algorithm which addresses a problem (such as the problem of equation 7) by alternating minimization over D and X. K-SVD starts with a fixed number of iterations and an initial dictionary $D^{(0)}$ (such as a dictionary with totally random entries or a dictionary having a randomly chosen subset of the training vectors). The general iteration alternates between optimizing the coefficients X and the dictionary D. The coefficients are first computed, for example using an OMP algorithm, and then a dictionary update is performed jointly with an update of the coefficients. The joint dictionary and coefficient update comprises an iteration over each atom in the dictionary, jointly updating that atom and the corresponding coefficient elements. For each dictionary atom $d_l$, for l=1, . . . , N, the residual error is defined $$E_l = S - DX + d_l x_l^T \quad (8)$$

where $x_l^T$ is the row l of X. The residual error assesses the dictionary performance taking aside the contribution of the selected atom. Then the optimum values of $d_l$ and $x_l^T$ can be computed as $$\operatorname*{argmin}_{d,x} \|E_l - dx^T\|_F^2 \text{ s.t. } \|d\|_2 = 1 \quad (9)$$

Since $dx^T$ has rank 1, the minimizers of the problem (e.g., the problem of equation 9) can be found as the optimum rank-1 approximation of $E_l$ using SVD. Given $E - L = U \Sigma V^T$ the SVD of $E_l$, d and x may be set as $d = u_1$ and $x = \sigma_1 v_1$. Note that this update will not usually give a sparse x, thus the columns of X will not be sparse in general. This may be addressed by defining $\hat{E}_l$ as the restriction of $E_l$ to those columns for which the corresponding entries in $x_l^T$ are non-zero, and applying the same process to $\hat{E}_l$.

Figure 5:
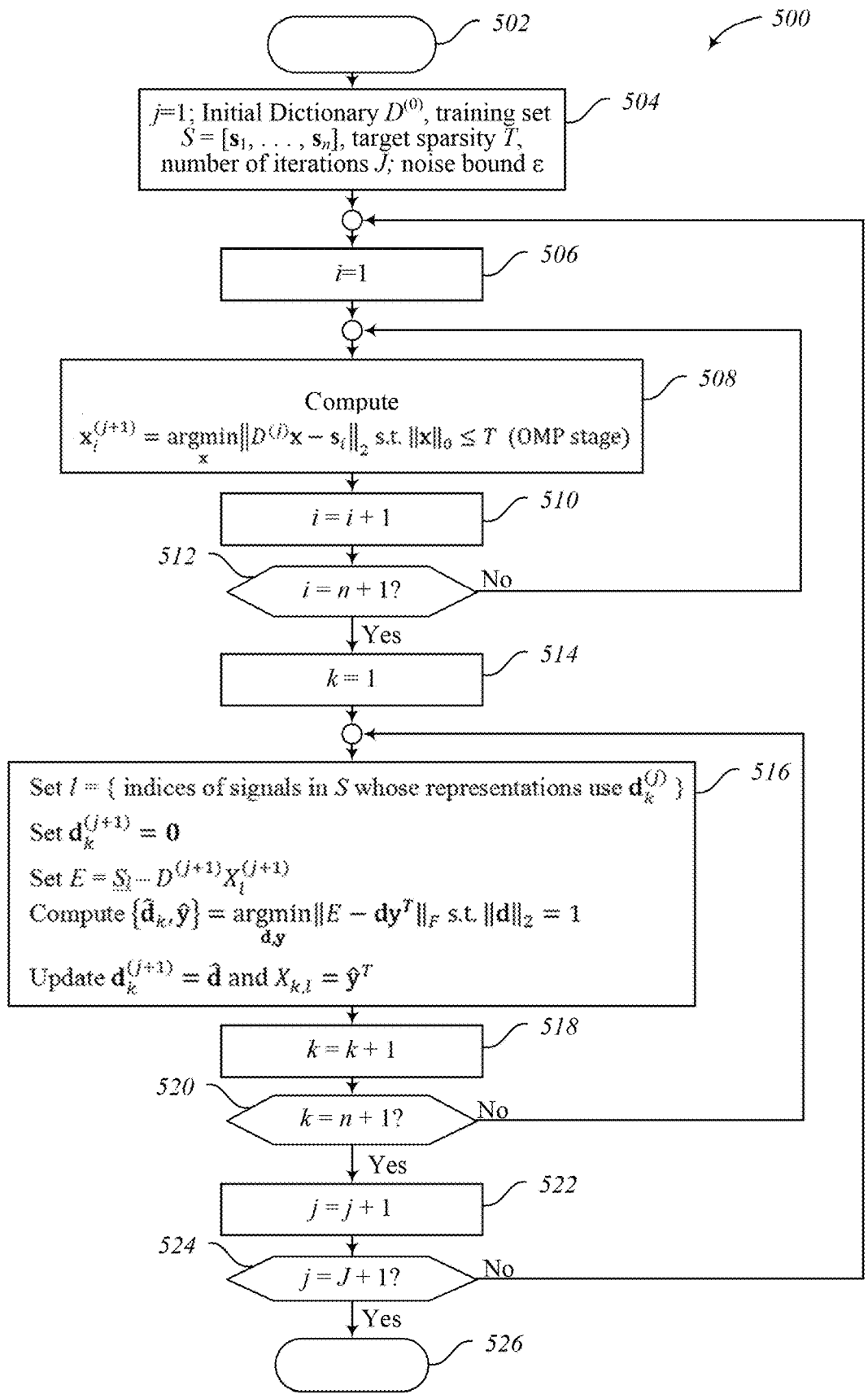
FIG. 5 illustrates an embodiment of a method of applying a K-SVD algorithm to generate a dictionary.

An embodiment of a method 500 of applying a K-SVD algorithm to define a dictionary D is illustrated in FIG. 5. The method 500 starts at 502 and proceeds to 504. At 504, an initial dictionary $D^{(0)}$, a training set $S = [s_1, \ldots, s_n]$, a target sparsity T, a number of iterations J, and a noise bound E are defined, for example by retrieving, receiving or generating the dictionary D, the training set S, the noise bound ε, the target sparsity T and or the number of iterations J. The method proceeds from 504 to 506.

At 506, an index i for an OMP algorithm is initialized and the method proceeds to 508. At 508, the method 500 determines coefficients of vectors of the matrix X using, for example, an OMP algorithm. As illustrated, $$x_i^{(j+1)} = \operatorname*{argmin}_{x} \|D^{(j)} x - s_i\|_2 \text{ s.t. } \|x\|_0 \le T$$

is computed for an ith vector in the matrix X and the method proceeds from 508 to 510 where the index i is incremented. The method 500 proceeds to 512 where it is determined whether all of the vectors of the matrix X have been processed, as illustrated this is done by determining whether i=n+1. When it is determined at 512 that not all of the vectors of the matrix X have been processed, the method proceeds from 512 to 508 to process the next vector. When it is determined at 512 that all of the vectors of the matrix X have been processed, the method proceeds from 512 to 514.

At 514, an index k for optimizing the dictionary D and the coefficients X is initialized and the method 500 proceeds to 516. At 516, the method 500 optimizes the dictionary D and the coefficients X. As illustrated, this includes setting l equal to the indices of signals in S whose representations use $d_k^{(j)}$; setting $d_k^{(j+1)} = 0$; setting $E = S_l - D^{(j+1)} X_l^{(j+1)}$; computing $$\{\hat{d}_k, \hat{y}\} = \operatorname*{argmin}_{d,y} \|E - dy^T\|_F \text{ s.t. } \|d\|_2 = 1;$$

and updating $d_k^{(j+1)} = \hat{d}$ and $X_{k,l} = \hat{y}^T$. The method 500 proceeds to 518, where the index k is incremented. The method proceeds to 520 where it is determined whether all of the vectors of the dictionary D have been processed, as illustrated this is done by determining whether k=n+1. When it is determined at 520 that not all of the vectors of the dictionary D and of the matrix X have been processed, the method proceeds from 520 to 516 to process the next vector. When it is determined at 520 that all of the vectors of the dictionary D and the matrix X have been processed, the method proceeds from 520 to 522.

At 522, the method 500 increments the index j and proceeds to 524. At 524 the method 500 determines whether the desired number of iterations has occurred, as illustrated this is done by determining whether j=J+1. When it is determined at 524 that more iterations are desired, the method proceeds from 524 to 506 to start the next iteration. When it is determined at 524 that the desired number of iterations have been completed, the method proceeds from 524 to 526, where the dictionary $D^{(J)}$ and the coefficient matrix X are output. Embodiments of the method 500 may perform additional acts, may perform fewer acts, may modified acts, and may perform acts in orders other than as illustrated.

An embodiment of another K-SVD algorithm is set forth in Table 2, below.

TABLE 2

Example K-SVD Algorithm

Algorithm 2 K-SVD

Require: Initial dictionary $D^{(0)}$, training set S = [$s_1$, . . . , $s_0$], target sparity T, number of iterations J
Ensure: Dictionary D = $D^{(J)}$, coefficient matrix X s.t. $\|X - S\|_F^2$ and $\|x_i\|_0 \le$ T for i = 1, . . . , n
  1: while j < J do
  2:   for i = 1, . . . , n do
  3:
      Compute $x_j^{(j+1)} = \operatorname*{argmin}_{x} \|D^{(j)} x - s_i\|_2$ s.t. $\|x\|_0 \le$ T (OMP stage)
  4:   end for
  5:   for l = 1, . . . , N do
  6:     Set l = {indices of signals in S whose representations use $d_l^{(j)}$}

TABLE 2-continued

Example K-SVD Algorithm

Algorithm 2 K-SVD

7:  Set $d_l^{(j+1)} = 0$
8:  Set $E = S_l - D^{(j+1)}X_l^{(j+1)}$
9:  Compute $\{\hat{d}_l, \hat{y}\} = \underset{d,y}{\operatorname{argmin}} \|E - dy^T\|_F$  s.t.  $\|d\|_2 = 1$
10: Update $d_l^{(j+1)} = \hat{d}$ and $X_{l,I_l} = \hat{y}^T$
11: end for
12: Set $j = j + 1$
13: end while Observe that optimization problems (such as the problem of equation 9 above) can also be interpreted terms of matrix factorizations. The problem of discovering an underlying dictionary may be viewed as the same as the problem of discovering a factorization of the matrix S as DX where D and X have the indicated sizes, and X has sparse columns. This matrix factorization viewpoint connects this problem with related problems of nonnegative matrix factorization and in particular, sparse nonnegative matrix factorization.

Assume now that a test signal $s \in \mathbb{R}^M$ is given. The sparse coding of s with respect to the learned dictionary D corresponds to computing a vector x of coefficients that is expected to be T-sparse. This problem can be formulated as an instance of the $\mathcal{P}_0^T$ problem and can be computed, for example, by using an embodiment of the method 300 of FIG. 3 or an embodiment of the algorithm of Table 1.

The T-sparse approximation x of a test signal s can be used as a tool to measure the extent to which the signal s is normal or anomalous. To quantitatively assess how close a test signal is to the normal ones, anomaly indicators may be used that measure the degree to which a sparse approximation is accurate. When approximating anomalous signals by linear combinations of a few atoms of D, a substantial deviation in the reconstruction error may be expected since atoms of D were learned to represent normal data. To this purpose, a viable anomaly indicator in an embodiment would be the root-mean-square error (RMSE):

$$RMSE_{(D,T)}(s) := \frac{\|Dx - s\|_2}{\sqrt{M}}. \quad (10)$$

This anomaly indicator can be considered to map from $\mathbb{R}^M$ (the space of signals) into a low-dimensional feature space ($\mathbb{R}$ in this case), where features from normal signals follow an unknown distribution. Signals yielding unusual values of this indicator can be considered anomalies. One of the most straightforward solutions to detect anomalies comprises building a suitable confidence region and considering anomalous the signals s yielding $RMSE_{(D,T)}(s)$ falling outside of this region. In an embodiment, the scalar anomaly indicator, may be $$I_\alpha = [0, q_\alpha] \quad (11)$$

where $q_\alpha$ denotes the $\alpha$-quantile of the empirical distribution of the RMSE (9). In particular, s may be considered anomalous if $RMSE_{(D,T)}(s) \notin I_\alpha$ or equivalently $RMSE_{(D,T)}(s) > q_\alpha$.

In an embodiment, the interquartile range $$IQR := q_{\frac{3}{4}} - q_{\frac{1}{4}}$$

may be considered and the confidence region defined as $$I_\rho = \left[0, q_{\frac{3}{4}} + \rho IQR\right]. \quad (12)$$

In this case s may be considered anomalous if $$RMSE_{(D,T)}(s) > q_{\frac{3}{4}} + \rho IQR.$$

Figure 6:
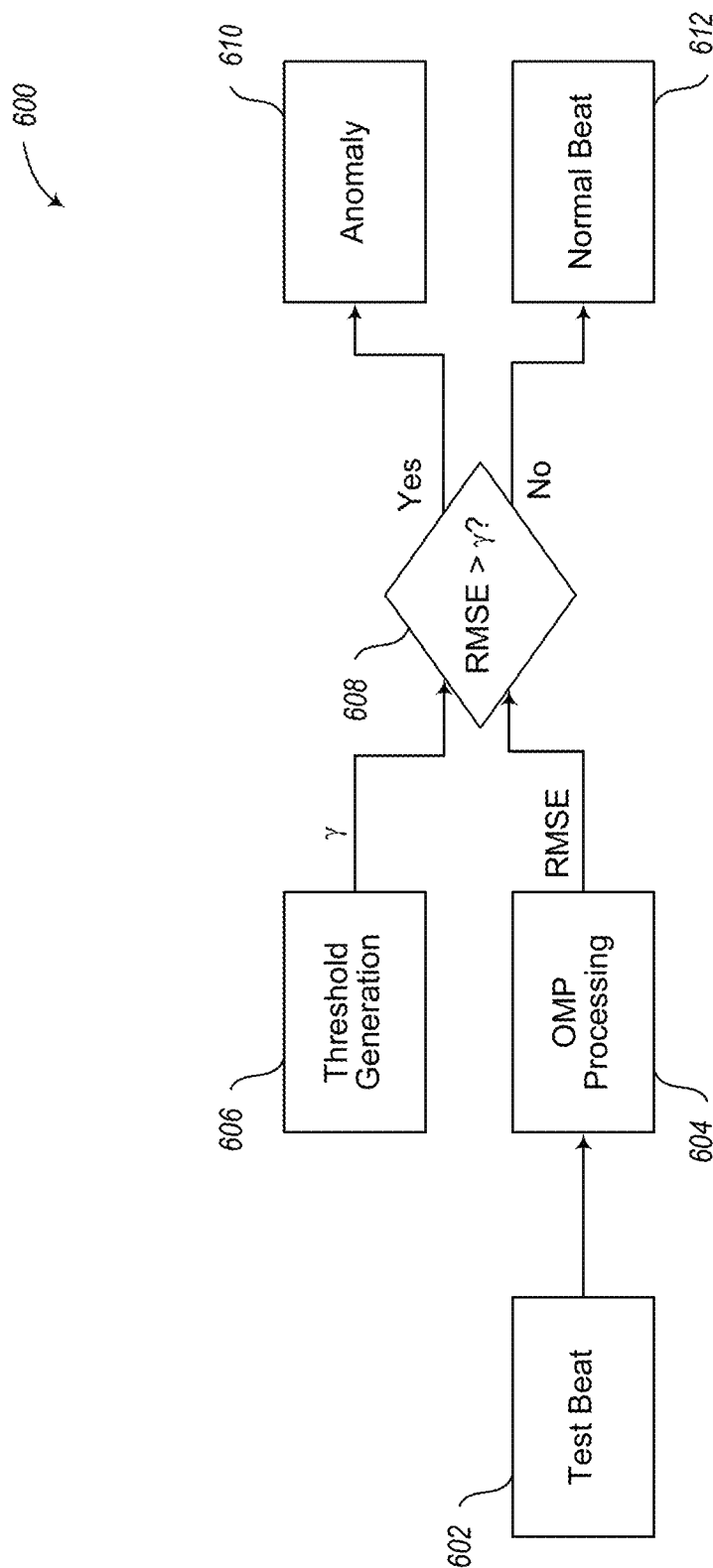
FIG. 6 illustrates an embodiment of a method of detecting an anomalous heartbeat.

An illustration of an example pipeline method 600 is depicted in FIG. 6. At 602, a test signal s is obtained or provided which includes heart beat information. The signal is subjected to OMP processing (see, e.g., method 300 of FIG. 3) at 604 to produce an indication of a root-mean-square-error RMSE. At 606, a threshold $\gamma$ is determined based on the defined confidence region (e.g., $\gamma$ represents $q_\alpha$ or $q_{3/4}$+pIQR in the examples discussed above). The RMSE error and the threshold $\gamma$ are compared at 608 to determine whether the RMSE error is greater than the threshold $\gamma$. When it is determined that the RMSE error is greater than the threshold at 608, the method 600 proceeds to 610 to perform processing consistent with a detected anomaly, such as initiating transmission of data indicating an anomaly in an embodiment, proceeding to process the next beat, etc. When it is not determined that the RMSE error is greater than the threshold at 608, the method proceeds to 612 to perform processing consistent with a normal beat, such as not initiating a transmission of data in an embodiment and processing the next beat, etc. Other indications of the reconstruction error may be employed in an embodiment.

Figure 7:
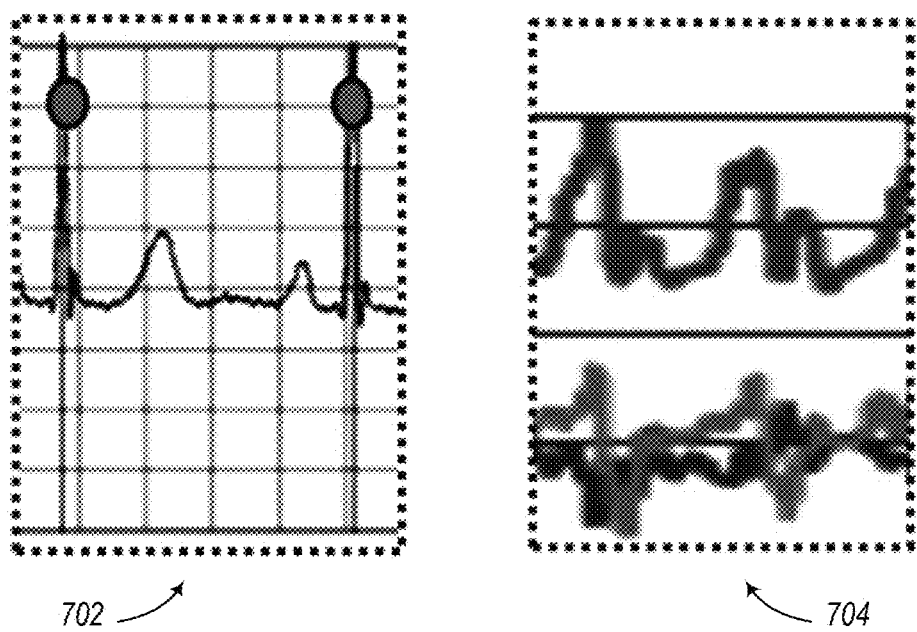
FIG. 7 is a graphical illustration of heart beats and acceleration data.

As mentioned above, a user state may be characterized by a heart rate HR and a measured energy of acceleration EE. FIG. 7 graphically represents heart beats 702 from which a heart rate may be measured and corresponding acceleration data 704 from which an energy of acceleration may be determined. During everyday activities, both the heart rate and the morphology of the beats of a user may be expected to change in response to changes in a user state. An embodiment may automatically adjust to compensate for changing user states. To facilitate adaptability to such changes, the current user's state may be characterized by the heart rate (HR) and the corresponding measured energy of the acceleration (EE). The heart rate may be measured in terms of beats in a unit of time, such as a number of contractions of the heart per minute (bpm). The current heart rate can be computed by considering fixed-size windows of, for example, 10 seconds each, and, for each window computing a robust statistic of the punctual heart rates of the beats in the window (discussed in more detail elsewhere herein). The energy of the acceleration may be defined as the $l_2$ norm of the accelerometer data corresponding to the current beat.

Figure 8:
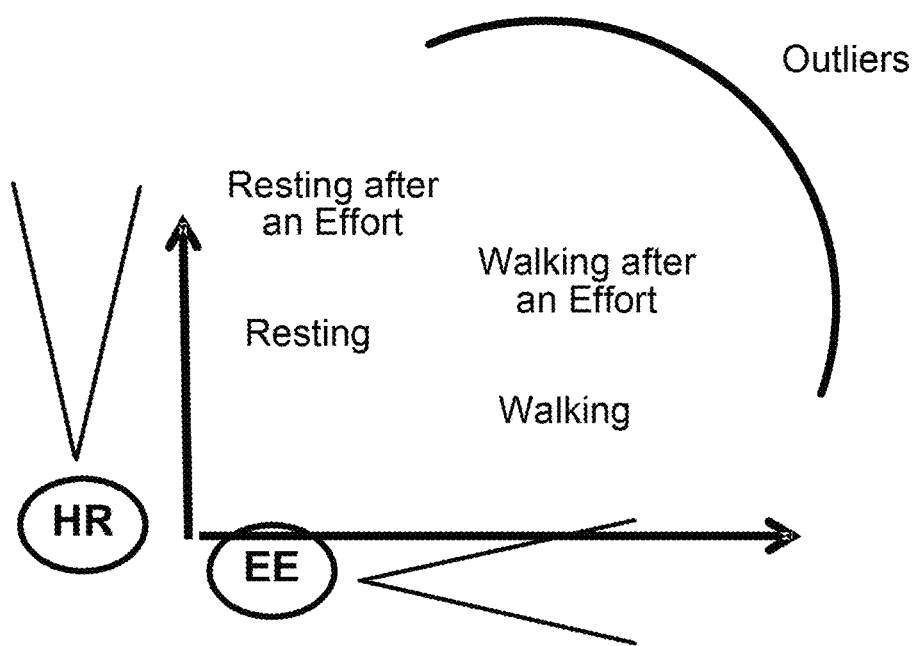
FIG. 8 is a graphical representation of an example relationship between user states and heart rate and measured energy of acceleration.

Combining these two features facilitates covering several states (e.g. Resting, Walking, Sleeping, Resting after an Effort, Walking after an Effort), as well as identifying outlier beats with respect to the combination, as depicted in FIG. 8. Observe that rather than being viewed as an exercise in classifying the user's state, the process may be viewed as delineating the feature space (HR; EE). For example, each pair of values (HR; EE) may be associated with a corresponding pair of transformations P(HR; EE) and F(HR; EE) to be applied to the beat s and the dictionary D in order to be adapted to the corresponding state. For example, $s_A$=P (HR; EE)(s) and $D_A$=P(HR; EE)·F(HR; EE)(D), where $s_A$ and $D_A$ represent the adapted beat and dictionary respectively. For simplicity, the composition P(HR; EE)·F(HR; EE) may be denoted G(HR, EE). P(HR; EE) may be considered a beat transform and G(HR, EE) may be considered a dictionary transform.

In an embodiment, the transformations P and F may be generic, e.g., they do not depend from the specific user. For example, the transformations may be learned by using several users as a training set. The transformations may be used to keep the reconstruction error (respectively before and after the adaptation) substantially unchanged as the user state changes. In this way the detector may be made substantially invariant with respect to changes in the user's state. Such transformations may be generated offline via, for example, statistical analysis such as Procrustes Analysis, Transfer Learning, Dynamic Time Warping, etc.

Figure 9:
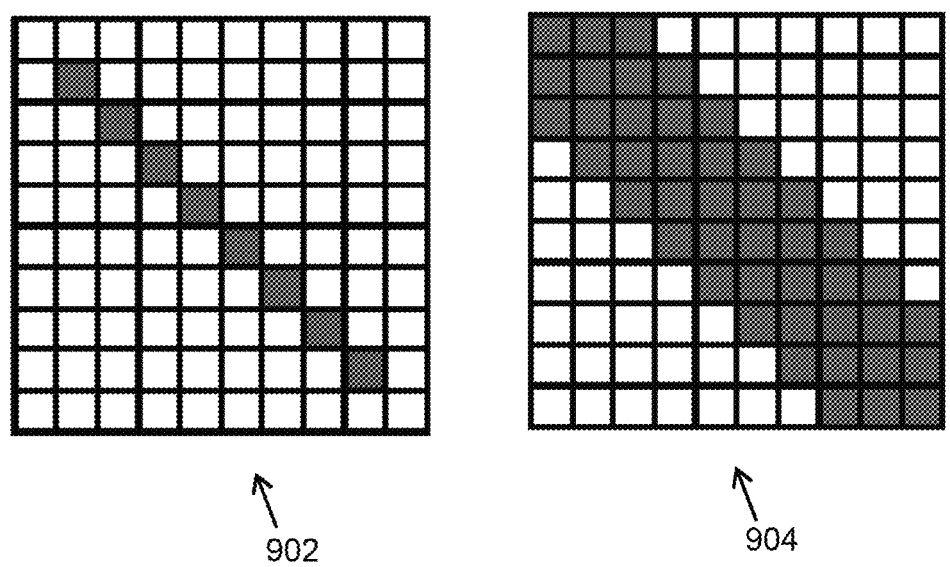
FIG. 9 is a graphical representation of an example pair of transforms applied to measured beats and to a dictionary to account for changes in user state in an embodiment.

FIG. 8 graphically represents example user states (as illustrated, resting, walking, sleeping, resting after an effort, walking after an effort) and an example relationship between the user states and heart rate HR and measured energy of acceleration EE. As discussed above, transforms to account for the user state may be defined and employed. FIG. 9 illustrates an example pair of transforms P(HR, EE) 902 and F(HR, EE) 904 to be applied to the measured beats and to the dictionary to account for changes in user state. Example transforms and the application thereof are discussed in more detail elsewhere herein. Other user states and relationships may be defined and employed.

Figure 10:
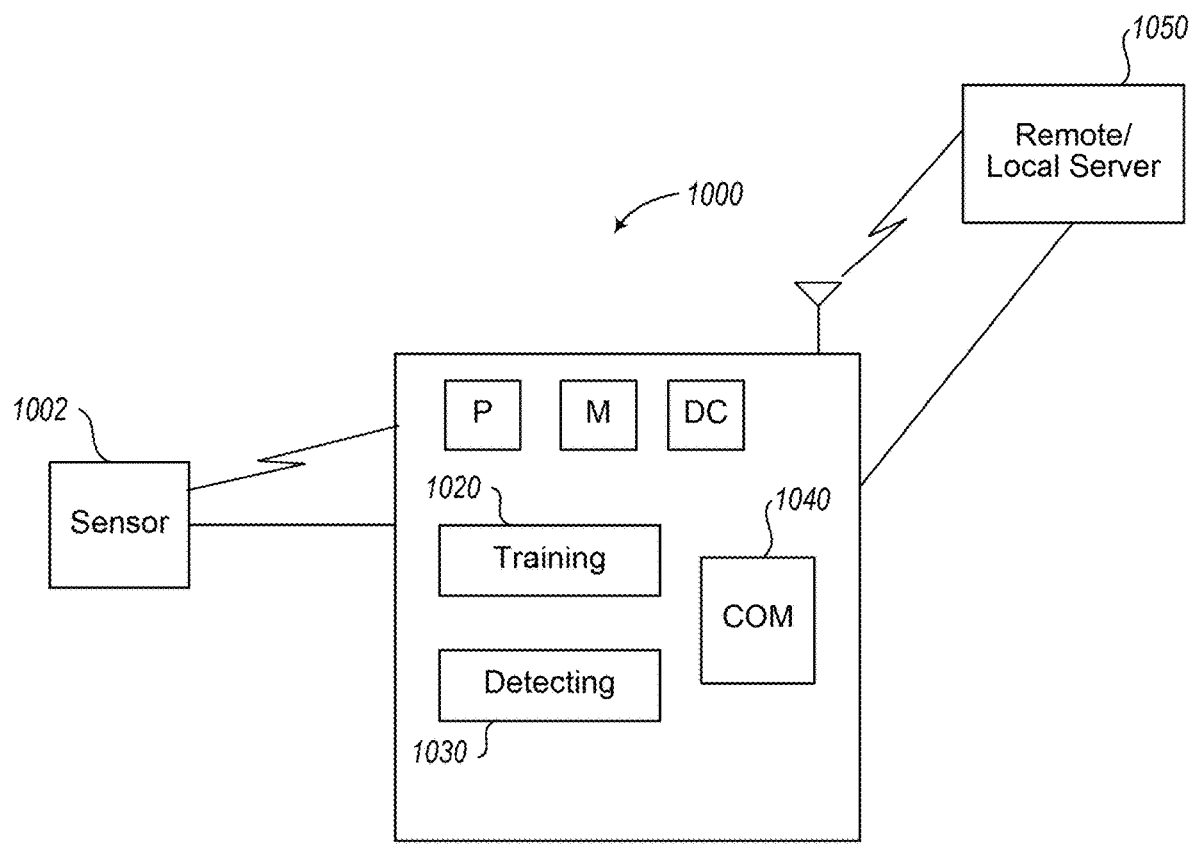
FIG. 10 illustrates an embodiment of a system for detecting abnormal heart beats.

FIG. 10 illustrates an embodiment of a system 1000 for detecting abnormal heart beats. The system 1000 as illustrated comprises one or more processors P, one or more memories M and discrete circuitry DC, which, alone or in various combinations, are configured to provide the functionality and/or implement the circuitry of the system 1000. As illustrated, the system 1000 is communicatively coupled (e.g., wired or wirelessly coupled) to one or more sensors 1002 which provide data, such as ECG traces and accelerometer data, to the system 1000. In some embodiments, one or more sensors may be integrated into the system 1000. The system 1000 includes a training circuit or module 1020, which, in operation trains a dictionary using, for example, an embodiment of one of the methods discussed herein. The system 1000 includes a detecting circuit or module 1030, which, in operation, detects anomalous heart beats using a trained dictionary and an embodiment of one the methods discussed herein. As illustrated, the system 1000 also is communicatively coupled (e.g., wired or wirelessly coupled) to one or more remote or local servers 1050, such as a local host (e.g., a cell phone, mobile device, etc.) and a local or remote server providing patient monitoring functionality. In some embodiments, the system 1000 may be communicatively coupled to a local host (e.g., a cell phone) which is in turn communicatively coupled to a remote server (e.g., a health monitoring server). The system 1000 includes a communication circuit or module 1040, which, in operation, controls communications between the system 1000 and other devices, such as sensors 1002 and remote/local servers 1050.

Figure 11:
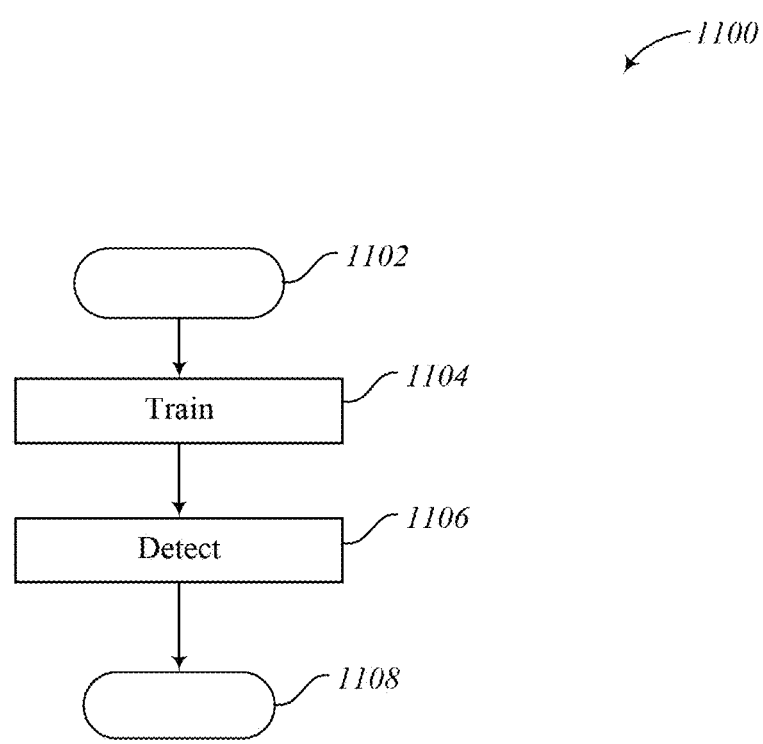
FIG. 11 illustrates an embodiment of a method of detecting abnormal heart beats.

FIG. 11 illustrates an embodiment of a method of detecting abnormal heart beats that may be employed, for example, by an embodiment of the system 1000 of FIG. 10. For convenience, FIG. 11 will be discussed with reference to system 1000 of FIG. 10. The method 1100 begins at 1102 and proceeds to 1104. At 1104, data (which may be real-time data or stored data), such as an ECG trace and optionally accelerometer data, is used, for example by a training module, such as the training module 1020 of FIG. 10, to train a sparse model dictionary D, which may be stored, for example in the memory M of system 1000 of FIG. 10. The data may be live data received, for example, from a sensor such as the sensor 1002 of FIG. 10, or stored training data, such as data received from a server, such as the server 1050 of FIG. 10. The input may include, for example, an ECG trace of, for example, seven minutes or more. A trace of seven minutes would normally provide sufficient beats (e.g., 500 or more beats) to generate a sufficient training data set. In an embodiment, the training data set may be a data set for a user in a relative resting state during the training period.

The method 1100 proceeds from 1104 to 1106. At 1106, the sparse model dictionary trained at 1104 is used, for example by a detecting module such as the detecting module 1030 of system 1000 of FIG. 10, together with accelerometer data, to classify beats of a continuous ECG trace as normal or anomalous. The method 1100 proceeds from 1106 to 1108, where, as illustrated, the method terminates. The method 1100 may include additional acts not shown in FIG. 11, may not include all of the acts shown in FIG. 11, and may split the acts shown in FIG. 11 into multiple acts. For example, an embodiment may include an additional act of enabling or waking communication circuitry (such as communication circuit 1040 of FIG. 10) in response to detection of an anomalous heartbeat. This may facilitate saving system power by enabling the communication circuitry when a communication (such as an indication of the detection of the anomalous heart beat) is desirable.

Figure 12:
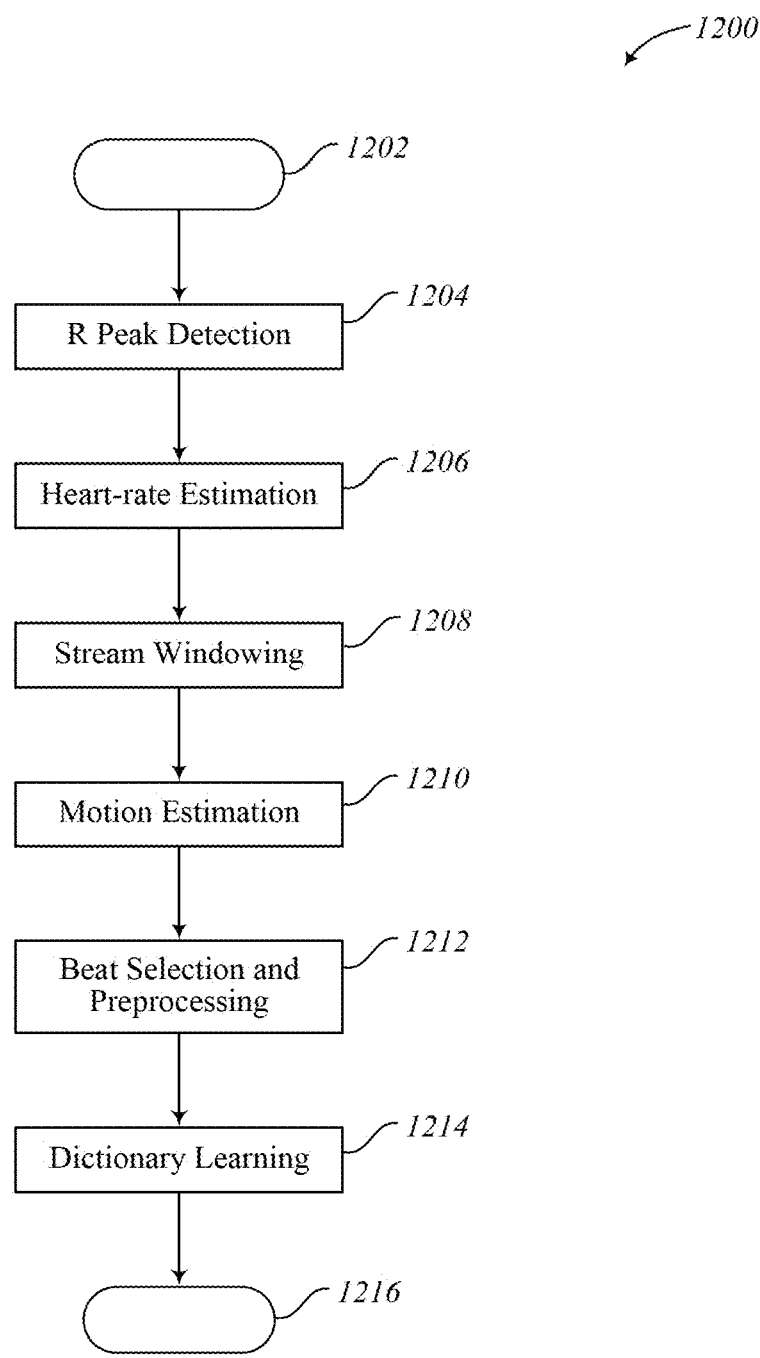
FIG. 12 illustrates an embodiment of a subroutine or method to generate a trained dictionary for detecting abnormal heart beats.
Figure 13:
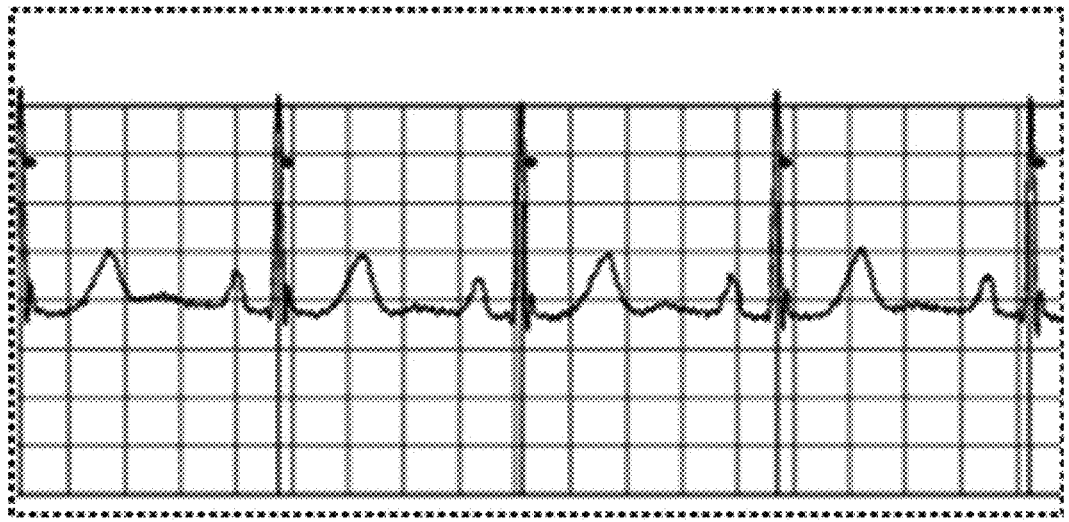
FIG. 13 is a graphical representation of a portion of an ECG trace.

FIG. 12 illustrates an embodiment of a training subroutine or method 1200 to train a dictionary for detecting abnormal heart beats, which may be employed, for example, by an embodiment of the method 1100 of FIG. 11 and/or by an embodiment of the system 1000 of FIG. 10. The training is based on analysis of individual beats, for example of individual beats in an ECG trace of a user. The training stage selects a proper training set of sample beats and generates a sparse dictionary D based on the training set of sample beats. FIG. 13 is a graphical representation of a portion of an ECG trace or stream that may be input to the training subroutine or method 1200. The input of this stage may be an ECG stream of a time length of, for example, around seven minutes, which may provide around 500 beats, with the user in a relative resting condition, and accelerometer data. The output is a dictionary D associated to a fixed sparsity level T.

Although a cardiac cycle starts at the beginning with a P-wave, an embodiment does not need to be precise in isolating a heartbeat. Instead, portions of tracing that are expected to repeat along the time and to conform to each other may be selected. In an embodiment, the R-peaks as used as reference points for the repetitive phenomenon and a fixed window is selected around the R-peak. In the discussion, heartbeats, or simply beats, refers to such collections of samples inside the window. Also, an embodiment may employ preprocessing and filtering steps to analyze the signal.

The method 1200 proceeds from 1202 to 1204, for example in response to calling of the training subroutine.

At 1204, the R-peaks of each heart beat are detected. This may be done, for example, by filtering the ECG traces, for example using two median filters, to remove the baseline, and detecting the R-peaks in the filtered signal using, for example, a Pan-Tompkins algorithm. See Pan, et al., *A real-time qrs detection* algorithm, Biomedical Engineering, IEEE Transaction on, No. 3, pp 230-236, 1985. The R-peaks are used as reference points for the heartbeats. The method 1200 proceeds from 1204 to 1206.

At 1206, heart rates are estimated. For example, a punctual heart rate (RR) and a reference heart rate (RHR) may be estimated. The heart rate is a number of contractions of the heart per minute, e.g., beats per minute. The punctual heart rate may be measured, for example, by dividing 60 by the time difference in seconds between an R-peak of a beat and an R-peak of an adjacent beat. The reference heart rate may be considered as a reference heart rate for a particular user in resting conditions, and may be determined, for example, based on a statistical analysis of the punctual heart rates of the trace. For example, the RHR may be set to the median of the punctual heart rates. An embodiment may identify inliers in the punctual heart rate, and exclude outliers. For example, inliers may be identified by determining whether individual punctual heart rates are within a threshold range of the reference heart rate of the trace (e.g., [RHR−5 bpm, RHR+5 bpm]). The method proceeds from 1206 to 1208.

Figure 15:
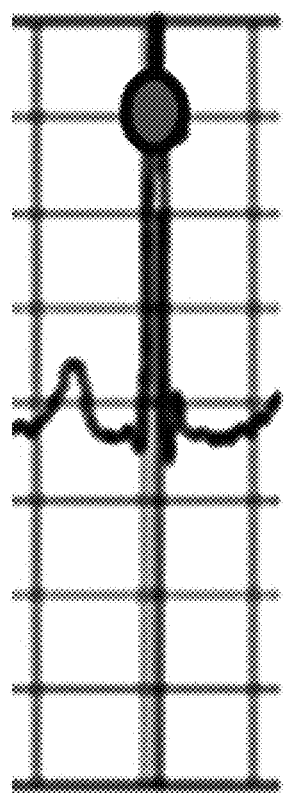
FIG. 15 is a graphical representation of a windowed beat of an ECG trace.

At 1208, the beats of the stream are windowed, for example using a reference window of a reference window size, which may be a fixed size, such as, for example, R−0.35 seconds, R+0.35 seconds. For each R-peak, a fixed-size window with a center located in the R-peak is extracted from the ECG stream. For example, one can consider windows of size 0:7 s (0:35 s around the R-peak). Observe that, since the RHR is expected to range from 60 to 100 bpm, a window of 0:7 s facilitates selecting all the PQRST waves of the current beat without including waves from the previous or subsequent beats. The chosen fixed-size window size may be referred to as a reference window size (RWS) and considered as the reference window for the particular user in resting conditions. At this level, heartbeats, or simply beats, refers to the collection of samples inside the chosen window. FIG. 15 is a graphical representation of an example of a windowed beat of an ECG trace. The method proceeds from 1208 to 1210.

Figure 14:
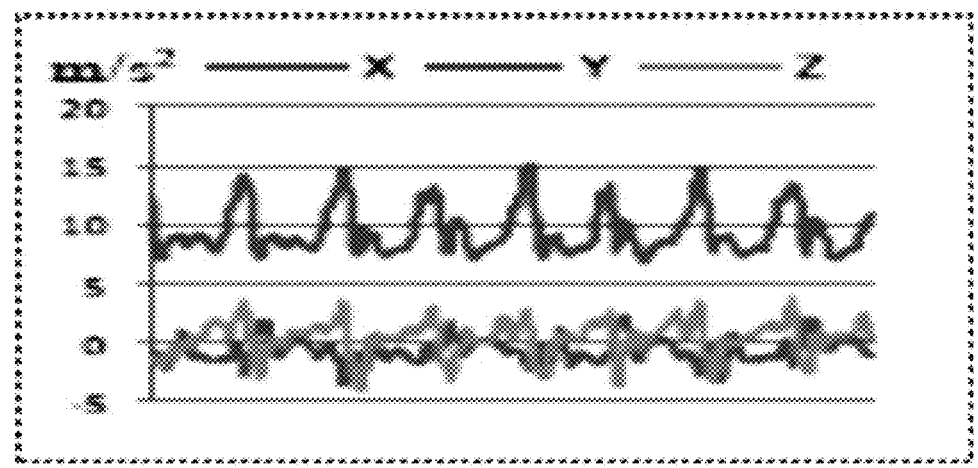
FIG. 14 is a graphical representation of accelerometer data.

At 1210, motion estimation is performed. In an embodiment, accelerometer data is provided as an input. The ECG data stream and the accelerometer data are synchronized or assumed to be synchronized. For each heartbeat the energy of the acceleration (EE) of the associated accelerometer data is measured. In an embodiment, the energy of the acceleration is defined as the $l_2$ norm of the accelerometer data corresponding to a window of size RWS around the R-peak. Outliers in the accelerometer data distribution may be identified, using, for example, confidence intervals based on sliding windows along the trace. See FIGS. 7-8 and the description thereof. FIG. 14 is a graphical representation of an example of accelerometer data. The method proceeds from 1210 to 1212.

At 1212, beats are selected to obtain a reliable training data set with an almost constant heart rate. This may be done by discarding beats identified as outliers at 1206 (RR outliers) or 1210 (beats associated with outlier accelerometer data, and/or beats inconsistent with a resting state), etc. With regard to the outlier beats with respect to the punctual heart rate RR, such beats may be excluded because the outlier status may be an indicator the beats are highly affected by noise or motion artifacts, or failures in the sensing process due, for example, in involuntary movements of the user. With regard to outlier beats with respect to the accelerometer data, such beats may similarly be excluded as likely to be affected by noise or motion artifacts. With regard to beats inconsistent with a resting state, such beats may be excluded from the data used for the training set and/or a high number of such beats may indicate the trace is not suitable for use in the training phase. In an embodiment, beats may be selected for the training phase which have inlier punctual heart rates and inlier accelerometer data. The selected beats may also be subjected to preprocessing at 1212, such as obtaining a zero-mean vectors by subtracting the mean (e.g., vertically translating the beats). The preprocessed selected beats form a training data set $s_i$, which may also be denoted:

$$TS=\{s_i\}_{i=1}^{n}$$

If the number of selected beats in the training data set is too low (e.g., less than a threshold number, such as 500 beats), additional beats may be analyzed and added to the training set. The method proceeds from 1212 to 1214.

At 1214, the dictionary is learned from the training data set $s_i$. This may be done, for example, using an embodiment of the method 500 of FIG. 5 and/or an embodiment of the K-SVD algorithm of Table 2. The method proceeds from 1214 to 1216, where the subroutine may return the dictionary D, further processing may occur, etc. For example, the dictionary D may be provided to an anomaly detection subroutine, as discussed elsewhere herein. Embodiments of the method 1200 may perform additional acts not shown in FIG. 12, may perform the acts of FIG. 12 in different orders, may omit acts shown in FIG. 12, and may combine or split acts shown in FIG. 12. For example, in an embodiment the method 1200 may be modified to check whether beat selection at 1212 indicates an ECG trace is unsuitable for use in generating a dictionary D, and when it is determined that an ECG trace is unsuitable, to collect another ECG trace to use for training the dictionary D.

Figure 16:
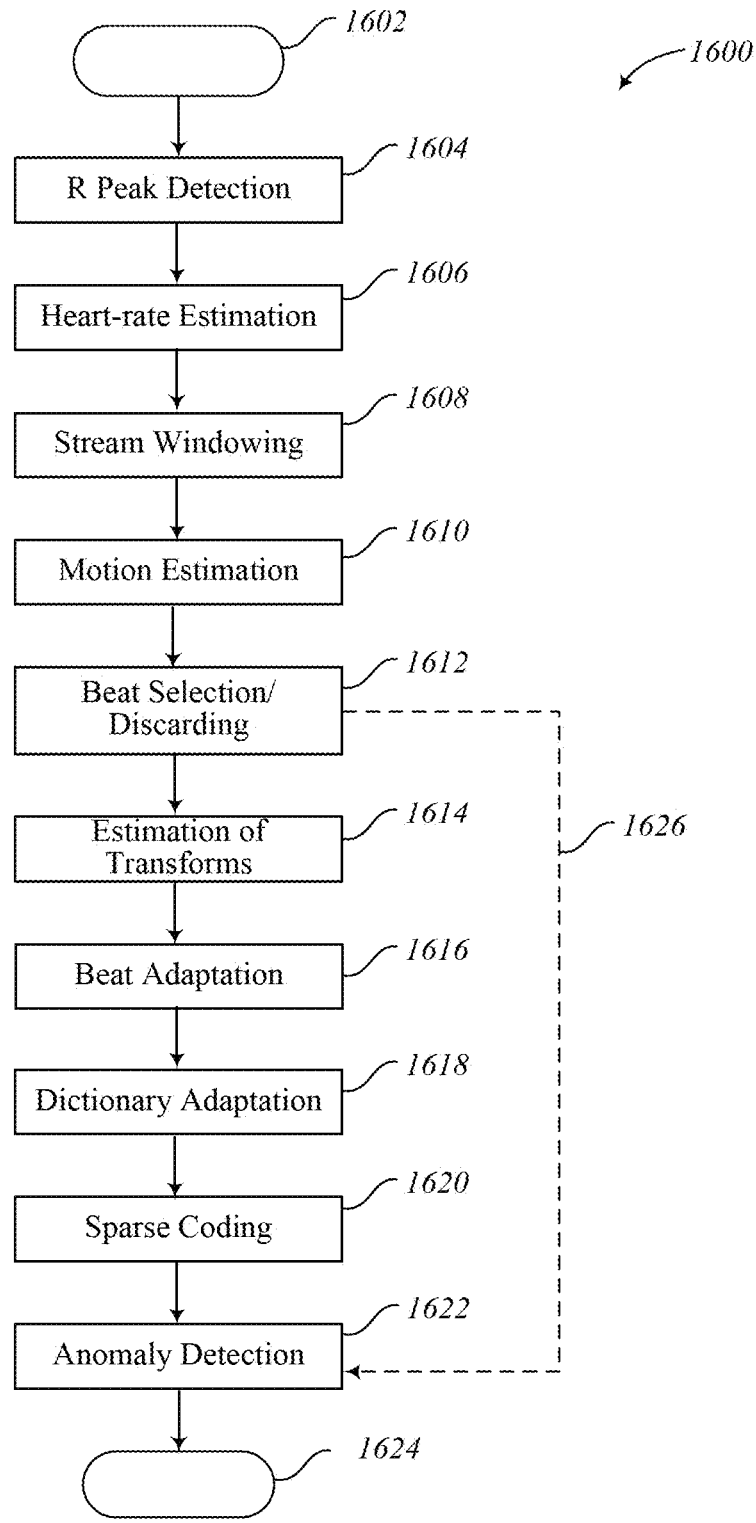
FIG. 16 illustrates an embodiment of a subroutine or method to detect abnormal heart beats using a trained dictionary, an ECG trace and accelerometer data.
Figure 17:
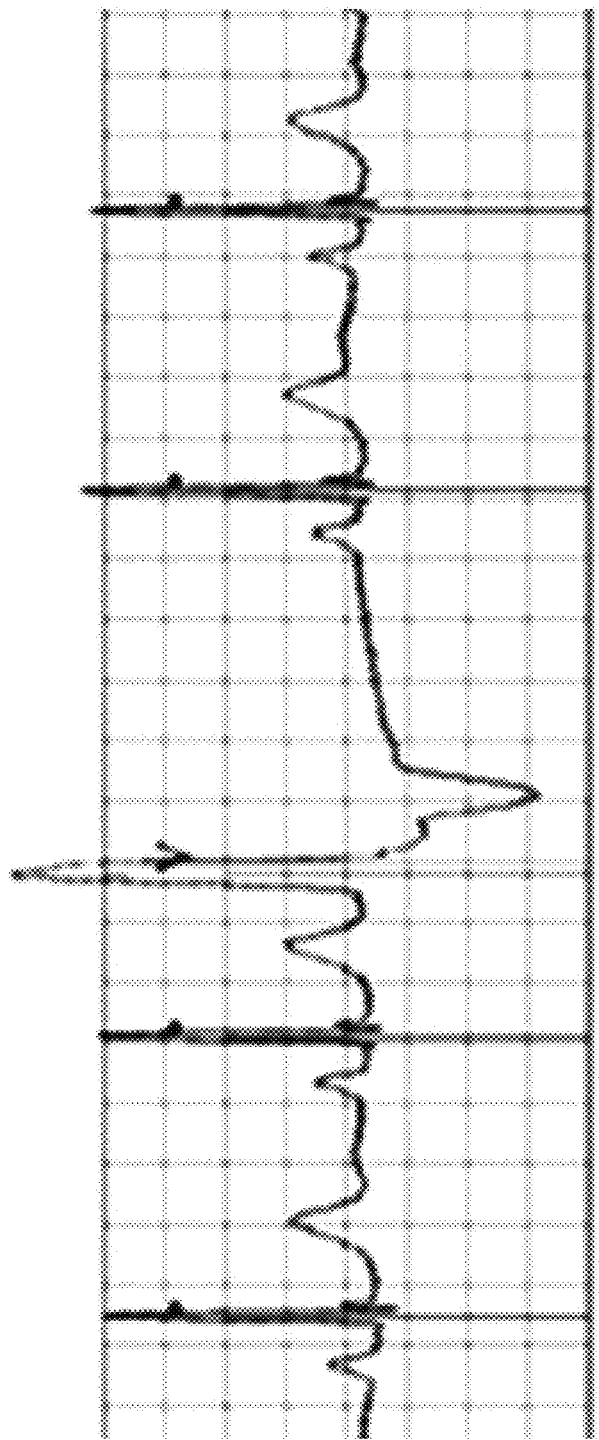
FIG. 17 is a graphical representation of an ECG trace.

FIG. 16 illustrates an embodiment of a subroutine or method 1600 to detect abnormal heart beats using, for example, a trained dictionary, a current ECG trace and accelerometer data. FIG. 17 is a graphical representation of an ECG trace that may be provided as input to the subroutine 1600. The method 1600 may be applied to individual beats, and may be applied sequentially to a series of individual beats, or in parallel to sets of individual beats. The output for each beat is an indication of whether the beat is normal or anomalous. The subroutine 1600 extracts single heartbeats from the continuous ECG stream in input. Also, some preprocessing and filtering steps may be employed before analyzing the signal. The method 1600 begins at 1602 and proceeds to 1604.

Figure 18:
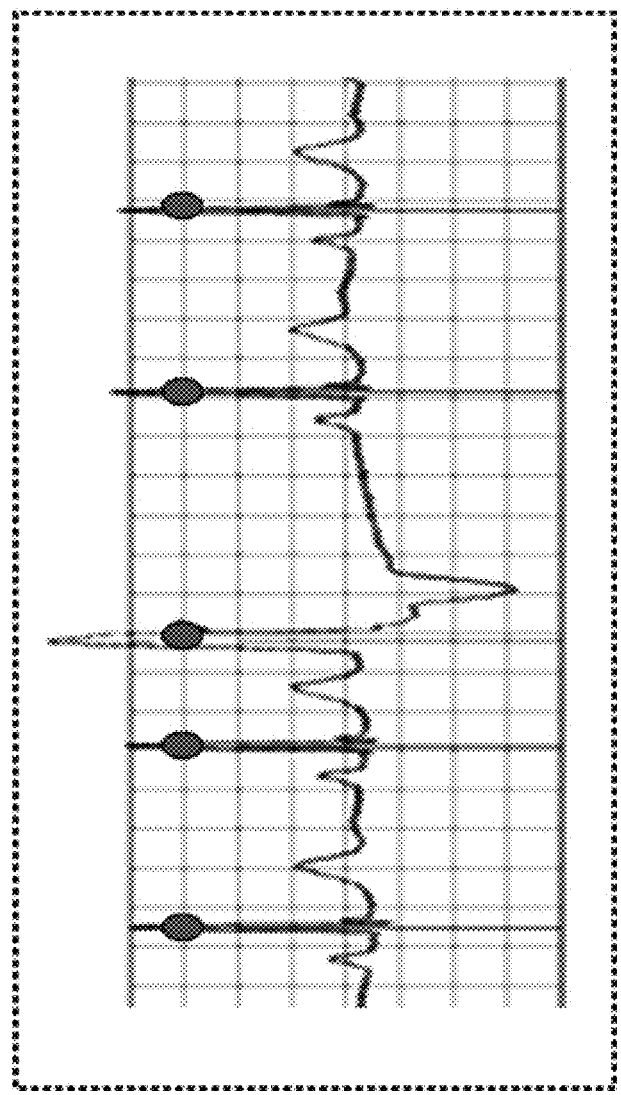
FIG. 18 is a graphical illustration of an example of beats extracted from an ECG trace.

At 1604, the R-peaks of each heart beat are detected. This may be done, for example, by filtering the ECG traces, for example using two median filters to remove the baseline, and detecting the R-peaks in the filtered signal using, for example, a Pan-Tompkins algorithm. See Pan, et al., *A real-time qrs detection* algorithm, Biomedical Engineering, IEEE Transaction on, No. 3, pp 230-236, 1985.FIG. 18 is a graphical illustration of an example of beats extracted from an ECG trace. The method 1600 proceeds from 1604 to 1606.

At 1606, a punctual heart rate (RR) is measured, for example by computing the time difference between R-peaks of a beat and an adjacent beat. A local heart rate (HR) is determined for reference windows (time intervals), which may be, for example, of a fixed size such as 10 seconds. Statistical analysis may be employed to determine the local heart rate HR, for example, the median of the punctual heart rates for beats in the window may be employed as the local heart rate in an embodiment. In an embodiment, the interquartile range $IQR=Q_3-Q_1$ may also be determined, where $Q_3$ and $Q_1$ are respectively the third and first quartile of the RRs in the window. Outliers in the punctual heart rate may be identified, for example, based on thresholds. For example, RRs below $Q_1-1.5(IQR)$ or above $Q_3+1.5(IQR)$ may be identified as outliers. Other methods of identifying outliers may be employed, such as Median Absolute Deviation (MAD). It is noted that different thresholds and other criteria may be employed in an embodiment to identify outliers in the training and detecting methods or routines. RRs identified as outliers may be removed prior to anomaly detection, as discussed below.

The method proceeds from 1606 to 1608. At 1608, the beats of the stream are windowed, for example using a reference window of a reference window size, which may be a fixed size, such as, for example, R−0.35 seconds, R+0.35 seconds. For each R-peak, a fixed-size window with a center located in the peak is extracted from the ECG stream. For example, one can consider windows of size 0:7 s (0:35 s around the R-peak). Other window sizes may be selected, for example to facilitate selecting all the PQRST waves of the current beat without including waves from the previous or subsequent beats. The chosen fixed-size window size may be referred to as a reference window size (RWS) and considered as the reference window for the particular user. At this level, heartbeats, or simply beats, refers to the collection of samples inside the chosen window. FIG. 15 is a graphical representation of an example of a windowed beat of an ECG trace.

The method proceeds from 1608 to 1610. At 1610, motion estimation is performed. In an embodiment, accelerometer data is provided as an input. The ECG data stream and the accelerometer data are synchronized or assumed to be sychronized. For each heartbeat the energy of the acceleration (EE) of the associated accelerometer data is measured. In an embodiment, the energy of the acceleration is defined as the $l_2$ norm of the accelerometer data corresponding to a window of size RWS around the R-peak. Outliers in the accelerometer data distribution may be identified, for example, using confidence intervals based on sliding windows along the trace. See, FIGS. 7-8 and the description thereof. It is noted that different thresholds and other criteria may be employed in an embodiment to identify outliers in the training and detecting methods or subroutines. FIG. 14 is a graphical representation of an example of accelerometer data. The method proceeds from 1610 to 1612.

At 1612, beats are selected so as to exclude beats which may give rise to false positive indications of anomalies. In an embodiment, this may be done by excluding beats which have both (i) a punctual heart rate identified as an outlier with respect to a local heart rate and (ii) corresponding accelerometer data identified as outlier. Such beats may be excluded because the outlier status under both criteria may be an indicator the beats are highly affected by noise or motion artifacts, or failures in the sensing process due, for example, in involuntary movements of the user. It is noted that a beat which is an outlier with respect to the RR distribution, but which is an inlier with respect to the accelerometer data, may be an anomalous beat (e.g., an atrial premature beat, a rhythmical anomaly beat, etc.). Thus, in an embodiment beats which are outlier with respect to condition (i), but which are inlier with respect to condition (ii), may be included in the beats selected for anomaly detection. In an embodiment, a beat which is outlier with respect to condition (i), but which is inlier with respect to condition (ii) may be classified as anomalous at 1612, with an indication the beat should be classified as anomalous being taken into account at 1622, as shown in FIG. 16 by the dashed line 1626.

It also is noted that beats which are inlier with respect to condition (i), but which are outlier with respect to condition (ii), may be selected for anomaly detection in an embodiment because the inlier status with respect to condition (i) may be an indicator that the morphology of the beat is preserved, and thus useful information may be obtained by including the beat in the analysis. The selected beats may also be subjected to preprocessing at 1612, such as obtaining a zero-mean vectors by subtracting the mean (e.g., vertically translating the beats). The method proceeds from 1612 to 1614.

At 1614, each beat is associated with a pair of transforms P(HR, EE) and F(HR, EE). See e.g., FIGS. 7-9 and the description thereof. The method proceeds from 1614 to 1616. At 1616, beat adaptation is applied to a beat to account for a current user state. In an embodiment, the current beat s is adapted using the identified transform P as follows:

$$s_A := P(HR, EE) \cdot s \qquad (13)$$

where $s_A$ is the adapted beat. For example, if for the current beat s the HR is relatively high, while the EE is relatively low (with respect to some derived thresholds), this may be taken as an indication that the current user state is resting after an effort. See FIG. 8.

Figure 19:
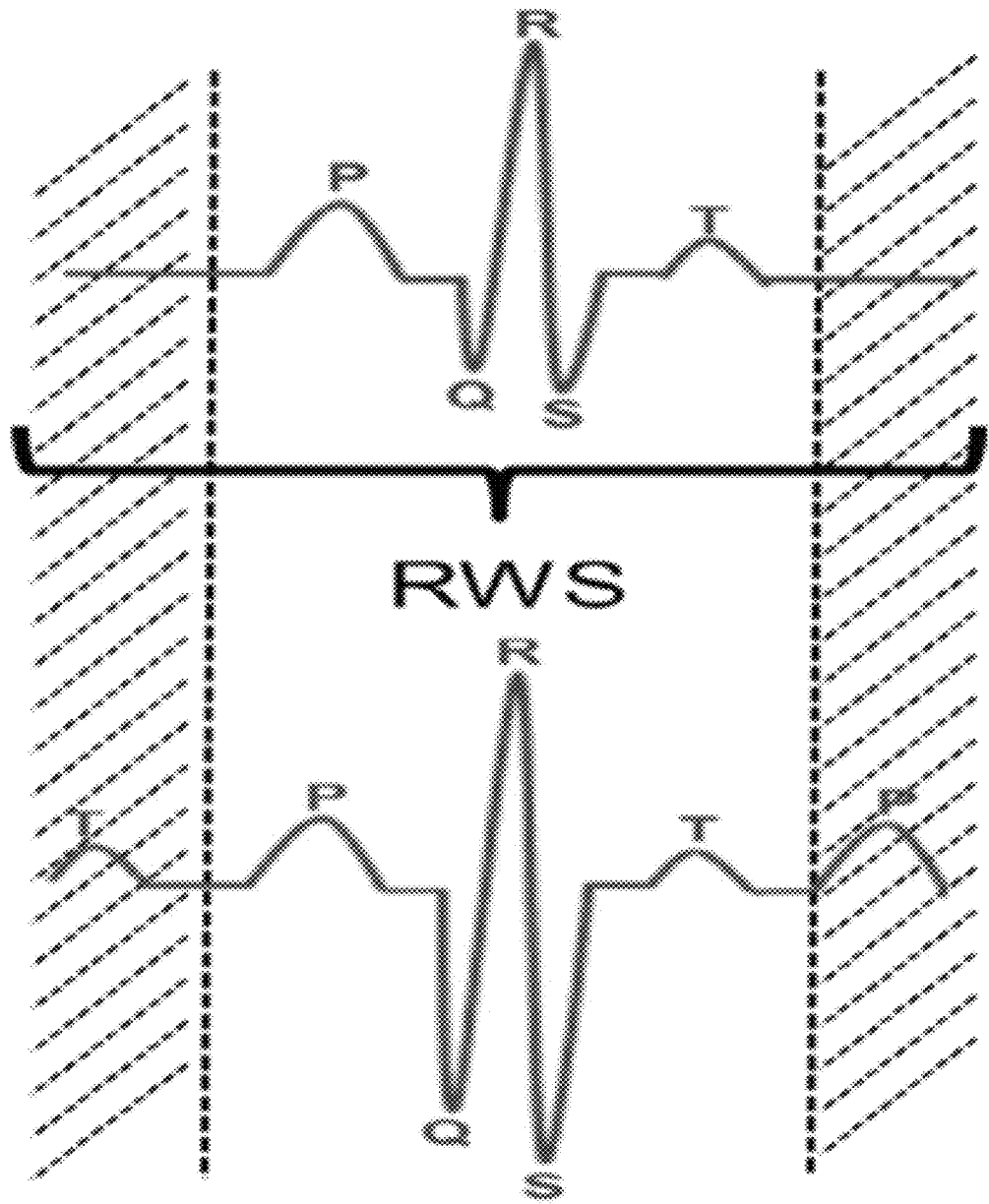
FIG. 19 is a graphical comparison of an example beat of a user in a resting state and an example beat of a user in a resting after an effort state.
Figure 20:
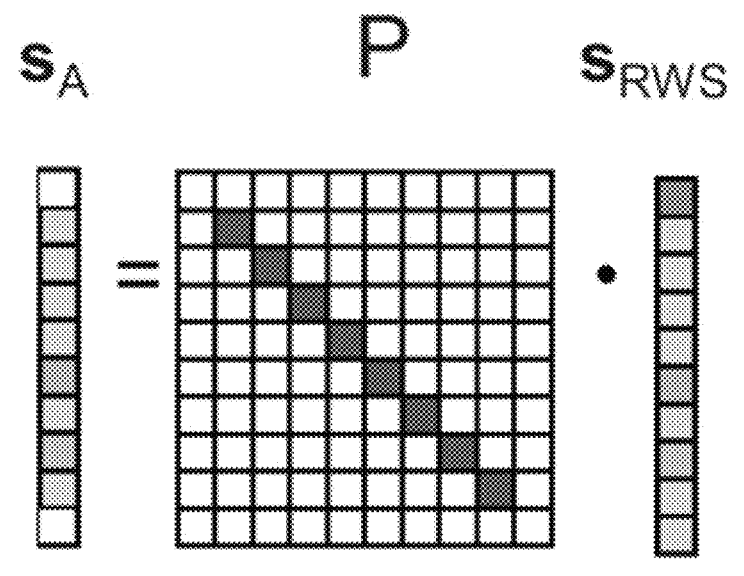
Figure 23A:
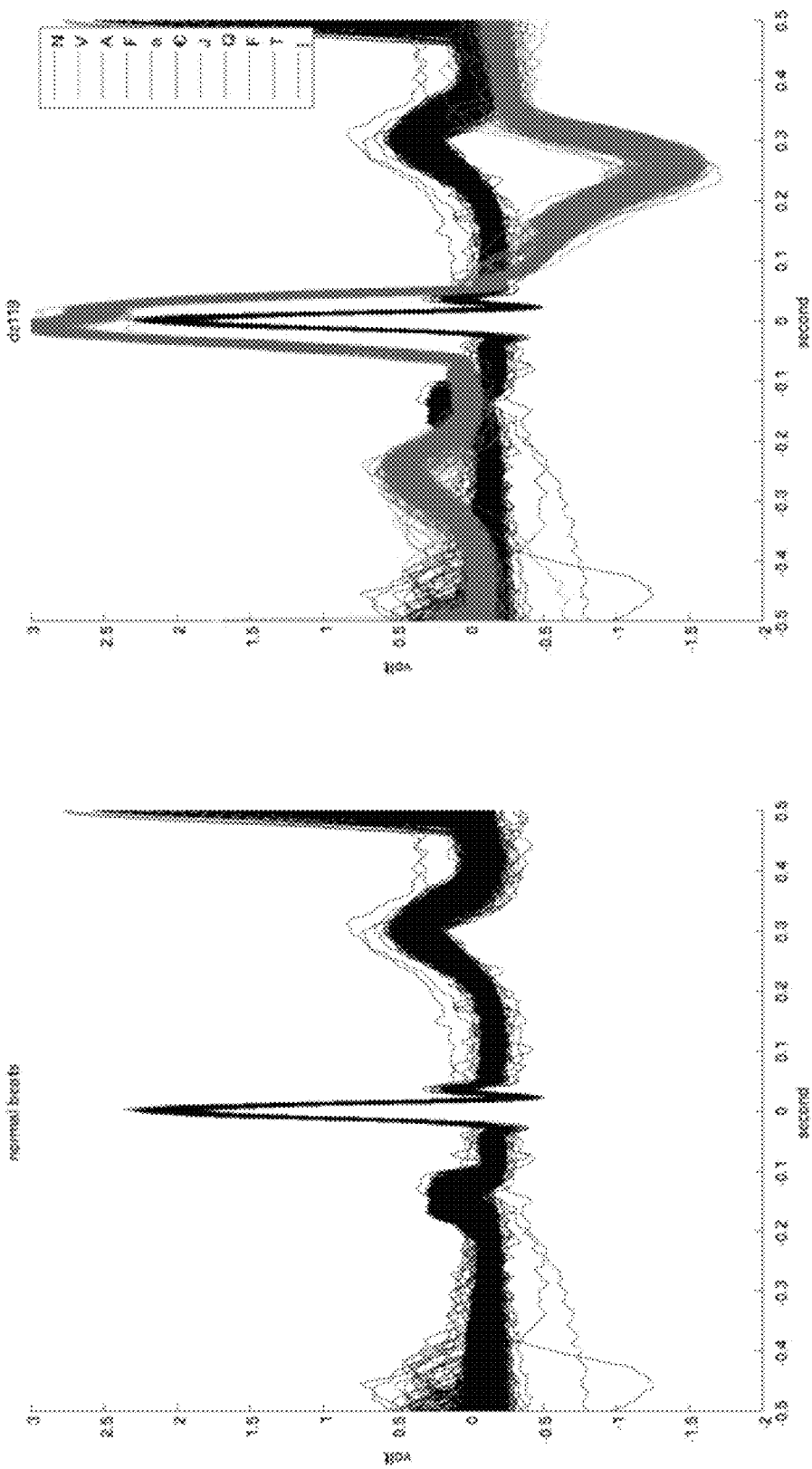
FIGS. 23A-23D illustrate example beats from patients in a study.
Figure 23B:
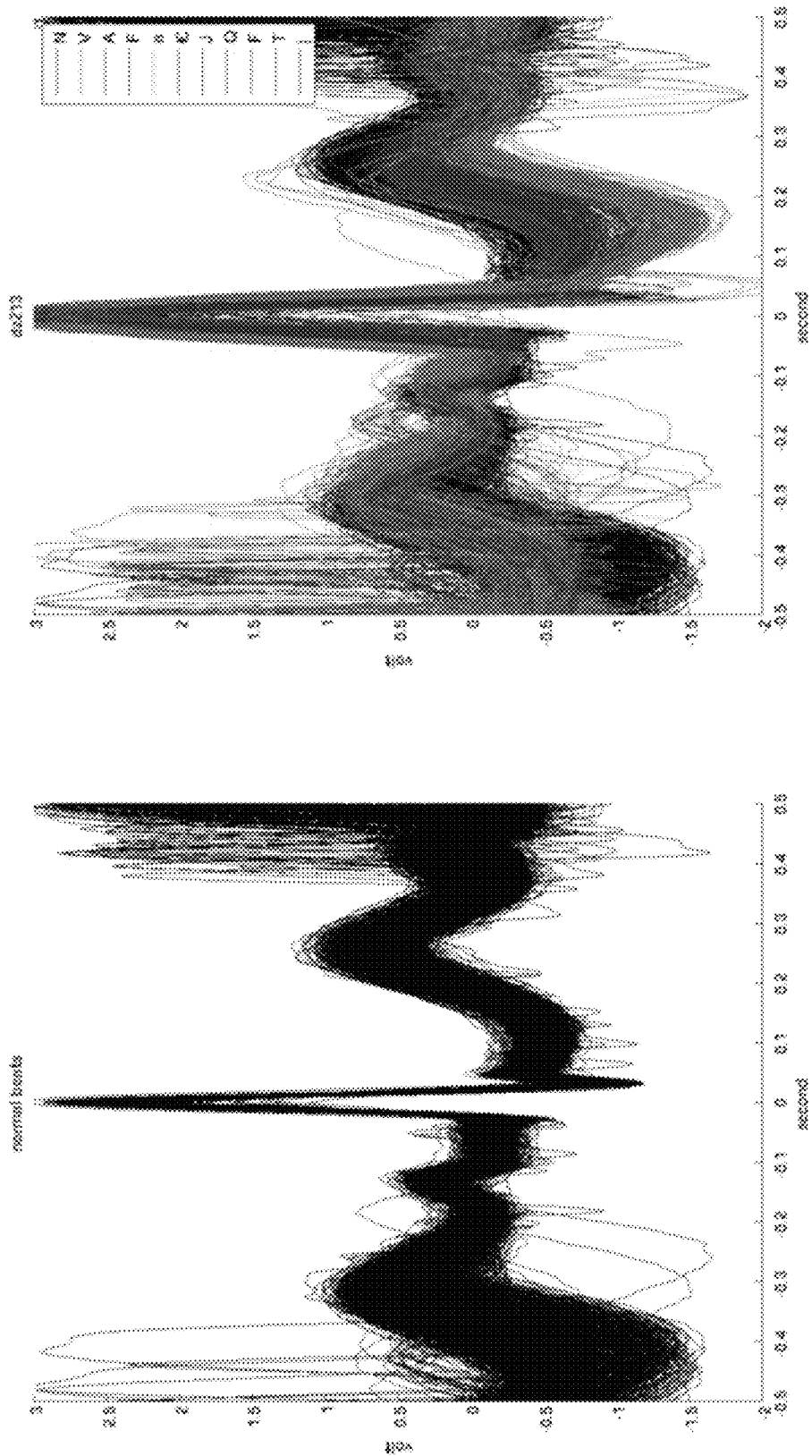
Figure 23C:
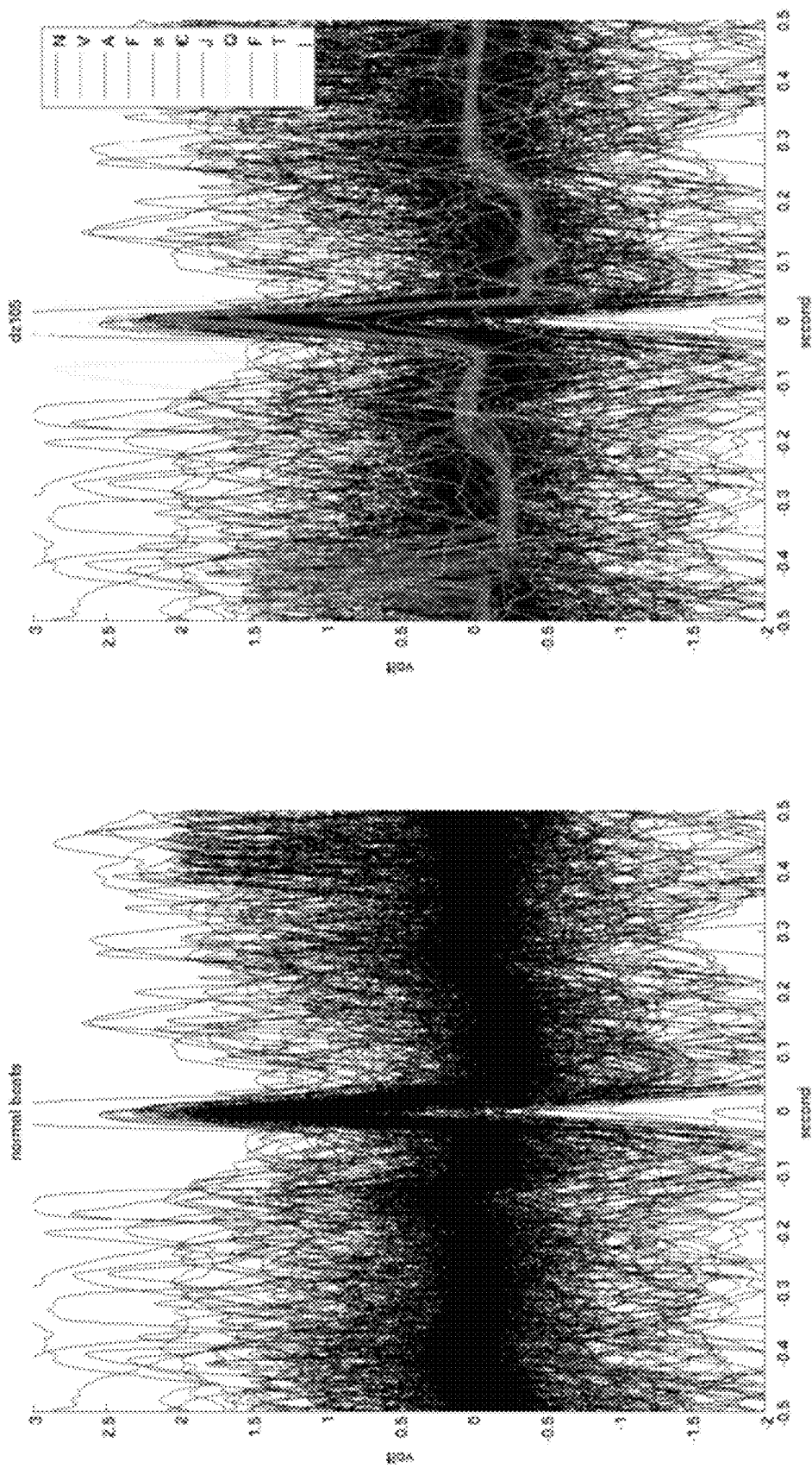
Figure 23D:
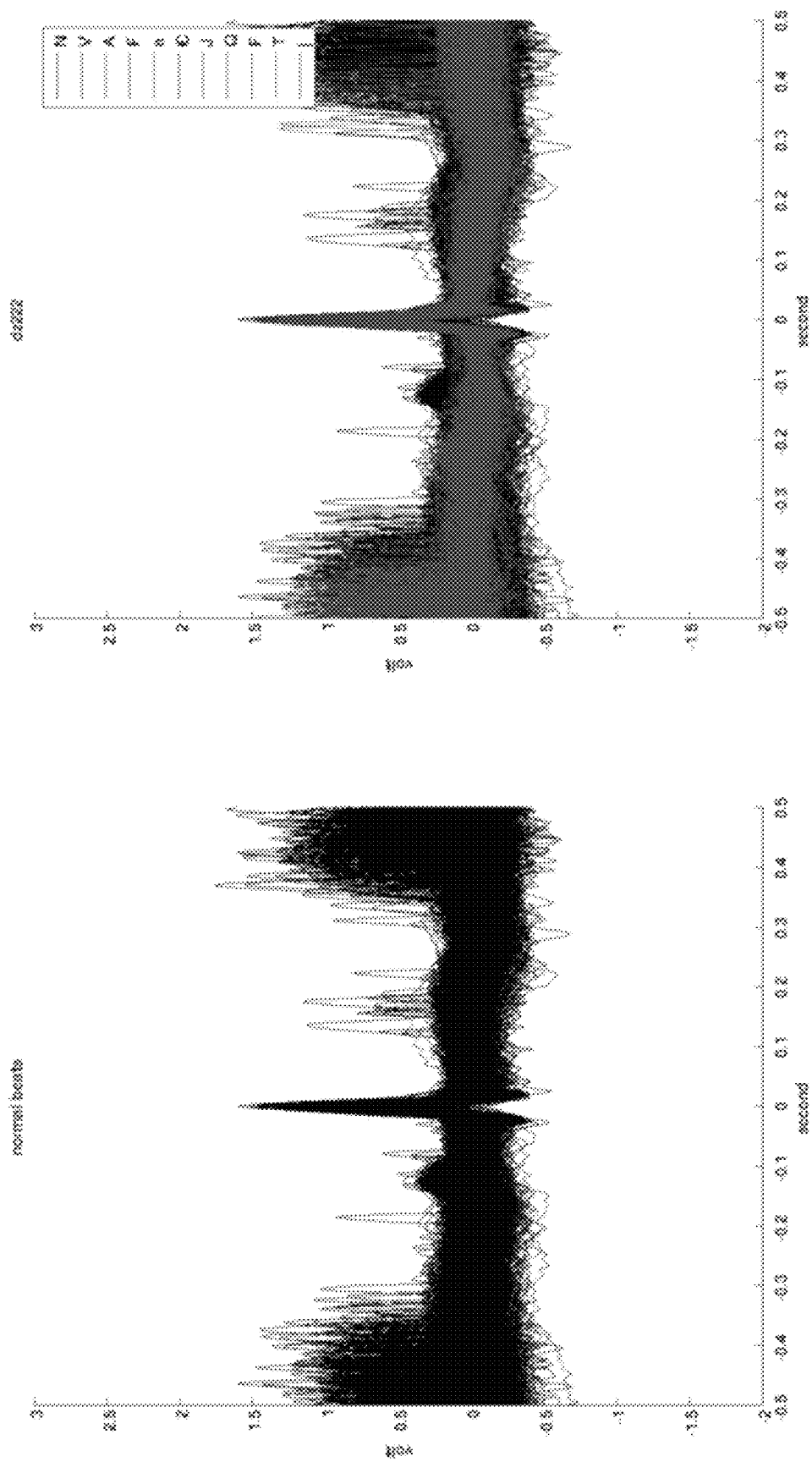

In this case, the transform P(HR, EE) may simply coincide with the projection onto a window of a size smaller than the window RWS. For example, if the heart rate is high, the beats may follow one another more closely and too wide a window (e.g., a window of size RWS), may include waves from previous or subsequent beats. See FIG. 19, which illustrates an example beat in a resting condition (top) contrasted with an example beat in a resting after an effort condition (bottom). In mathematical terms, P(HR, EE) may correspond to an identity matrix where one or more of the first and last elements of the diagonal are set to zero. This situation is illustrated in FIG. 20, which is a graphical illustration of an example application of beat adaptation in an embodiment to adapt a beat $S_{RWS}$ of a user in a resting after effort state using a transform P(HR, EE) to generate an adapted beat $s_A$. The method 1600 proceeds from 1616 to 1618.

At 1618, dictionary adaptation is applied to a beat to account for a current user state. In an embodiment, the current D is adapted using the identified transform F as follows:

$$D_A = P(HR, EE) \cdot F(HR, EE)(D) = G(HR, EE)(D) \qquad (14)$$

where $D_A$ is the adapted dictionary. For example, if for the current beat s the HR is relatively high, while the EE is relatively low (with respect to some derived thresholds) (the same conditions as discussed in the example at 1616), this may be taken as an indication that the current user state is resting after an effort. See FIG. 8. In this case, as discussed above, the transform P(HR, EE) may simply coincide with the projection onto a window of a size smaller than the window RWS. From FIG. 19, which illustrates an example beat in a resting condition (top) contrasted with an example beat in a resting after an effort condition (bottom), it can be seen that in the resting after an effort state, the morphology of the beats PQRST is slightly stretched. Thus, in an embodiment, F(HR, EE) may be a band matrix containing weights corresponding to stretched waves. See FIG. 9, which shows an example of a matrix P 902 and a matrix F 904 which may be employed by an embodiment when a beat is in a resting after an effort state. Note that G(HR, EE)=P (HR, EE)·F(HR, EE) may be a band matrix, for example, when a beat corresponds to a resting after an effort user state, which also projects the atoms of the dictionary onto a window of a smaller size than RWS, as shown in FIG. 21. The method 1600 proceeds from 1618 to 1620.

At 1620, the T-sparse approximation x of an adapted test beat $s_A$ is determined with respect to the adapted dictionary $D_A$. Note that $s_A \in R^{MA}$, the adapted test beat of s with respect to the adapted dictionary $D_A$. This may be done using an OMP algorithm, such as the method 300 of FIG. 3 or the algorithm of Table 1, to provide an approximate solution to the following problem:

$$\operatorname*{argmin}_{x} \|D_A x - s_A\|_2 \text{ s.t. } \|x\|_0 \le T \text{ for } i = 1, \dots, n \quad (15)$$

FIG. 22 is a graphical illustration of the relationships between the vectors $s_A$ and x and a dictionary $D_A$ in an iteration of an OMP algorithm in an embodiment for a user in a resting after an effort state.

The method 1600 proceeds from 1620 to 1622, where detection of anomalous beats is performed. This may be done by determining an anomaly indicator for a beat s based on the sparse approximation x of an adapted test beat $s_A$ with respect to the adapted dictionary $D_A$, comparing the anomaly indicator to expected values or ranges of values for the anomaly indicator, and classifying a beat as normal or anomalous based on the comparison. An example anomaly indicator is the root-mean-square error:

$$\text{RMSE}_{(D_A;T)}(s_A) := \|D_A x - s_A\|_2 \quad (16)$$

where $s_A$ is the adapted test beat vector, $D_A$ is the adapted dictionary, and x is the sparse approximation of the adapted test beat vector. The root-mean-square error may be compared with expected values of the root-mean-square error and the beat may be classified as normal or anomalous based on the comparison. One or more thresholds, one or more threshold ranges and one or more look-up tables may be employed to classify a beat as normal or anomalous. For example, if $$\text{RMSE}_{(D_A;T)}(s_A) > \gamma \quad (17)$$

a beat may be considered anomalous, where $\gamma$ is a threshold which determines the responsiveness to anomalies, and may typically be set to control the false positive rate, e.g., the percentage of normal beats classified as anomalous. See the discussion of anomaly indicators and FIG. 6 above. As discussed above with respect to 1612, a beat which is outlier with respect to condition (i), but which is inlier with respect to condition (ii) may be classified as anomalous at 1612, with an indication the beat should be classified as anomalous being taken into account at 1622, as shown by the dashed line 1626.

The method 1600 proceeds from 1622 to 1624, where the subroutine may return an indication of whether a beat is anomalous, where further processing may occur, etc. Embodiments of the method 1600 may perform additional acts not shown in FIG. 16, may perform the acts of FIG. 16 in different orders, may omit acts shown in FIG. 16, may modify acts shown in FIG. 16, and may combine or split acts shown in FIG. 16. For example, in an embodiment the method 1600 may be modified to check whether additional beats are to be classified at 1622 and return to 1604 to process the next beat when it is determined that additional beats remain to be classified. In another example, the subroutine may be modified to perform error processing, such as in response to a beat being classified as anomalous, initiating a transmission of data related to the beat classified as anomalous. In another example, the routine 1600 may be modified to track a proportion of beats excluded from the beats selected at 1612 within a threshold period of time, and when the proportion indicates the dictionary may no longer be valid (for example, due to a changing position of a sensor), to call a subroutine to update the dictionary, such as the subroutine 1200 of FIG. 12. Thresholds may be employed to determine whether the dictionary may no longer be valid.

Usually wearable devices continuously or periodically send all data to a host device, which may in turn send all data to a remote application server. This can result in intense energy consumption by the wearable device and the host device. In one mode of operation of an embodiment, a training phase (e.g., defining of the dictionary) may be executed on the wearable device (see system 1000 of FIG. 10). Sensed data may be transmitted by the wearable device to the host (e.g., a cell phone, see local server 1050 of FIG. 10) when an anomaly is detected, instead of periodically or continuously. The host may in turn send the data to a remote server (see remote server 1050 of FIG. 10). In one mode of operation of an embodiment, training data may be transmitted to the host device by the wearable device. The dictionary may be generated by the host device or the remote server, and transmitted to the wearable device. Sensed data may be transmitted by the wearable device to the host when an anomaly is detected, instead of periodically or continuously.

An embodiment may provide a user specific dictionary (the model learns the shapes characterizing the heart beats of a single user) which is easily reconfigurable (retrained), which is adaptive with respect to different user states (time and moving varying dynamics) without needed to learn beat shapes associated with each of the different user states, and which has robust training and testing (detection) phases (e.g. noise and motion artifacts can be detected and removed), and various combinations thereof. An embodiment may operate in an unsupervised training mode (spurious signals can be filtered from the training data). In an embodiment, all or part of the training and testing (detection) may execute on a wearable device, rather than on a host or a remote server. Compressed data (such as with compressed sensing data) may be employed in an embodiment.

In an embodiment, execution of the testing (detection) phase was implemented on a pulse sensor using a test data set and the execution of the testing (detection) phase was fast enough to facilitate real-time execution on a wearable device. A test setup used in experiments is described below. The procedure was tested using the MIT-BIH Arrhythmias Database. See Goldberger, et al., *PhysioBank, Physio Toolkit and PhysioNet: Components of a new research resource for complex physiologic signals*, Circulation, Vol. 101, No. 23, pp e215-e220, 2000.

Since for the MIT-BIH Arrhythmias Database the number of available beats per patient is not very high (from 1000 to 2500 in most cases), a k-fold cross-validation was typically performed. In k-fold cross-validation, the original sample is partitioned into k equal sized subsamples. Of the k subsamples, a single subsample is retained as the validation data for testing the model, and the remaining k−1 subsamples are used as training data. The cross-validation process is then repeated k times (the folds), with each of the k subsamples used exactly once as the validation data. The k results from the folds are then averaged to produce a single estimation.

The anomaly detection performances were typically assessed using the customary Receiver Operating Characteristic (ROC) curve, where the parameter is the threshold $\gamma$. The ROC curve plots the true-positive rate of detection (TPR), defined as the proportion of true-positive results (correctly detected anomalies), against the corresponding false-positive rate error (FPR), defined as the proportion of false-positive results (normal signals detected as anomalous). These two values change in relation to each other as the anomaly detection threshold γ varies. Recall that the area under the curve (often referred to as AUC) is equal to the probability that the detector will rank a randomly chosen anomaly higher than a randomly chosen normal beat.

For a fixed value of the γ parameter, the following was also considered: the accuracy, defined as the proportion of true results (both true-positives and true-negatives, e.g., correctly detected anomalies and correctly detected normal beats) among the total number of cases examined, the precision, defined as the proportion of true-positive results (correctly detected anomalies) against all the positive results (both true-positive and false-positive, e.g., correctly detected anomalies and normal beats detected as anomalous), and the false-negative rate (FNR), defined as the proportion of false-negative results (wrongly detected anomalies).

Other analyzed parameters include the sparsity level T, the length of the beats M, and dictionary redundancy r:=N/M.

Unless specified otherwise, the procedure discussed herein processed signals from one single lead at a time.

The source of the ECGs included in the MIT-BIH Arrhythmias Database is a set of over 4000 long-term Holter recordings obtained by the Beth Israel Hospital Arrhythmia Laboratory between 1975 and 1979. Approximately 60% of these recordings were obtained from inpatients. The database contains 23 records (numbered from 100 to 124 inclusive with some numbers missing) chosen at random from this set, and 25 records (numbered from 200 to 234 inclusive, again with some numbers missing) selected from the same set to include a variety of rare but clinically important phenomena that would not be well-represented by a small random sample of Holter recordings. Each of the 48 records is slightly over 30 minutes long. The first group is intended to serve as a representative sample of the variety of waveforms and artifact that an arrhythmia detector might encounter in routine clinical use. Records in the second group were chosen to include complex ventricular, junctional, and supraventricular arrhythmia and conduction abnormalities. The subjects were 25 men aged 32 to 89 years, and 22 women aged 23 to 89 years. Records 201 and 202 came from the same male subject.

For every patient two signals were recorded from two leads jointly with annotations on the beats. The leads vary among subjects as would be expected in clinical practice. In most records, one channel is a modified limb lead II (MLII), obtained by placing the electrodes on the chest as is standard practice for ambulatory ECG recording, and the other channel is usually V1 (sometimes V2, V4, or V5, depending on the subject).

The sampling frequency is 360 Hz. Such value was chosen to accommodate the use of simple digital notch filters to remove 60 Hz (mains frequency) interference.

For each record, the two traces were given to two cardiologists, who worked on them independently. The cardiologists added additional beat labels where the detector missed beats, deleted false detection as necessary, and changed the labels for all abnormal beats. They also added rhythm labels, signal quality labels, and comments. The annotations were transcribed from the paper chart recordings. Once both sets of cardiologists' annotations for a given record had been transcribed and verified, they were automatically compared beat-by-beat. Each discrepancy was reviewed and resolved by consensus. Once the annotations match, the results are generally appended at the R-wave peaks.

In the experiment, given an ECG trace from the MIT-BIH Arrhythmias Database, single beats were extracted and labeled according to the related annotations. Here, the experimental procedure is briefly described. Samples were read from the chosen lead together with the related annotation file (annotations are stored together with the time of the R-peak of the associated beat). The R-peaks were detected using Pan-Tompkins's algorithm (see Pan, et al., *A real-time qrs detection* algorithm, Biomedical Engineering, IEEE Transaction on, No. 3, pp 230-236, 1985) and the temporal closest label was assigned to every peak. A fixed-size window with center located in each R-peak was extracted. Window sizes of 1 s, 0.7 s or 0.4 s that correspond to beats of lengths M=360, M=252 or 144 respectively were selected. Beats were vertically translated in order to have zero mean.

Normal heart-beats belonging to different patients often exhibit significant differences. In particular some patients have very regular tracings while others present several irregularities. In order to highlight some specific behaviors and ease the understanding of the results, in some experiments patient numbers 119, 213 and 105 were selected as samples. Such patients were chosen because the morphology of their normal beats shows different behaviors: normal beats from patient 119 have always the same regular shape, while for patients 213 and 105 the morphology becomes progressively more and more irregular. Abnormal beats are usually visually identifiable from normal beats (as happens in the three selected examples). An exceptionally unlucky case is represented by patient 222, where not only normal beats are remarkably confused, but also abnormal beats are difficult or indistinguishable from normal ones.

FIGS. 23A-23D illustrate example beats from patients 119, 213, 105 and 222. In FIGS. 23A-23D, the images on the left represent normal beats in black, and the images on the right represent the normal beats in black and the abnormal beats in other colors.

Figure 24:
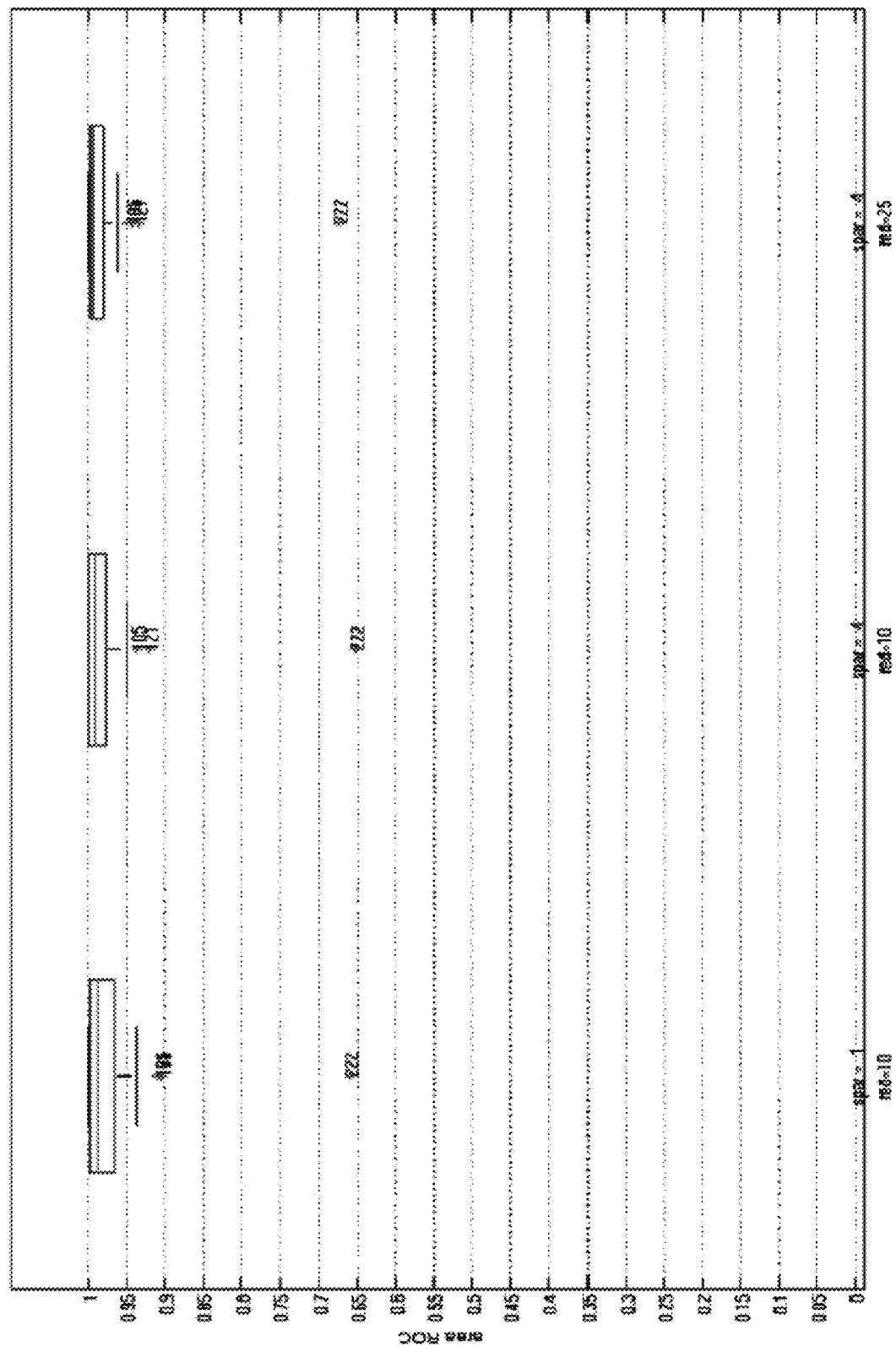
FIG. 24 illustrates the global behavior of an embodiment of an anomaly detector in a study presented in the form of whisker box-plots.
Figure 25:
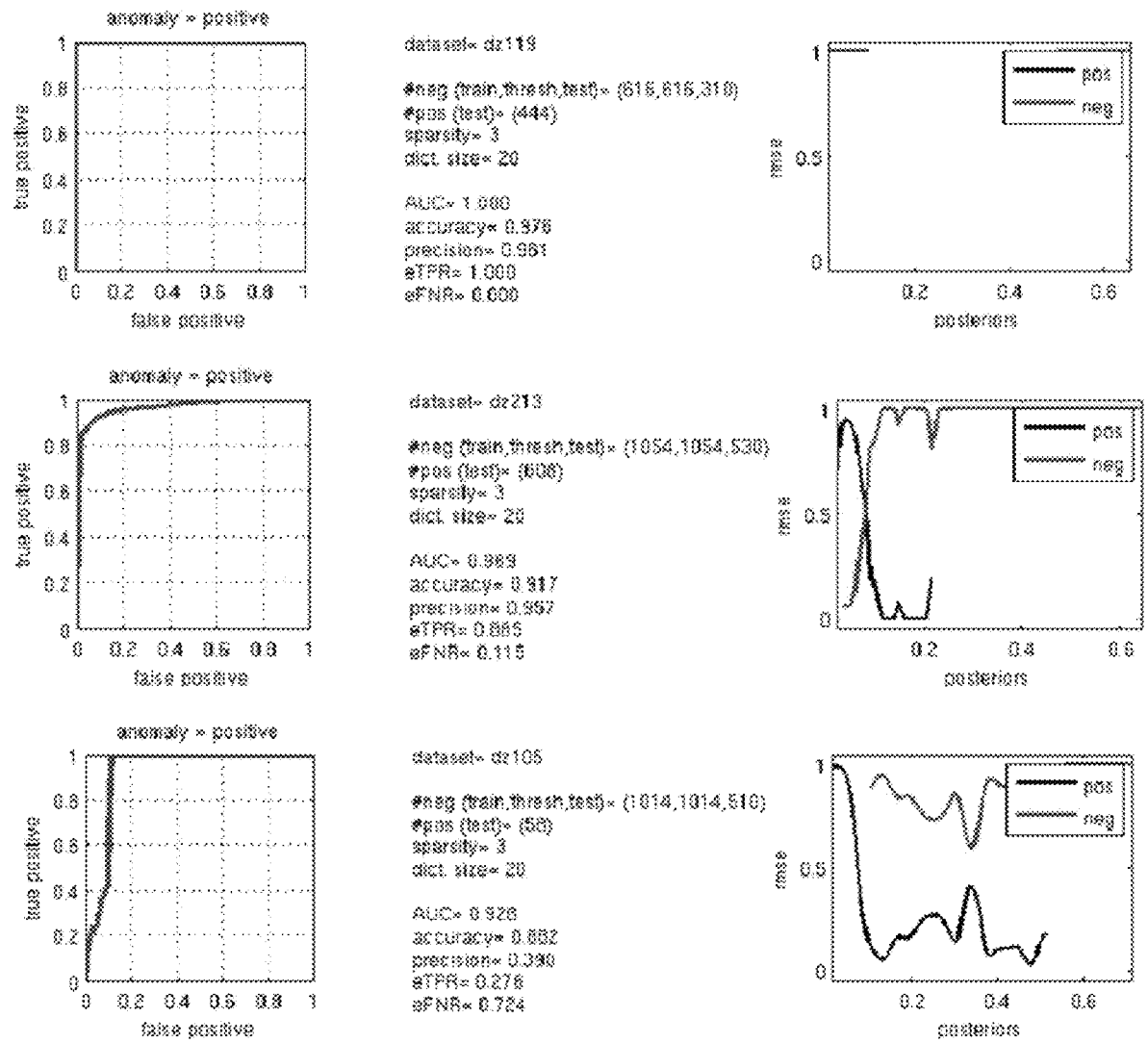
FIG. 25 represents results for sample patients in a study.

Preliminary results are encouraging as demonstrated in FIGS. 24 and 25. In particular, in FIG. 24, the global behavior of the anomaly detector is depicted, as the box-plots presents results for all the patients in the MIT-BIH Database. FIG. 25 instead represents results for sample patients. The best results were obtained for patient 119 and the worst for patient 105, which is consistent with the expected results. Results from other patients can be viewed as ranging between these two extreme cases.

FIG. 24 is a Box-plot of the area under the ROC curve (AUC) for all the patients in the MIT-BIH Database. The bottom and top of the box-plot are the first and third quartiles of the AUC respectively, and the red band inside the box is the median AUC value. The end of the whiskers represent the lowest AUC still within 1.5 IQR of the lower quartile, and the highest AUC still within 1.5 IQR of the upper quartile. Data not included between the whiskers are plotted as outliers with red marks. Box-plots are shown for different values of the sparsity level (spar) and the redundancy parameter (red). On the left-size column spar=1 and red=10, on the centre column spar=4 and red=10, and on the righsize column spar=4 and red=25. The window size is 0.7 s.

FIG. 25 illustrates detection performances for sample patients. From top to bottom, results from patients 119, 213, 105 are shown. For each patient, on the left-side column the ROC curve is shown. On the center column the patient number (dataset), the number of negative examples (#neg), e.g., normal beats, used respectively for the training (train), the evaluation (thres) and the test (test) phases, the number of positive examples (#pos), e.g., anomalous beats, used in the test phase, the sparsity level (sparsity) and the dictionary size (dict. size); the analyzed features are: the area under the ROC curve (AUC), the accuracy, the precision, the expected false-negative rate (eFNR) and expected true-positive rate (eTPR=1-eFNR) obtained setting the parameter λ corresponding to the 95-percentile, see the discussion above for an explanation of the features. On the right-size column the posterior probabilities are illustrated.

Figure 26:
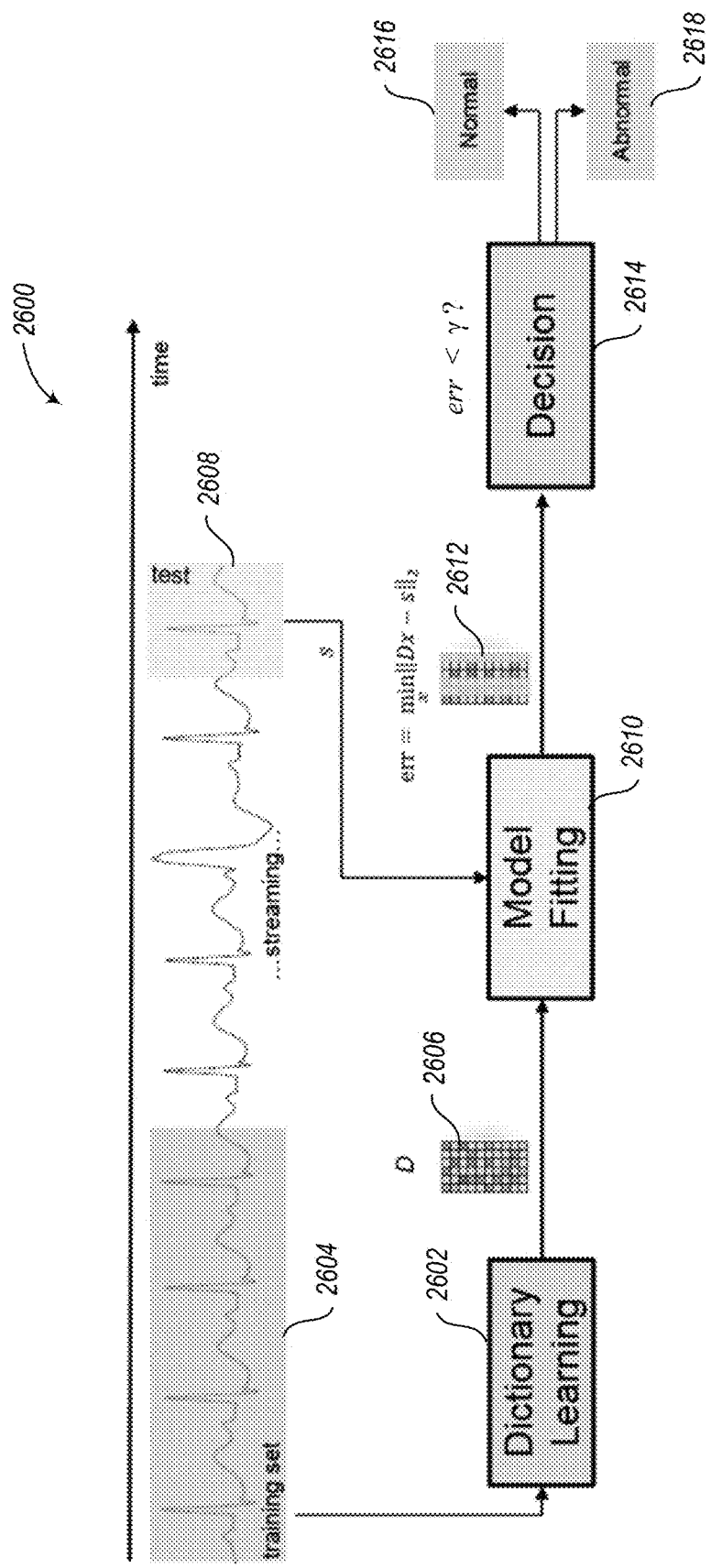
FIG. 26 is a timing diagram of an embodiment of a subroutine or method of detecting an anomaly.

FIG. 26 is a simplified timing diagram of an embodiment of a method 2600 of sparse representation based anomaly detection. A sparse dictionary model is learned 2602 from a training set of data 2604, generating a sparse dictionary D 2606. A test heart beat 2608 is fit 2610 to the learned dictionary D 2606. An error 2612 in the fitting of the test heart beat 2608 to the learned dictionary D 2606 is compared 2614 to a threshold error γ, and based on the comparison the test heart beat 2608 is classified as normal 2616 or abnormal 2618. For example, if the error in the fitting of the test heart beat to the model exceeds a threshold error γ, the test heart beat may be classified as abnormal.

ECG tracings acquired by wearable devices are more heterogeneous than ECG tracings acquired in controlled situations. During monitoring over long periods of time, the heartbeat morphology of a particular user is subject to variations due to changes in the heart-rate HR. Changes in the user's state (e.g., resting, walking, running, etc.) also may modify heartbeats. In addition, heartbeat morphology may vary depending on a particular user, a device position and a device model.

As discussed above, systems based on sparse representations may learn the morphology that characterizes a particular user's heartbeats at a specific heart-rate. Thus, the learned model may be adapted to work at different heart-rates HR. When classifying or detecting anomalies using sparse representation based systems, the adjustment could comprise applying an adaption operator (mathematically described as a transformation) to the learned model. See, for example, FIGS. 8-22 discussed above.

The transform is an approximate solution, rather than an analytic or exact solution. In addition, current adaption operators are dependent on one or more of the user's state, the specific user, the device position and the device model. The inventors have realized functioning in real-world situations may be facilitated by an adaption operator which is independent of the user's state (e.g., running, walking, resting, etc.), the specific user, the device position and the device model.

Another approach may be to jointly learn projections of data from two domains onto a common subspace and a sparsifying dictionary representing data in the projected low-dimensional space. See S. Shekhar, et al., *Generalized domain adaptive dictionaries*," IEEE Conference on Computer Vision and Pattern Recognition (2013). However, the learned transformations are orthogonal projections and are applied to ECG traces, not to dictionaries, which introduces inefficiencies. The transforms also do not generalize to new users.

As discussed above, heartbeats acquired by wearable devices may be characterized by specific morphological structures, and a sparse model well describes these structures. The inventors have realized that the changes in the heart-rate modify the heartbeat morphology according to a physiological phenomenon that may be well described by an unknown family of linear transformations. In particular, a single adaption operator may be employed to describe each change from one heart-rate (e.g., $r_1$) to another heart-rate (e.g., $r_2$), and that such physiological phenomenon may be modeled independent of the user's state, the specific user, the device position and the device model by a set of transforms.

Thus, a framework is proposed by the inventors to adapt sparse representations of ECG data at a domain corresponding to different heart-rates HR. The adaptation may be achieved by learning a family of adaption operators, which are independent of a user's state, a particular user, a device position and a device model. This facilitates generalizing to new users.

Figure 27:
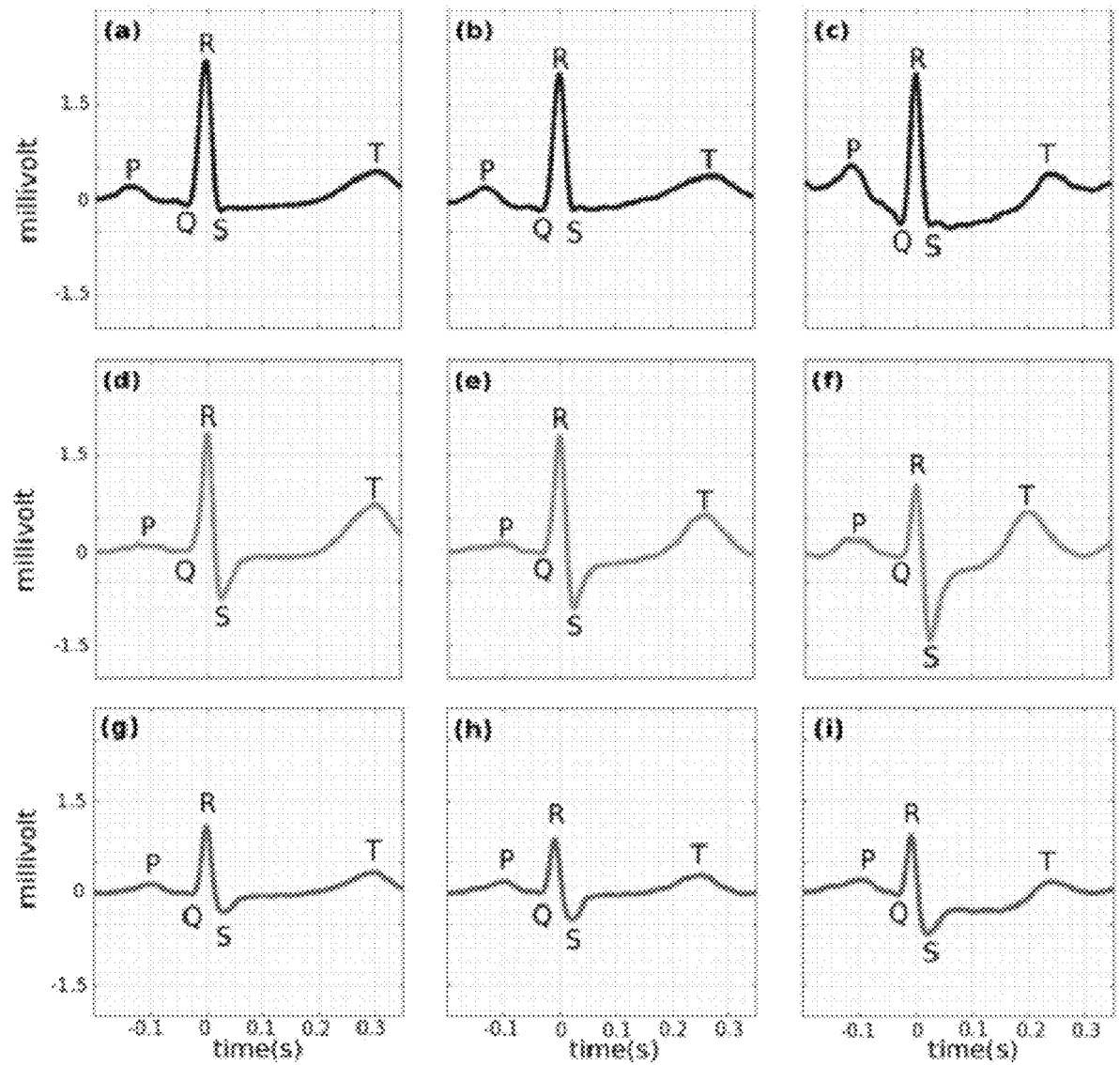
FIG. 27 illustrates examples of heartbeat morphology at different heart-rates.

FIG. 27 illustrates examples of heartbeat morphology at different heart-rates. Each row depicts heartbeats from two different users selected from a public database, G. B. Moody, *Mit-bih arrhythmia database directory*, (May 1997), at heart-rates respectively of 60 bpm (a and d), 90 bpm (b and e), and 120 bpm (c and f). Heartbeats in examples a and d can be considered as acquired in resting conditions. Letters in FIG. 27 indicate the P-waves, the QRS-complexes and the T-waves, as they are typically referred to in the medical context. See D. L. Mann et al., *Braunwald's heart disease: a textbook of cardiovascular medicine*, Elsevier Health Sciences, 2014. R-peaks can be easily detected by the Pan-Tompkins algorithm and are used to align each single heartbeat. See J. Pan et al., *A real-time qrs detection algorithm*, Biomedical Engineering, IEEE Trans. on, no. 3, pp. 230-236 (1985). When the heart-rate increases, the T-waves approach the QRS complex and the QT interval narrows. Overall, when the heartbeats accelerate, the support of the heartbeats contracts and heartbeats seem to exhibit similar transformation in the two users, which does not seem to be a dilation contraction, as peaks change their intensity and shape. Even if the heart-rate increases, the cardiac conduction mechanisms are constant in normal conditions, thus essentially the same phenomenon is being monitored for different users. Substantial shape variations in the two rows depend on different electrode locations, rather than on changes in the cardiac conduction.

In an embodiment, a domain-adaptation solution is proposed that maps user-specific dictionaries through a set of linear transformations, which are general enough to be user-independent and to be successfully learned from a public dataset containing ECG tracings. See A. L. Goldberger et al, *PhysioBank, PhysioToolkit, and PhysioNet: Components of a new research resource for complex physiologic signals*, Circulation, vol. 101, no. 23, pp. e215-e220, 2000 (June 13). These transformations are learned by minimizing a function to map a union of low-dimensional subspaces from the source to the target domain. The transformed dictionaries provide sparse representation of heartbeats at different heartrates, as discussed in more detail below. In an embodiment, the domain-adaptation solution can be used to perform online ECG monitoring in wearable devices. In an embodiment, an implementation of an anomaly-detection algorithm may substantially reduce the computational complexity with respect to baseline implementations, meaningfully reducing the power consumption.

As discussed elsewhere herein, sparse representation models assume a signal $s \in \mathbb{R}^M$ can be described as $s \approx Dx$, where $D \in \mathbb{R}^{M \times N}$ is a dictionary and $x \in \mathbb{R}^N$ is T-sparse, namely, the vector has only T nonzero components. In other words, s may be well represented by a linear combination of a few (T<N) columns of $D=[d_1| \ldots |d_n]$.

Given D and T, the sparse representation x of a given signal s can be obtained by solving the following problem (via, for example, the OMP algorithm):

$$\underset{x}{\operatorname{argmin}} \|Dx - s\|_2 \text{ s.t. } \|x\|_0 \leq T \qquad (18)$$

for $I=1, \ldots, n$.

Dictionary learning techniques find the unknown dictionary D which gives the best T-sparse representation of a given training set of signals $\{s_i\}$, $i=1, \ldots, n$.

Let $S=[s_1 | \ldots | s_n] \in R^{M \times n}$ and $X=[x_1 | \ldots | x_n] \in R^{N \times n}$ be the matrices obtained by arranging column-wise the vectors si and xi respectively, the dictionary D can be obtained by solving the following problem (using, for example, the K-SVD algorithm):

$$\underset{D, \{x\}_{i=1}^n}{\operatorname{argmin}} \|DX - S\|_F^2 \text{ s.t. } \|x_i\|_0 \leq T \text{ for } i = 1, \ldots, n \qquad (19)$$

where F denotes the Frobenius norm. See also, the discussion of Equation 7 and FIG. 4, above.

Let index u denote both the user and device position. In addition, assume the ECG tracings can be segmented in heartbeats centered in the R peaks, and that normal heartbeats of a user u are generated by an unknown stochastic process $s^{(u)} \sim P_N^{(u)}$. Then, the morphology of the heartbeats changes as the heart-rate changes, so $s^{(u)} \sim P_{N,r}^{(u)}$, where r is the heart-rate corresponding to heartbeat $s^{(u)}$. Assume an unknown family of adaption operators $\mathcal{F} = (F \ldots, r)$ exists such that:

$$P_{N,\tilde{r}}^{(u)} = F_{\tilde{r},r}(P_{N,r}^{(u)}) \qquad (20)$$

and $F_{\tilde{r},r}$:
(i) can be implemented as a linear map applied to the dictionary corresponding to $P_{N,r}^{(u)}$; and
(ii) is independent from the user's state, the specific user, the device position and the device model.

Then, to model variations in the heartbeat morphology due to a change, such as an increase, in the heart-rate, the map $F_{\tilde{r},r}$ may be designed as a local transformation of the atoms of the dictionary. More precisely, the i-th sample in the transformed atom depends on its neighbors in the original atom, and the support of $F_{\tilde{r},r}$ (the set of non-zero components).

Consider a set of dictionaries learned from several users at the heart-rate r, $\{D_r^{(u)} : u=1, \ldots, U\}$ and a set of heartbeats acquired from the same users at heart-rate $\tilde{r}$, $\{S_{\tilde{r}}^{(u)} : u=1, \ldots, U\}$. The adaptation operator from heart-rate r to $\tilde{r}$ may be computed by solving the following problem:

$$\hat{F}_{\tilde{r},r} = \underset{F, X}{\operatorname{argmin}} \frac{1}{2} \sum_{u=0}^{U} \|S_{\tilde{r}}^{(u)} - FD_r^{(u)} X^{(u)}\|_2^2 + \qquad (21)$$

$$\mu \sum_{u=0}^{U} \|X^{(u)}\|_1 + \frac{\lambda}{2} \|W \odot F\|_2^2 + \xi \|W \odot F\|_1$$

where:
$F \in \mathbb{R}^{p_{\tilde{r}} \times p_r}$;
$W^{(u)} \in \mathbb{R}^{p_{\tilde{r}} \times p_r}$ is a suitable weight matrix which assigns different weights to different regions of F; and
$\hat{X}^{(u)}$ contains the sparse representations of the heartbeats $S_{\tilde{r}}^{(u)}$ with respect to the dictionary $FD_r^{(u)}$. The first term in the cost function represents a data fidelity term. Three regularization terms are employed which are controlled by three non-negative parameters, $\lambda$, $\mu$ and $\xi$. A Hadamard product is represented as $\odot$ in equation 21. In an embodiment, a random search method may be employed. See J. Bergstra et al., *Random Search for Hyper-Parameter Optimization*, Journal of Machine Learning Research 13, pp. 281-305 (2012).

In an embodiment, the first two terms in equation 21 ensure that the transformed dictionary $FD_r^{(u)}$ provides a sparse approximation of each heartbeat in $S_{\tilde{r}}^{(u)}$. The sparsity is enforced by penalizing the $l^1$ norm of the coefficient vectors. The other two terms represent a weighted elastic net penalization, which improves the stability of the learning process and steers the estimated F toward reasonable properties. In an embodiment, the weight matrix W may be employed to include in the minimization process some a priori information about the transformation $\hat{F}_{\tilde{r},r}$. For example, in an embodiment the transformation may be expected to be local in that, for each atom, the output of a sample in the dictionary is determined by a few neighboring samples. To steer the learning process toward solutions having this property, large weights may be used in positions far from the diagonal of F, and small weights may be employed close to the diagonal.

The problem of equation 21 is not jointly convex in $X^{(u)}$ and F, but the function to be minimized is convex with respect to each variable when the other one is fixed. In such circumstances, the Alternating Direction Method of Multipliers (ADMM) (see S. Boyd et al., *Distributed optimization and statistical learning via the alternating direction method of multipliers*, Foundations and Trends in Machine Learning, vol. 3, no. 1, pp. 1-122, (2011)) has been shown to have good convergence properties in practice. See Q. Liu et al., *An augmented lagrangian approach to general dictionary learning for image denoising*, Journal of Visual Communication and Image Representation, vol. 23, no. 5, pp. 753-766 (2012). The idea behind the ADMM is to split the optimization problem in many sub-problems, and alternate the optimizations of such sub-problems.

For example, introducing the auxiliary variables $G \in \mathbb{R}^{p_{r_1} \times p_{r_0}}$ and $Y^{(u)} \in \mathbb{R}^{n \times m}$, an equivalent optimization problem may be considered:

$$\underset{F, \{X^{(u)}\}_u, G, \{Y^{(u)}\}_u}{\operatorname{argmin}} \frac{1}{2} \sum_{u=1}^{L} \|S^{(u,r_1)} - FD^{(u,r_0)} X^{(u)}\|_2^2 + \mu \sum_{u=1}^{L} \|Y^{(u)}\|_1 + \qquad (22)$$

$$\frac{\lambda}{2} \|W \odot G\|_2^2 + \xi \|W \odot G\|_1,$$

s.t. $F - G = 0$, $X^{(u)} - Y^{(u)} = 0$, $\forall u$

According to the ADMM framework, a solution of (22) can be obtained by iteratively solving the following sub-problems $$X_{k+1}^{(u)} = \underset{X}{\operatorname{argmin}} \frac{1}{2} \|S^{(u,r_1)} - FD^{(u,r_0)} X\|_2^2 + \frac{\rho}{2} \|X + Y_k^{(u)} + Z_k^{(u)}\|_2^2, \qquad (23)$$

-continued $$Y_{k+1}^{(u)} = \underset{Y}{\operatorname{argmin}} \mu \|Y\|_1 + \frac{\rho}{2}\|X_{k+1}^{(u)} - Y + Z_k^{(u)}\|_2^2, \quad (24)$$

$$F_{k+1} = \underset{F}{\operatorname{argmin}} \frac{1}{2}\sum_{u=1}^{L} \|S^{(u,r_1)} - FD^{(u,r_0)}X_{k+1}^{(u)}\|_2^2 + \frac{\rho}{2}\|F + G_k + H_j\|_2^2, \quad (25)$$

$$G_{k+1} = \underset{G}{\operatorname{argmin}} \frac{\lambda}{2}\|W \odot G\|_2^2 + \xi\|W \odot G\|_1 + \frac{\rho}{2}\|F_{k+1} - G + H_k\|_2^2, \quad (26)$$

$$Z_{k+1}^{(u)} = Z_j^{(u)} + X_{k+1}^{(u)} - Y_{k+1}^{(u)}, \quad (27)$$

$$H_{k+1} = H_k + F_{k+1} - G_{k+1}, \quad (28)$$

where $Z^{(u)}$ and H are the Lagrange multipliers of the constraints in (22). See, S. Boyd et al., *Distributed optimization and statistical learning via the alternating direction method of multipliers*, Foundations and Trends in Machine Learning, vol. 3, no. 1, pp. 1-122 (2011).

In an embodiment, these sub-problems may be easily and efficiently solved as follows: sub-problems (23) and (25) are standard quadratic expressions which can be efficiently solved as linear system, using techniques such as Gaussian elimination. Problem (24) admits a closed-form solution as the proximal mapping of $\mu/\rho\|\cdot\|_1$.

$$[Y_{k+1}^{(u)}]_{ij} = S_{\mu/\rho}([X_{k+1}^{(u)} + Z_k^{(u)}]_{ij}), \quad (29)$$

where $[\cdot]_{ij}$ denotes the entry of the i-th row and the j-th column of a matrix and $S_\eta: \mathbb{R} \to \mathbb{R}$ is the soft-thresholding operator defined as $$S_\eta(x) = \operatorname{sign}(x) \cdot \max\{0, x - \eta\}. \quad (30)$$

See, A. Beck et al., *Gradient-based algorithms with applications in signal recovery*, Convex optimization in signal processing and communications, pp. 42-88 (2009).

Applying calculus and by the result in Y. L. Yu, *On decomposing the proximal map*, Advances in Neural Information Processing Systems (NIPS), pp. 91-99, 2013), it follows that problem (equation 26) can be also solved by the soft thresholding operator as follows:

$$[G_{k+1}]_{ij} = \frac{1}{1 + \lambda[W]_{ij}^2} S_{\xi[W]_{ij}/\rho}([F_{k+1} + H_k]_{ij}). \quad (31)$$

In principle, a transformation that maps the signal from the target domain to the source one can be learned by moving the F in (21) before the term $S^{(u,r)}$. The corresponding optimization problem can be solved using a formulation of the ADMM. However, this solution may not be practical in online monitoring, since it would require transforming each heartbeat, while an embodiment of a method transforms the dictionary only once.

In an embodiment, a domain-adaptation method can be used to perform online monitoring of ECG tracings directly from a wearable device. In particular, an embodiment addresses the problem of detecting anomalous heartbeats that might indicate dangerous arrhythmias and while reducing the computational complexity of the overall monitoring algorithm, to facilitate longer operation of these battery-powered devices. To adapt dictionaries to different heart-rates during long-term monitoring, an embodiment uploads on a device a set of transformations estimated from a public dataset as described in above. Although the heart-rates (e.g., $r_0, r_1$) can assume continuous values, the heart-rates may be conveniently quantized, for example, in a range having resolution of 5 bpm (beats per minute).

In an embodiment, standard preprocessing techniques are applied to ECG tracing while the tracing is acquired, in particular to remove the baseline wander. See P. De. Chazal et al., *Automatic classification of heartbeats using ecg morphology and heartbeat interval features*, IEEE Transactions on Biomedical Engineering, vol. 51, no. 7, pp. 1196-1206 (2004). The heartbeats may be extracted by cropping a window of pr samples around each R-peak, which are detected by the Pan-Tompkins algorithm. See S. J. Pan et al., *A real-time qrs detection algorithm*, Biomedical Engineering, IEEE Trans. on, no. 3, pp. 230-236 (1985). These peaks may be used also to estimate the reference heart-rate r of each heartbeat, by averaging the reciprocals of the R-R intervals (the distance between consecutive R peaks) over a window of the latest 5 seconds.

During the user-specific configuration of an embodiment, 10 minutes of ECG tracings from the user u in resting conditions were recorded. This is enough to collect heartbeats in $S(u, r_0)$ which are used for learning the user-specific dictionary $D(u, r_0)$ using the KSVD algorithm. See M. Aharon et al., K-svd: *An algorithm for designing overcomplete dictionaries for sparse representation*, IEEE Transactions on Signal Processing, vol. 54, no. 11, pp. 4311-4322 (2006). The heart-rate $r_0$ associated to this dictionary, e.g., the source heart-rate, is the most frequent heart-rate in $S(u, r_0)$.

During online monitoring of an embodiment, as soon as a new heartbeat $S(u, r_1)$ is being acquired, the target heart-rate is measured and, in case $r_0$ does not equal $r_1$, the user-specific dictionary $D(u, r_0)$ is transformed to the target heart-rate $r_1$ by computing $$\hat{D}^{(u,r_1)} = \hat{F}_{r_1,r_0} D^{(u,r_0)}$$

Anomalous heartbeats may be detected as described below, where for the notation sake the superscript $(u,r_1)$ is omitted, since all the variables refer to the user u and the target heart-rate $r_1$. In an embodiment, the approach presented in D. Carrera, et al., *Ecg monitoring in wearable devices by sparse models*, in Joint European Conference on Machine Learning and Knowledge Discovery in Databases, pp. 145-160, Springer, (2016) may be employed and s may be identified as anomalous if it is not close to the union of low-dimensional subspaces generated by the transformed dictionary $\hat{D}$. In an embodiment, the sparse representation $\hat{x}$ of s with respect to the transformed dictionary is computed by solving the sparse coding problem:

$$\hat{x} = \underset{x}{\operatorname{argmin}} \|s - \hat{D}x\|_2^2, \quad (32)$$

$$\text{s.t. } \|x\|_0 \leq \kappa,$$

where the functional to be minimized is the $l^2$ norm of the residual with respect to the dictionary, and $\|x\|_0$ is the number of nonzero coefficients in x, which is set to a maximum value k>0. The sparse coding problem of equation 32 is NP-Hard and suboptimal solutions may be computed by greedy algorithms. In an embodiment, Orthogonal Matching Pursuit (see R. Rubinstein, et al., *Double sparsity: Learning sparse dictionaries for sparse signal approximation*, IEEE Transactions on Signal Processing, vol. 58, no. 3, pp. 1553-1564, (2010)) is adapted for the sparse coding. The reconstruction error may be computed as:

$$e(s) = \|s - \hat{D}\hat{x}\|_2. \quad (33)$$

The reconstruction error may be used as an indicator to discriminate between normal and anomalous heartbeats, according to the rule:

$$s \text{ is anomalous} \Leftrightarrow e(s) < \gamma, \quad (34)$$

thus recognizing as anomalous any heatbeat that cannot be properly reconstructed by the dictionary $\hat{D}$. The parameter $\gamma$ determines the promptness of the detector to identify anomalous heartbeats.

As discussed above, the solution to the problem of equation 21 should map $D_r^{(u)}$ into a new dictionary providing good sparse approximation of signals in $S_r^{(u)}$. This optimization problem may be solved using, for example, an Alternative Direction Method of Multipliers (ADMM) algorithm, which has good convergence properties. Other algorithms may be employed to solve the problem of equation 21. In addition, the adaptation operator from heart-rate r to r̃ may be computed by solving other problems using the ADMM algorithm or other algorithms.

Figure 28:
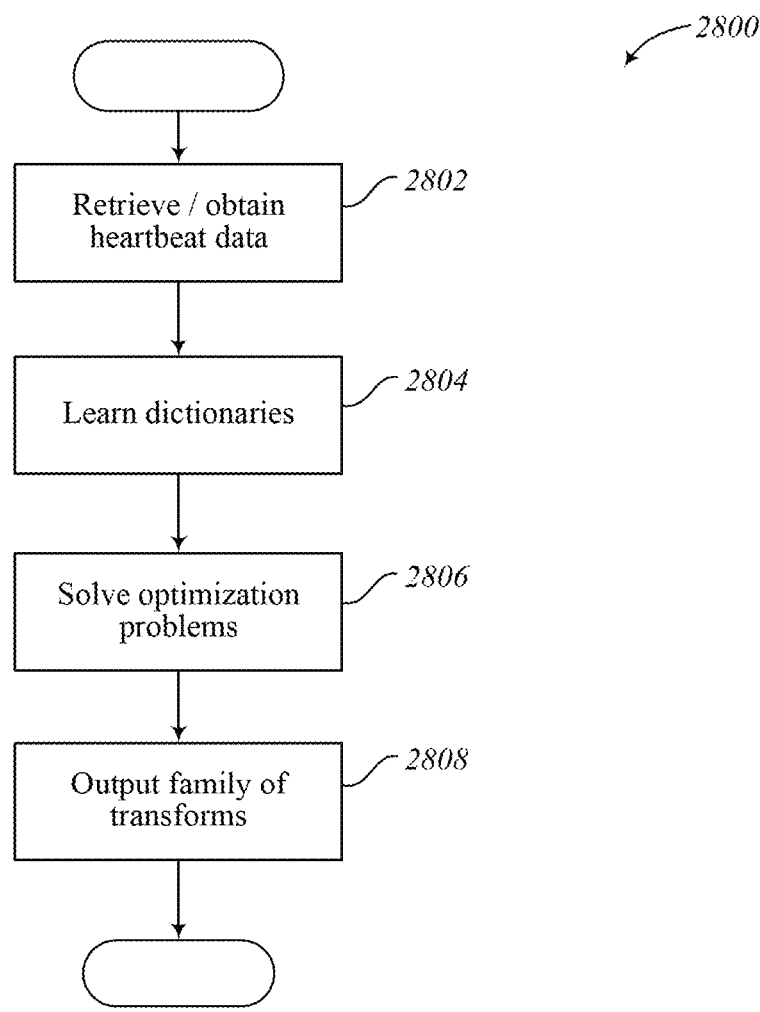
FIG. 28 illustrates an embodiment of a subroutine or method of a learning phase to generate a family of adaption operator transforms.
Figure 29:
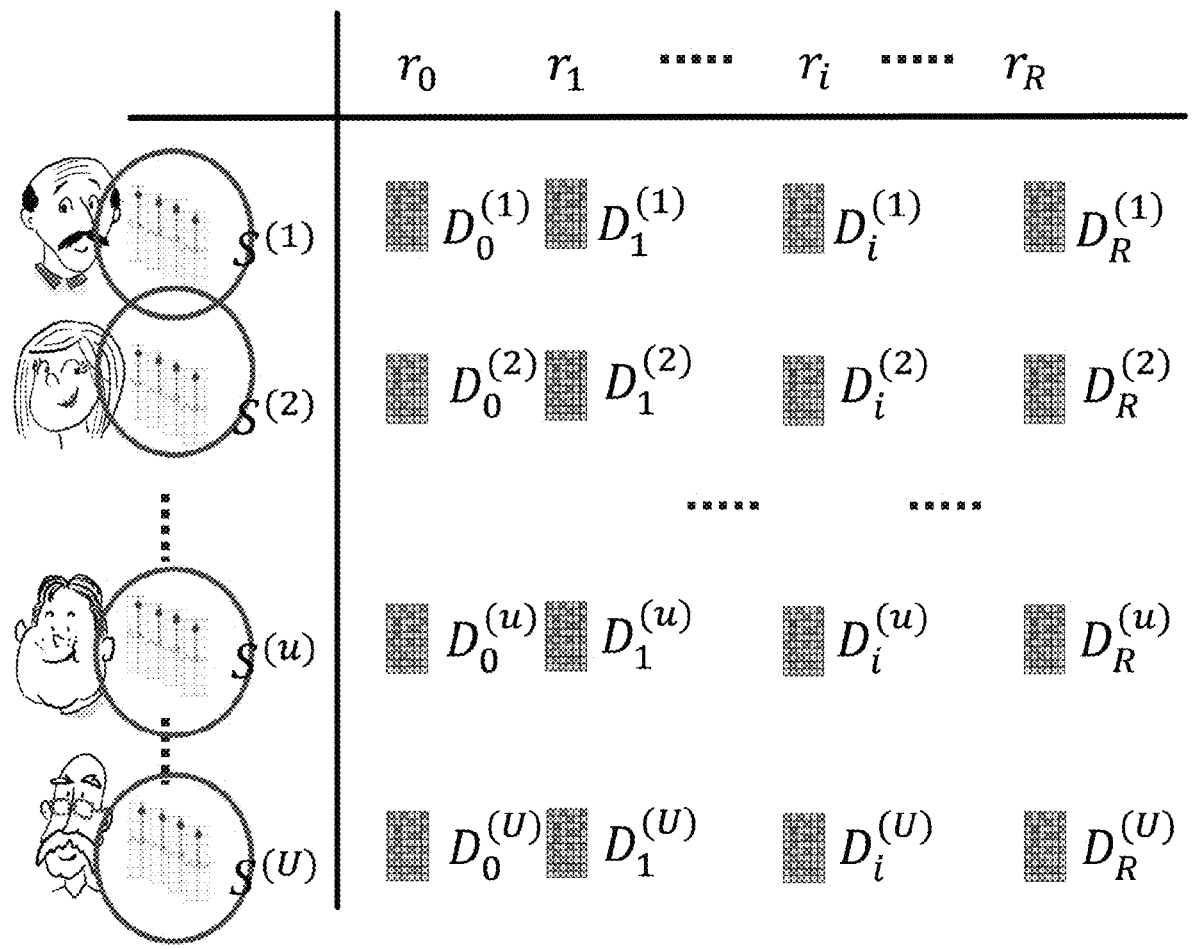
FIG. 29 illustrates example heartbeat data input to an embodiment of the method of FIG. 28.

FIG. 28 illustrates an embodiment of a subroutine or method 2800 of generating a family of adaption operation transforms. The method 2800 may be employed, for example, by an embodiment of a system 1000 of FIG. 10, by a server, such as the server 1050 of FIG. 10, and various combinations thereof. At 2802, heartbeat data associated with several users and acquired at difference heart-rates is obtained, for example, by retrieving heartbeat data from a database, such as the MIT-BIH Arrhythmias Database, by gathering data from several users at different heart-rates, etc. FIG. 29 illustrates an example set of heartbeat data associated with several users S at different heart-rates r. The method proceeds to 2804.

Figure 30:
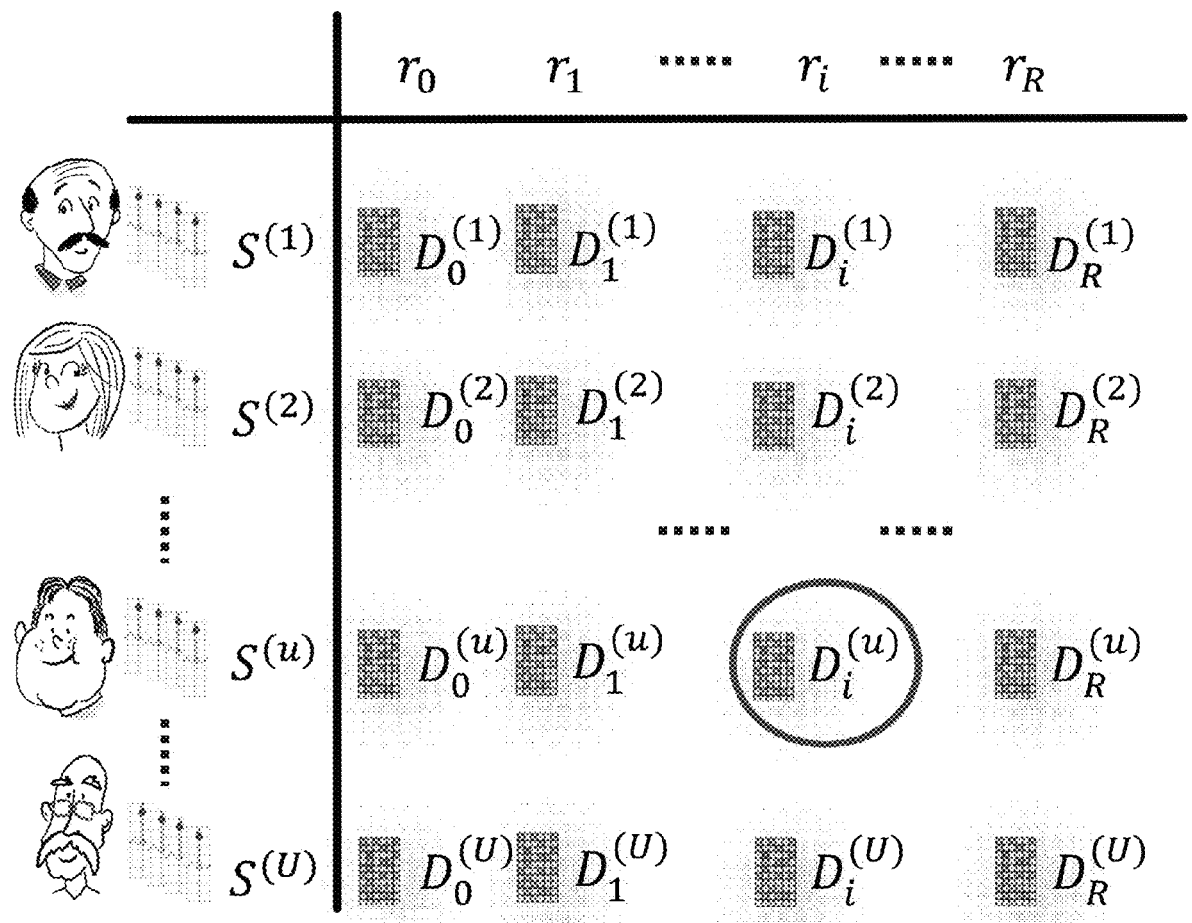
FIG. 30 illustrates a simplified example embodiment of a dictionary of a user heart-rate.

At 2804, a dictionary $D_i^{(u)}$ is learned for each user $u=1, \ldots U$, and for each heart-rate $r_0, \ldots, r_R$ of the heartbeat data. The dictionaries may be learned, for example, as discussed above with reference to FIGS. 1-12. For example, the dictionaries may be learned using a K-SVD algorithm. FIG. 30 illustrates an embodiment of a dictionary $D_i^{(u)}$ learned for the heart-rate $r_i$ of the user $S^{(u)}$, for example, using a K-SVD algorithm. The method proceeds to 2806.

At 2806, the optimization problem of equation 21 is solved for each set of dictionaries, for example, using ADMM to generate respective adoption operators for the set of dictionaries. At 2808, the solutions to the optimization problem are output as a family of adaption operators or transformations $\mathcal{F}$.

Figure 31:
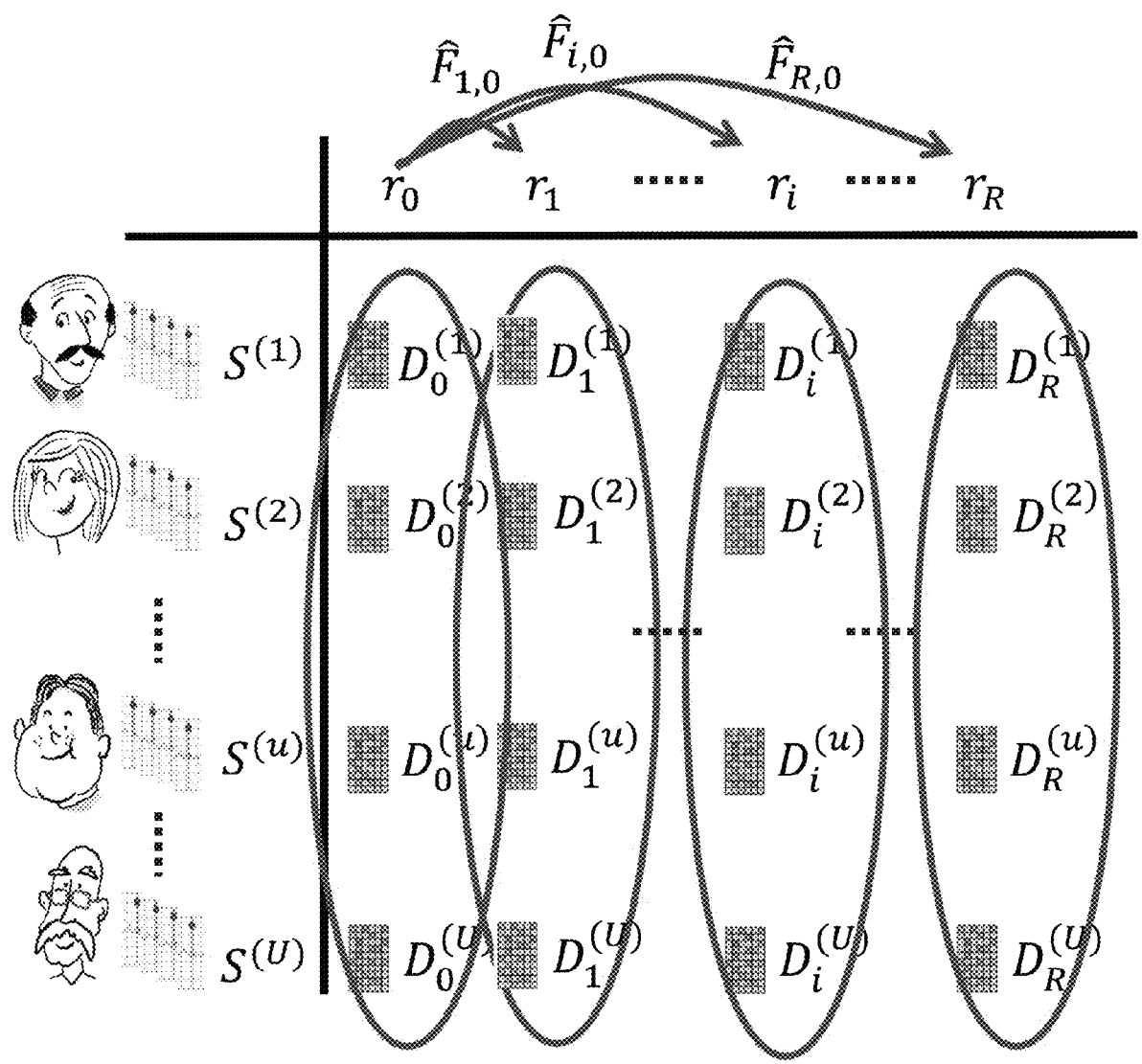
FIG. 31 illustrates example sets of dictionaries for which an optimization problem is solved with respect to pairs of heart-rates.

For example, with $r_0$ representing the source heart-rate and $\{D_i^{(u)}: u=1, \ldots, U\}$ representing the related set of dictionaries, the optimization problem of equation 21 is solved for each set of dictionaries with $r_i=r_1, \ldots, r_R$ using, for example, ADMM, to compute $\hat{F}_{r_i,0}$. A reference heart-rate (e.g., a resting heart-rate) may vary from user to user. Issues related to this variation may be avoided by considering multiple source heart rates (e.g., $r_i=r_1, \ldots, r_R$). FIG. 31 illustrates example sets of dictionaries for which the optimization problem of equation 21 is solved with respect to heart rate $r_0$. The output of 2808 in this example is a family of adaption operator transformations:

$$\mathcal{F} = (\hat{F}_{1,0}, \ldots \hat{F}_{i,0}, \ldots \hat{F}_{R,0})$$

Figure 32:
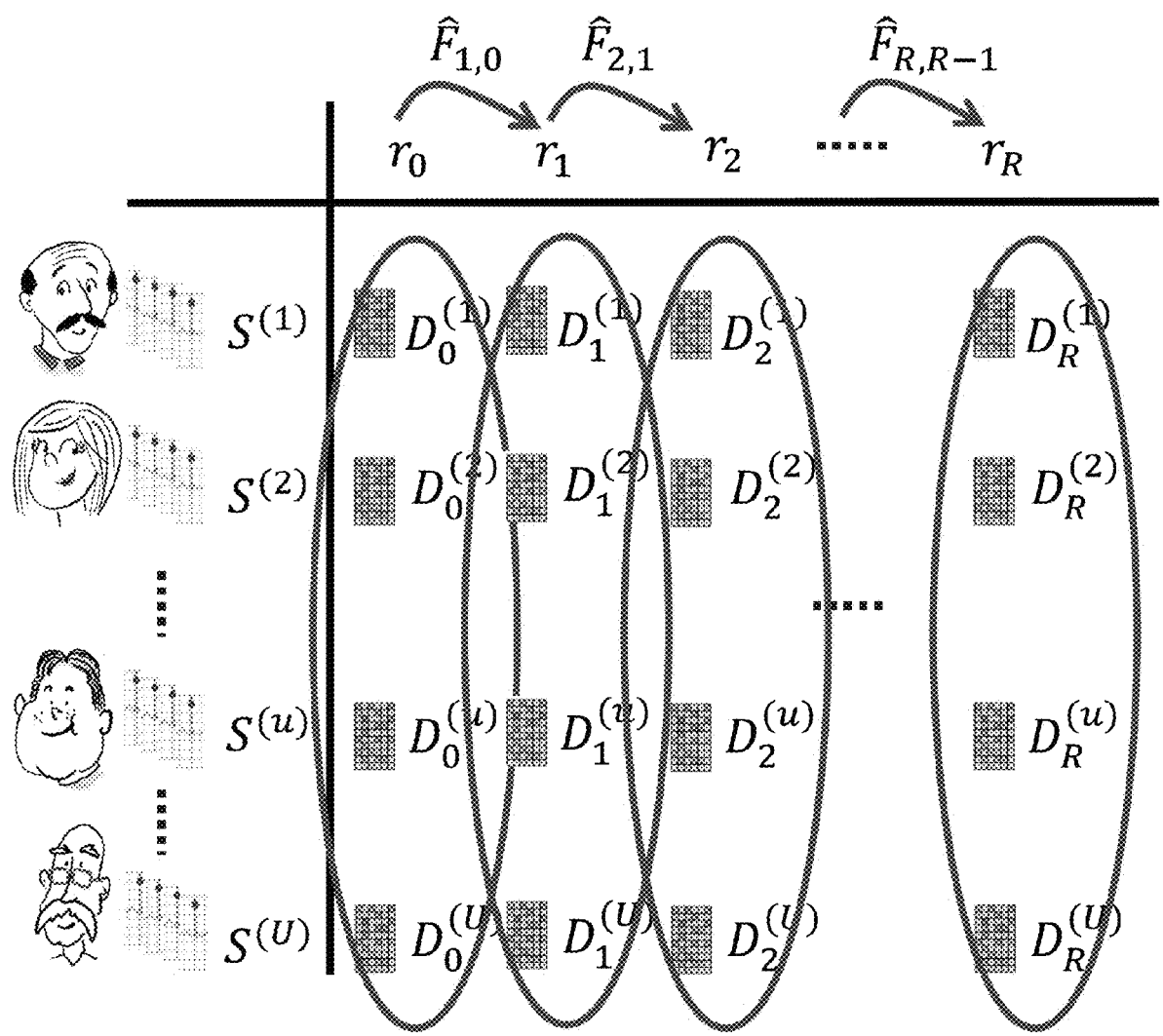
FIG. 32 illustrates alternative example sets of dictionaries for which an optimization problem is solved.

In another example, for each pair of sets of dictionaries $\{D_{i-1}^{(u)}: u=1, \ldots, U\}$ and $\{D_i^{(u)}: u=1, \ldots, U\}$ with $r_i=r_1, \ldots, r_R$, the optimization problem of equation 21 is solved, for example, using ADMM to compute $\hat{F}_{i,i-1}$. FIG. 32 illustrates example sets of dictionaries for which the optimization problem of equation 21 is solved. The output of 2808 in this example is a family of transformations:

$$\mathcal{F} = (\hat{F}_{1,0}, \hat{F}_{2,1} \ldots \hat{F}_{i,i-1}, \ldots \hat{F}_{R,R-1}).$$

Embodiments of the method 2800 may perform additional acts not shown in FIG. 28, may perform the acts of FIG. 28 in different orders, may omit acts shown in FIG. 28, may modify acts shown in FIG. 28, and may combine or split acts shown in FIG. 28. For example, in an embodiment the method 2800 may be modified to filter the heartbeat data prior to learning the dictionaries.

Figure 33:
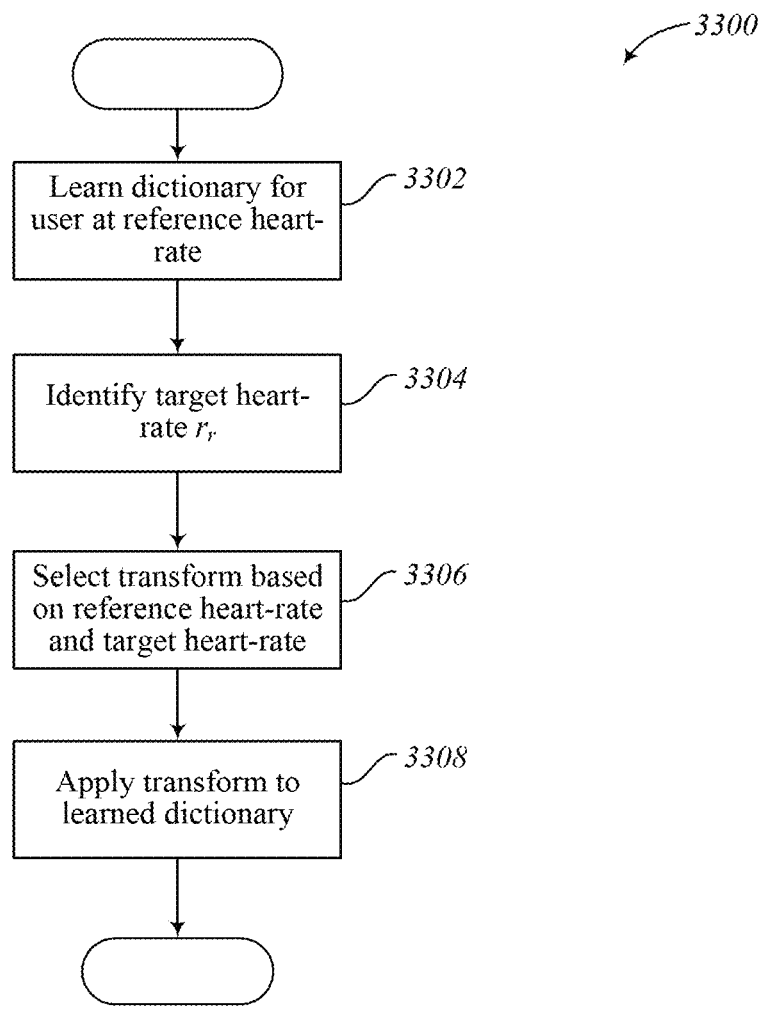
FIG. 33 illustrates an embodiment of a subroutine or method of adapting a system using a family of adaption operators.

FIG. 33 illustrates an embodiment of a subroutine or method 3300 of adapting a system, such as the system 1000 of FIG. 10, for use with a new user using a family of adaption operators $\mathcal{F}$. The method 3300 may be employed, for example, by an embodiment of a system 1000 of FIG. 10, by a server, such as the server 1050 of FIG. 10, and various combinations thereof.

At 3302, a dictionary $D_0^{(U+1)}$ is learned for the new user U+1 at a reference heart-rate $r_0$, for example, at a resting heart-rate. This may be performed, for example, as discussed above with reference to FIGS. 1-12. The method proceeds from 3302 to 3304.

At 3304, a target heart-rate $r_r$ for user U+1 is identified. This may be performed, for example, by selecting one or more target heart rates (e.g., in order to generate a set of dictionaries for various target heart rates $r_i$, for the user U+1), by measuring a punctual heart-rate RR and determining a local heart-rate HR, such as discussed above with reference to FIG. 16, etc.

The method proceeds from 3304 to 3306. At 3306, a transform in the family of transforms $\mathcal{F}$ is selected based on the reference heart rate $r_0$ for the user U+1 and the target heart rate $r_r$ (e.g., with reference to the examples discussed above, transform $\hat{F}_{r_r,0}$ or transform $\hat{F}_{1,0} \cdot \hat{F}_{2,1} \cdot \ldots \cdot \hat{F}_{r,r-1}$. The selection of the transform in the family of transforms $\mathcal{F}$ is independent of factors other than the reference and target heart-rates, such as the user U+1, the state of user U+1, the device position and the device model. The method proceeds from 3306 to 3308.

At 3308, the method applies the selected transform to the learned dictionary $D_0^{(U+1)}$ to generate a transformed dictionary for the user U+1, $D_r^{(U+1)}$:

$$D_r^{(U+1)} := \hat{F}_{0,r} \cdot D_0^{(U+1)}$$

The transformed dictionary, $D_r^{(U+1)}$, may be employed, for example, to populate a set of dictionaries for user U+1, to classify individual heartbeats of user U+1 as normal or abnormal (see FIG. 34), etc.

Embodiments of the method 3300 may perform additional acts not shown in FIG. 33, may perform the acts of FIG. 33 in different orders, may omit acts shown in FIG. 33, may modify acts shown in FIG. 33, and may combine or split acts shown in FIG. 33. For example, in an embodiment the method 3300 may be modified to retrieve the selected transform from a server after act 3306.

Figure 34:
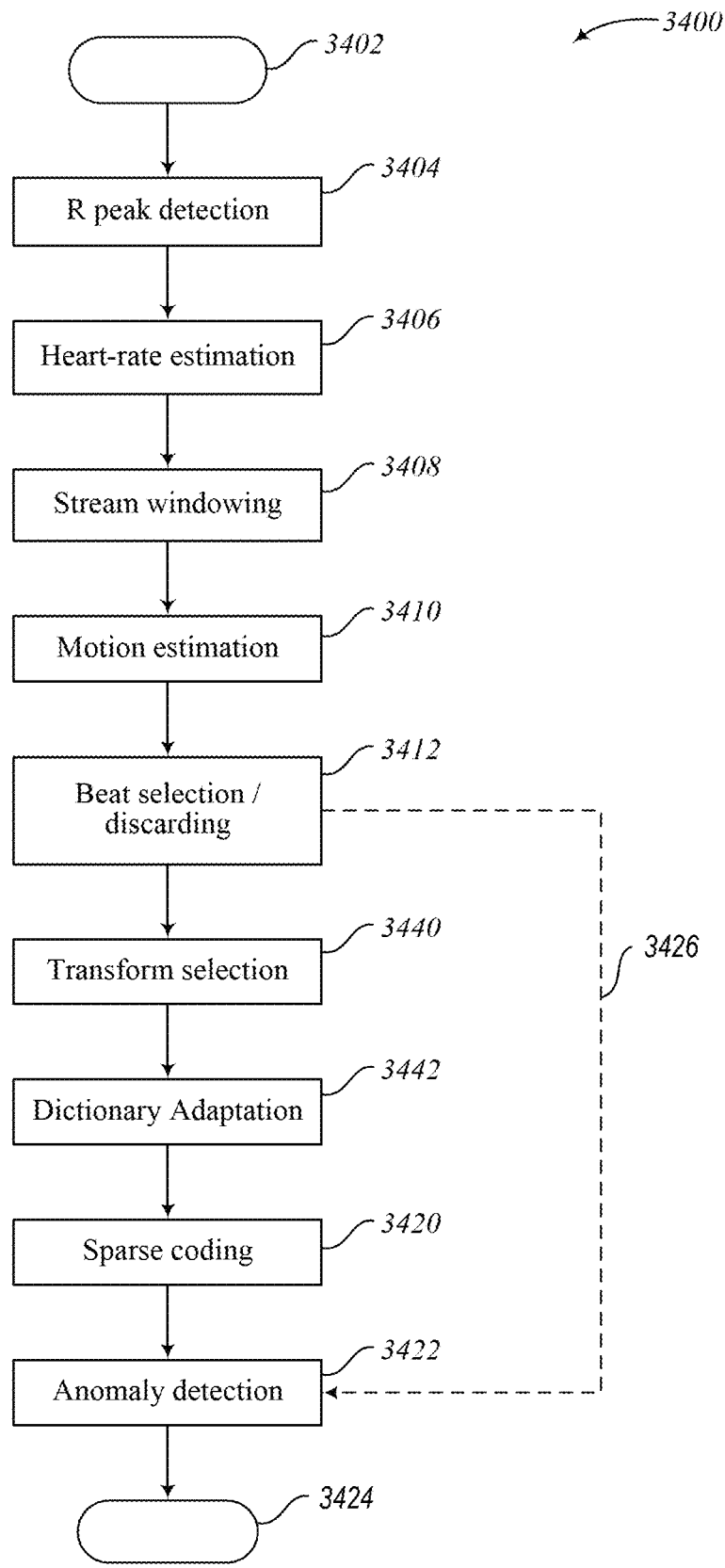
FIG. 34 illustrates an embodiment of a subroutine or method to detect abnormal heart beats using a trained dictionary and a selected adaption operator.

FIG. 34 illustrates an embodiment of a subroutine or method 3400 to detect abnormal heart beats using, for example, a trained dictionary, an adaption operator or transform, a current ECG trace and accelerometer data. FIG. 17 is a graphical representation of an ECG trace that may be provided as input to the subroutine 3400. The method 3400 may be applied to individual beats, and may be applied sequentially to a series of individual beats, or in parallel to sets of individual beats. The output for each beat is an indication of whether the beat is normal or anomalous. The subroutine 3400 extracts single heartbeats from the continuous ECG stream in input. Also, some preprocessing and filtering steps may be employed before analyzing the signal. The method 3400 begins at 3402 and proceeds to 3404.

At 3404, the R-peaks of each heart beat are detected. This may be done, for example, by filtering the ECG traces, for example using two median filters to remove the baseline, and detecting the R-peaks in the filtered signal using, for example, a Pan-Tompkins algorithm. See Pan, et al., *A real-time qrs detection algorithm*, Biomedical Engineering, IEEE Transaction on, No. 3, pp 230-236, 1985. FIG. 18 is a graphical illustration of an example of beats extracted from an ECG trace. The method 3400 proceeds from 3404 to 3406.

At 3406, a punctual heart rate (RR) is measured, for example by computing the time difference between R-peaks of a beat and an adjacent beat. A local heart rate (HR) is determined for reference windows (time intervals), which may be, for example, of a fixed size such as 10 seconds. Statistical analysis may be employed to determine the local heart rate HR, for example, the median of the punctual heart rates for beats in the window may be employed as the local heart rate in an embodiment. In an embodiment, the interquartile range IQR=$Q_3$-$Q_1$ may also be determined, where $Q_3$ and $Q_1$ are respectively the third and first quartile of the RRs in the window. Outliers in the punctual heart rate may be identified, for example, based on thresholds. For example, RRs below $Q_1$-1.5(IQR) or above $Q_3$+1.5(IQR) may be identified as outliers. Other methods of identifying outliers may be employed, such as Median Absolute Deviation (MAD). It is noted that different thresholds and other criteria may be employed in an embodiment to identify outliers in the training and detecting methods or routines. RRs identified as outliers may be removed prior to anomaly detection, as discussed elsewhere herein.

The method proceeds from 3406 to 3408. At 3408, the beats of the stream are windowed, for example using a reference window of a reference window size, which may be a fixed size, such as, for example, R−0.35 seconds, R+0.35 seconds. For each R-peak, a fixed-size window with a center located in the peak is extracted from the ECG stream. For example, one can consider windows of size 0:7 s (0:35 s around the R-peak). Other window sizes may be selected, for example to facilitate selecting all the PQRST waves of the current beat without including waves from the previous or subsequent beats. The chosen fixed-size window size may be referred to as a reference window size (RWS) and considered as the reference window for the particular user. At this level, heartbeats, or simply beats, refers to the collection of samples inside the chosen window. FIG. 15 is a graphical representation of an example of a windowed beat of an ECG trace.

The method proceeds from 3408 to 3410. At 3410, motion estimation is performed. In an embodiment, accelerometer data is provided as an input. The ECG data stream and the accelerometer data are synchronized or assumed to be synchronized. For each heartbeat the energy of the acceleration (EE) of the associated accelerometer data is measured. In an embodiment, the energy of the acceleration is defined as the $l_2$ norm of the accelerometer data corresponding to a window of size RWS around the R-peak. Outliers in the accelerometer data distribution may be identified, for example, using confidence intervals based on sliding windows along the trace. See, FIGS. 7-8 and the description thereof. It is noted that different thresholds and other criteria may be employed in an embodiment to identify outliers in the training and detecting methods or subroutines. FIG. 14 is a graphical representation of an example of accelerometer data. The method proceeds from 3410 to 3412.

At 3412, beats are selected so as to exclude beats which may give rise to false positive indications of anomalies. In an embodiment, this may be done by excluding beats which have both (i) a punctual heart rate identified as an outlier with respect to a local heart rate and (ii) corresponding accelerometer data identified as outlier. Such beats may be excluded because the outlier status under both criteria may be an indicator the beats are highly affected by noise or motion artifacts, or failures in the sensing process due, for example, in involuntary movements of the user. It is noted that a beat which is an outlier with respect to the RR distribution, but which is an inlier with respect to the accelerometer data, may be an anomalous beat (e.g., an atrial premature beat, a rhythmical anomaly beat, etc.). Thus, in an embodiment beats which are outlier with respect to condition (i), but which are inlier with respect to condition (ii), may be included in the beats selected for anomaly detection. In an embodiment, a beat which is outlier with respect to condition (i), but which is inlier with respect to condition (ii) may be classified as anomalous at 3412, with an indication the beat should be classified as anomalous being taken into account at 3422, as shown in FIG. 34 by the dashed line 3426.

It also is noted that beats which are inlier with respect to condition (i), but which are outlier with respect to condition (ii), may be selected for anomaly detection in an embodiment because the inlier status with respect to condition (i) may be an indicator that the morphology of the beat is preserved, and thus useful information may be obtained by including the beat in the analysis. The selected beats may also be subjected to preprocessing at 3412, such as obtaining a zero-mean vectors by subtracting the mean (e.g., vertically translating the beats). The method proceeds from 3412 to 3440.

At 3440, an adaption operator or transform is selected from a family of adaption operators based on a heart-rate associated with the heartbeats (e.g., the heart-rate LR determined at 3406) and a reference heart-rate associated with a learned dictionary D associated with the user. The transform is selected independent of other factors associated with the heartbeats, such as the specific user, the state of the user (e.g., resting, running, biking, etc.), the device position and the device model. This may be done, for example, as described above with reference to act 3306 of method 3300.

The method proceeds from 3440 to 3442. At 3442, the selected transform is applied to the learned dictionary D associated with the user to generate an adapted dictionary $D_r$. This may be done, for example, as described above with reference to act 3308 of method 3300. The method 3400 proceeds from 3442 to 3420.

At 3420, the T-sparse approximation x of test beat is determined with respect to the adapted dictionary $D_r$. This may be done using an OMP algorithm, such as the method 300 of FIG. 3 or the algorithm of Table 1, as discussed in more detail elsewhere herein.

The method 3400 proceeds from 3420 to 3422, where detection of anomalous beats is performed. This may be done by determining an anomaly indicator for a test beat s based on the sparse approximation x of test beat s with respect to the adapted dictionary $D_r$, comparing the anomaly indicator to expected values or ranges of values for the anomaly indicator, and classifying the test beat as normal or anomalous based on the comparison. An example anomaly indicator is the root-mean-square error, as discussed in more detail elsewhere herein. The root-mean-square error may be compared with expected values of the root-mean-square error and the beat may be classified as normal or anomalous based on the comparison. One or more thresholds, one or more threshold ranges and one or more look-up tables may be employed to classify a beat as normal or anomalous. See the discussion of anomaly indicators and FIG. 6 above. As discussed above with respect to act 3412, a beat which is outlier with respect to condition (i), but which is inlier with respect to condition (ii) may be classified as anomalous at 3412, with an indication the beat should be classified as anomalous being taken into account at 3422, as shown by the dashed line 3426.

The method 3400 proceeds from 3422 to 3424, where the subroutine may return an indication of whether a beat is anomalous, where further processing may occur, etc. Embodiments of the method 3400 may perform additional acts not shown in FIG. 34, may perform the acts of FIG. 34 in different orders, may omit acts shown in FIG. 34, may modify acts shown in FIG. 34, and may combine or split acts shown in FIG. 34. For example, in an embodiment the method 3400 may be modified to check whether additional beats are to be classified at 3422 and return to 3404 to process the next beat when it is determined that additional beats remain to be classified. In another example, the subroutine may be modified to perform error processing, such as in response to a beat being classified as anomalous, initiating a transmission of data related to the beat classified as anomalous. In another example, the routine 3400 may be modified to track a proportion of beats excluded from the beats selected at 3412 within a threshold period of time, and when the proportion indicates the dictionary for the reference heartbeat may no longer be valid, to call a subroutine to update the dictionary, such as the subroutine 1200 of FIG. 12. Thresholds may be employed to determine whether the dictionary may no longer be valid. In another example, embodiments of the routine 3400 may be modified to perform additional acts, such as one or more of acts 1614, 1616 and 1618 of routine 1600 of FIG. 16. In other words, beat adaption may be employed in an embodiment, a first dictionary adaption may be applied in accordance with act 1618 of method 1600 and a second dictionary adaption may be employed in accordance with acts 3440 and 3442 of method 3400 in an embodiment, etc.

Some embodiments may take the form of or include computer program products. For example, according to one embodiment there is provided a computer readable medium including a computer program adapted to perform one or more of the methods or functions described above. The medium may be a physical storage medium such as for example a Read Only Memory (ROM) chip, or a disk such as a Digital Versatile Disk (DVD-ROM), Compact Disk (CD-ROM), a hard disk, a memory, a network, or a portable media article to be read by an appropriate drive or via an appropriate connection, including as encoded in one or more barcodes or other related codes stored on one or more such computer-readable mediums and being readable by an appropriate reader device.

Furthermore, in some embodiments, some of the systems and/or modules and/or circuits and/or blocks may be implemented or provided in other manners, such as at least partially in firmware and/or hardware, including, but not limited to, one or more application-specific integrated circuits (ASICs), digital signal processors, discrete circuitry, logic gates, standard integrated circuits, state machines, look-up tables, controllers (e.g., by executing appropriate instructions, and including microcontrollers and/or embedded controllers), field-programmable gate arrays (FPGAs), complex programmable logic devices (CPLDs), etc., as well as devices that employ RFID technology, and various combinations thereof The various embodiments described above can be combined to provide further embodiments. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A method, comprising:
    determining a heart-rate associated with a heartbeat signal, wherein the heartbeat signal is an electrocardiogram signal;
    selecting a transform based on the determined heart-rate associated with the heartbeat signal and a reference heart-rate associated with a dictionary of a sparse approximation model, wherein the transform is selected independent of other factors associated with generation of the heartbeat signal;
    applying the selected transform to the dictionary of the sparse approximation model, generating an adjusted dictionary of the sparse approximation model;
    generating a sparse approximation of a beat in a set of beats detected in the heartbeat signal with respect to the adjusted dictionary; and
    detecting anomalous heartbeats in the heartbeat signal using the adjusted dictionary of the sparse approximation model, the detecting of the anomalous heartbeats including classifying the beat in the set of detected beats as anomalous based on the generated sparse approximation.

2. The method of claim 1 wherein selecting the transform comprises selecting one of a family of transforms associated with respective pairs of heart-rates.

3. The method of claim 1, comprising:
    generating the dictionary of the sparse approximation model.

4. The method of claim 1 wherein the transform is a first transform, comprising:
    selecting a second transform based on the determined heart rate and at least one other factor associated with the heartbeat signal; and
    applying the first and second transforms to the dictionary of the sparse approximation model.

5. The method of claim 1 wherein classifying the beat in the set of beats as anomalous based on the sparse approximation comprises:
    determining a root-mean-square error associated with the sparse approximation of the beat;
    comparing the root-mean-square error to a threshold error; and
    classifying the beat in the set of beats as anomalous or normal based on the comparison.

6. The method of claim 1, comprising:
    in response to classification of the beat in the set of beats as anomalous, initiating a transmission of data related to the beat in the set of beats.

7. The method of claim 1 wherein the beat is an adjusted beat.

8. The method of claim 1 comprising filtering beats in the set of detected beats.

9. A device, comprising:
an interface, which, in operation receives a test heartbeat signal: and
signal processing circuitry, which, in operation:
determines a heart-rate associated with the test heartbeat signal, wherein the test heartbeat signal is an electrocardiogram signal;
selects a transform based on the determined heart-rate associated with the test heartbeat signal and a reference heart-rate associated with a dictionary of a sparse approximation model, wherein the transform is selected independent of other factors associated with generation of the test heartbeat signal;
applies the selected transform to the dictionary of the sparse approximation model, generating an adjusted dictionary of the sparse approximation model;
generates a sparse approximation of a beat in a set of beats detected in the test heartbeat signal with respect to the adjusted dictionary; and
detects anomalous heartbeats in the test heartbeat signal using the adjusted dictionary of the sparse approximation model, wherein detecting the anomalous heartbeats includes classifying the beat in the set of detected beats as anomalous based on the generated sparse approximation.

10. The device of claim 9 wherein the transform is a first transform and the signal processing circuitry, in operation:
selects a second transform based on the determined heart-rate and at least one other factor associated with the test heartbeat signal; and
applies the first and second transforms to the dictionary of the sparse approximation model.

11. The device of claim 9 wherein the classifying the beat in the set of beats as anomalous based on the sparse approximation comprises:
determining a root-mean-square error associated with the sparse approximation of the beat;
comparing the root-mean-square error to a threshold error; and
classifying the beat in the set of beats as anomalous or normal based on the comparison.

12. The device of claim 9 wherein the signal processing circuitry, in response to classification of the beat in the set of beats as anomalous, initiates a transmission of data related to the beat in the set of beats.

13. The device of claim 9 wherein the signal processing circuitry, in operation, adjusts the beat in the set of beats.

14. The device of claim 9 wherein the signal processing circuitry, in operation, filters beats in the set of detected beats.

15. The device of claim 9 wherein,
the interface, in operation, receives a training heartbeat signal; and
the signal processing circuitry, in operation:
detects a beat of the training heartbeat signal;
associates a reference heart rate and an energy of acceleration with the detected beat of the training heartbeat signal;
selectively includes the detected beat of the training heartbeat signal in a set of training data based on the heart rate and energy of acceleration associated with the detected beat in the training heartbeat signal; and
generates the dictionary of the sparse representation model using the set of training data.

16. A system, comprising:
a sensor, which, in operation, generates heartbeat signals;
an accelerometer, which, in operation, generates one or more acceleration signals; and
signal processing circuitry, which, in operation:
determines a heart-rate associated with a test heartbeat signal, wherein the test heartbeat signal is an electrocardiogram signal;
selects a transform based on the determined heart-rate associated with the test heartbeat signal and a reference heart-rate associated with a dictionary of a sparse approximation model, wherein the transform is selected independent of other factors associated with generation of the test heartbeat signal;
applies the selected transform to the dictionary of the sparse approximation model, generating an adjusted dictionary of the sparse approximation model;
generates a sparse approximation of a beat in a set of beats detected in the test heartbeat signal with respect to the adjusted dictionary; and
detects anomalous heartbeats in the test heartbeat signal using the adjusted dictionary of the sparse approximation model, wherein detecting the anomalous heartbeats includes classifying the beat in the set of detected beats as anomalous based on the generated sparse approximation.

17. The system of claim 16 wherein the transform is a first transform and the signal processing circuitry, in operation:
selects a second transform based on the determined heart-rate and at least one other factor associated with the test heartbeat signal; and
applies the first and second transforms to the dictionary of the sparse approximation model.

18. The system of claim 16 wherein, the signal processing circuitry, in operation:
detects a beat of a training heartbeat signal;
associates a reference heart rate and an energy of acceleration with the detected beat of the training heartbeat signal;
selectively includes the detected beat of the training heartbeat signal in a set of training data based on the heart rate and energy of acceleration associated with the detected beat in the training heartbeat signal; and
generates the dictionary of the sparse representation model using the set of training data.

19. A non-transitory computer-readable medium having contents which configure a heart-rate monitoring device to perform a method, the method comprising:
determining a heart-rate associated with a test heartbeat signal, wherein the test heartbeat signal is an electrocardiogram signal;
selecting a transform based on the determined heart-rate associated with the test heartbeat signal and a reference heart-rate associated with a dictionary of a sparse approximation model, wherein the transform is selected independent of other factors associated with generation of the test heartbeat signal;
applying the selected transform to the dictionary of the sparse approximation model, generating an adjusted dictionary of the sparse approximation model;
generating a sparse approximation of a beat in a set of beats detected in the heartbeat signal with respect to the adjusted dictionary; and
detecting anomalous heartbeats in the test heartbeat signal using the adjusted dictionary of the sparse approximation model, the detecting of the anomalous heartbeats including classifying the beat in the set of detected beats as anomalous based on the generated sparse approximation.

20. The non-transitory computer-readable medium of claim 19 wherein the contents comprise instructions executed by processing circuitry of the heart-rate monitoring device.

21. The non-transitory computer-readable medium of claim 19 wherein the method comprises:
  detecting a beat of a training heartbeat signal;
  associating a reference heart rate and an energy of acceleration with the detected beat of the training heartbeat signal;
  selectively including the detected beat of the training heartbeat signal in a set of training data based on the heart rate and energy of acceleration associated with the detected beat in the training heartbeat signal; and
  generating the dictionary of the sparse representation model using the set of training data.

\* \* \* \* \*